US011173203B2

(12) United States Patent
Vahlenkamp et al.

(10) Patent No.: US 11,173,203 B2
(45) Date of Patent: Nov. 16, 2021

(54) PARAMYXOVIRUS AND USES THEREOF

(71) Applicant: Boehringer Ingelheim Vetmedica GmbH, Ingelheim am Rhein (DE)

(72) Inventors: Thomas W. Vahlenkamp, Markkleeberg (DE); Michael Sieg, Zeitz (DE)

(*) Notice: Subject to any disclaimer, the term of this patent is extended or adjusted under 35 U.S.C. 154(b) by 43 days.

(21) Appl. No.: 16/327,981

(22) PCT Filed: Aug. 24, 2017

(86) PCT No.: PCT/EP2017/071392
§ 371 (c)(1),
(2) Date: Feb. 28, 2019

(87) PCT Pub. No.: WO2018/037100
PCT Pub. Date: Mar. 1, 2018

(65) Prior Publication Data
US 2020/0268875 A1 Aug. 27, 2020

(30) Foreign Application Priority Data
Aug. 25, 2016 (EP) .................... 16185761

(51) Int. Cl.
*A61K 39/155* (2006.01)
*A61K 39/39* (2006.01)
*A61P 31/14* (2006.01)
*C12N 7/00* (2006.01)
*G01N 33/569* (2006.01)
*C07K 14/115* (2006.01)
*A61K 39/42* (2006.01)
*A61K 39/00* (2006.01)

(52) U.S. Cl.
CPC ............ *A61K 39/155* (2013.01); *A61K 39/39* (2013.01); *A61K 39/42* (2013.01); *A61P 31/14* (2018.01); *C07K 14/115* (2013.01); *C12N 7/00* (2013.01); *G01N 33/56983* (2013.01); *A61K 2039/552* (2013.01); *G01N 2333/115* (2013.01)

(58) Field of Classification Search
None
See application file for complete search history.

(56) References Cited

U.S. PATENT DOCUMENTS

2020/0268875 A1* 8/2020 Vahlenkamp ........... A61P 31/12

FOREIGN PATENT DOCUMENTS

| JP | 2015198654 | 11/2015 |
| WO | 2005013918 A2 | 2/2005 |

(Continued)

OTHER PUBLICATIONS

Sieg et al. (Viruses. 2019; 11, 146: doi:10.3390/v11020146).*

(Continued)

*Primary Examiner* — Shanon A. Foley
(74) *Attorney, Agent, or Firm* — Steffan Finnegan

(57) ABSTRACT

The present invention relates to a novel feline paramyxovirus. The paramyxovirus of the present invention is a (-)ssRNA virus and has in one aspect a genome which is complementary to the nucleic acid according to SEQ ID NO:1 or SEQ ID NO:8. The invention further relates to corresponding nucleic acids and polypeptides, antibodies and vaccines. Further, the invention relates to medical uses and diagnostic methods concerning the paramyxovirus of the invention.

7 Claims, 9 Drawing Sheets
Specification includes a Sequence Listing.

(56) References Cited

FOREIGN PATENT DOCUMENTS

| WO | 2013107290 | 7/2013 |
|---|---|---|
| WO | 2018037100 A1 | 3/2018 |

OTHER PUBLICATIONS

Alignment of Geneseq database access No. BAQ99926 Yuen et al 2013 with instant Seq ID No. 1.*
Alignment of Geneseq database access No. BAQ99926 Yuen et al 2013 with instant Seq ID No. 8.*
Alignment of Geneseq database access No. BAQ99926 Yuen et al 2013 with Seq ID No. 9.*
Alignment of Geneseq database access No. BAQ99926 Yuen et al 2013 with Seq ID

A.

B.

C.

D.

SEQUENCE LISTING

<160> NUMBER OF SEQ ID NOS: 14

<210> SEQ ID NO 1
<211> LENGTH: 16047
<212> TYPE: DNA
<213> ORGANISM: Feline Paramyxovirus-Type 2
<220> FEATURE:
<223> OTHER INFORMATION: complementary sequence of the genome of Feline
      Paramyxovirus-Type 2 (FPaV-2), Strain Gordon

<400> SEQUENCE: 1

```
accagacaaa gatgtctgtg acctattcta acggttagat tattacttga tatttaggaa      60
taacgattcc attagtcagg taagggagag gaatcagtta ttctataatg gctagtttac     120
tcaggtcact tgcggcattc aagaaacaca gagaacaacc aactgttcct tctgggtcag     180
gagggacgat caaaggatta aaaaatacaa ttattgtgcc tgttcctgga gatacagtca     240
tcactaccag atcgaactta ctgttcagat tagtctacat aattggtaat ccagatacac     300
ctttaagcac ttcaacaggg gcaataatat cattgttgac attatttgtt gaatctccag     360
gtcaattaat tcaaagaatc gctgatgatc ctgatgctgt ttttaaatta gtagaggtgg     420
ttcctgaggt tggtaatcct ggagaattaa cttttgcatc tagaggaatt aacttggata     480
aacaagctca acaatacttt agattggctg agaaaaatga tcaaggatat tatgtaagtt     540
tggggtttga aaatccacca aatgatgatg atataacgtc aagtcctgaa atctttaatt     600
atattttagc atctgtactt gcacagatct ggattctcct agctaaggct gtaactgctc     660
```

```
cagacacagc tgctgaggct gaaaaccgta ggtggattaa attgatgcaa caacgcagag    720
tggatggtga gcttagatta agtaaaggat ggttggactt agtgaggaat aaaatcgcat    780
cggatatcac aattagaagg tttatggtag cattagttct tgacattaaa cgttctcctg    840
gaacaagacc aagaattgct gaaatgattt gtgatataga caattatatt gtggaggccg    900
gactggcaag ttttctgtta actatcaaat ttggtataga aacacgttac ccggcattag    960
cgttacatga gttttcgggg gaattagcca ctattgaagg actcatgaaa ttgtaccagt   1020
ctatgggaga aatggcacca tacatggtca ttctagagaa ttcgatccag actaggttta   1080
gtgctgggtc ttatccgtta ctctggagct atgctatggg tgttggtgta gaacttgaaa   1140
gatcaatgag tggattaaac ttcacaagaa gtttctttga tcctacgtac ttcaggttgg   1200
gtcaggagat ggtaagaagg tcttcaggaa tggttaatag ctcatttgcc aaagaacttg   1260
gactatctga acatgaaaca caacttgtta gccagatcat taactcaggt ggtgagtcag   1320
gtataccgaa atttgatgga tttagagcaa acccaacaac atttctaggg gctaaggaca   1380
acatcactga taggagtgaa gatccattga ttgcaattcc agggtcatca ggacaaccat   1440
tgccaggtta tgaccccaat atctcaggtg actcatatag aattgatagt agcactaaag   1500
acacaaacaa tatatcagat ggaggaacaa atccaagtca tgatgtttcc aattctgcta   1560
tggaagagct gagaagattg gtagagtcta ccaacaagat tgatacaaag aaatctgaaa   1620
gcccaggcat cgttaatcat tacaacgata ctgaccttct gagataataa ggatatattc   1680
aggtagatct ttacagaatt taaattaaga aaaacttagg acctcaaggt tcacactcct   1740
ctggccttta tcagaattcg gccaattcct cactcactcc atgtcagcag aacaaatcca   1800
acaagttaga catggccttg aatccttgca agagatcaaa acaaccctc caccctctca   1860
agatgtcaat cttgccaggg aaatttacga atccattaaa caaacaggaa caccttcaac   1920
acaaggaggg accattacag gaaataatac tgcgtcaggg tgtgacaatt actcaatgca   1980
tagccaggga tcaggtcctt ctgtttcagg tgctgacaag aatatcgaga gacttactgg   2040
acccgattat tcagaattat gggatccaga aggtaacctc tgcatgctat tcgaaagcga   2100
tgatgatgac aacaattatt cagagattaa tggccggtct accgctatcg aaggattgga   2160
tgaacagaat aataaggacc caggtattaa acaatcagga gatcagtgtt ctgaaggagt   2220
gtctaagatt aattcatctt ctagtcccca agaagctaca ttatcttctg ggagatctga   2280
tatatctggg acaggagtat ctccctgtgc ctctttggat ataactgtta atgaattaga   2340
agatgcaact gttaagaata gtaataatat gaaaggaaat tggccaatcc caaagttgct   2400
tgtcaaacca ccaccaagaa tgaaatcact ttctgactct gttacaccat taaaagggc   2460
caccgacggg aaatcagtct tacctgggat ggagattaca ttgtccggga gaatggtgc   2520
aaccctacct gtacacccat ttacacaacc tataaaagac tcaaatgcag atgtaagcaa   2580
tgtccgtcaa catgtcccaa gtgtgactga tggtcatagt gatgataatg aggaagtacc   2640
cggtttgcat aaagaaacta tagacaaagc tgatctatct atgcaggaca tatacaattt   2700
aattcttgga tttaaggatg attacaggaa actatcaaat aaattggata tgatactaga   2760
gatgaaacaa gatattgata tccttaaaaa gagtagtgca aaaatacaac ttgcattatc   2820
aacaattgaa ggacatctgt ccagtgttat gattgctatt ccaggttcag gtattgatat   2880
aaatcaagat gagaagaagg atcaattaaa ctctgactta agccattac tagggaggga   2940
ccattgccgt gcatttcgtg aagtcactaa tcctttagat gaaacgtcat tgaccaacgc   3000
tccgaccaaa catgttgcta agatcaacaa aaattgcact cttcagaaaa tcaataacaa   3060
```

```
tgagacatct gcaattaagt ttgtacctaa tgatagccat gcaagtatct cgactatcaa    3120
gtctattgtc aaatcctcaa accttaatca agagcttaaa gtcaagttac tgacaattct    3180
atctcaaatt aaaggggtag acaatattaa ggagttttat gagaaagtta tgatattgat    3240
caagaataat aactgatctt gactaatcaa tagatactac ttatcaaatc tcgctctgac    3300
atcaagtgaa ttcatcttta ttaacaagta ttaatcttaa ataattataa aaaacttagg    3360
agttcaggat tagtgggtca tatacaatat gactgagata ttcaatctgg atgaaagttc    3420
atggtcagtc aagggaacac tggacccatt gacgcctgat acttatcctg atgggcgcct    3480
agtacccaag attcgggtta ttgatcccgg tctaggtgat cgtaaaagtg gaggatatat    3540
gtacttactc cttcacggtg tcatcgagga cagtgagacc gtcataaatc cgaaagggag    3600
agcatttgga gctttccctt taggcgtagg gcaatcaacc gagaacccag aagacttatt    3660
taaggaaata ttaaccctca acattgttac tcgcaggact gctggcttca atgaaaaatt    3720
ggtgtattat aatactacac ctctaaatct actaacccct tggaaaaaag tactagcata    3780
tggaagtatc tttactgcta atcaggtctg caataataca agttctatcc ctatagacat    3840
tcctcagaaa tttcgacctg tctatttaac tgttaccaag ttatcggatg atggatatta    3900
tcagatacct aaaatgatac aggatttcaa atcatcaaac tctgttgcat ttaacatcct    3960
tgtgcatcta tcaatgggaa caattttact tgactcatct aaaggctctc gagtaggaaa    4020
ccctgcagaa aatttgatca cattcatgat tcatattggg aatttcaaac ggaagaataa    4080
taaagcttat tctcccgaat attgtaagag gaaaataatg aggcttggat taattttctc    4140
actaggagcc attggtggaa caagtttgca tattcgatgc acaggcaaaa tgagtaagag    4200
attacaagcc tacttagggt ttaaaagaac tttatgttat cctctgatgt atgtcaatga    4260
gggtctaaat aaaaccttat ggagaaatga atgcaaaatt gagaaggttc aagcagtatt    4320
acagccatca gttccgaatg aatttaagat ttatgatgat ataatcattg ataacacgaa    4380
tggcctcttt aaggttaagt aagctgtgac tagtatcagg agttactagt caaaatcatg    4440
tgttgatatc cgaattaata gctttaagtt gaatatatta aacctgtgat aatttaaatt    4500
tgaaacataa ttagtatgta gtattgtatt aatcagttta taatcttgtt tgaggatcca    4560
aattataacc ctattaggta ttgccactcc agtcttacag gtaaatctaa gcgaatatac    4620
aaataattga tattcgggat taaacaatac ttgtatatta atccataggt atattagatt    4680
ttactatatt caattattat aatgtttatt gagttaagct ctcatgatta taaaaaacta    4740
aggattccac ataatcacag tttgattgcc aattgatgtg tttagtatta gttgtgtgaa    4800
atattgatat taataaggtt aatcaacttt tgtacagaag tgaaagtgta attagataga    4860
aatagattaa tccttagtag ccgttttgat aattgaattg attcttgttt taattctgaa    4920
ttgagattat taatcaccag ctcggcataa tgtataagat taaggttgta atcatgggtt    4980
ttttactgtt atcagatatt acatttgcac aggtaggttg ggataattta acctcaattg    5040
gagttataag tactaaacaa tataactata agataactac tttgaatact aatcaactca    5100
tggtgatcaa aatggtaccc aatatatcat caattattaa ctgtactaaa cttgaattag    5160
caaaatatag ggaactgatt acaggaatac tgagaccaat taatgaatca ttagaattga    5220
tgaattcata tatcaacatg agaacaggtt cagagagatt catagggggct gttatagcag    5280 gagtagctct aggggttgca actgcggcgc agataacatc gggaattgcc ttacataatt    5340
cgattatgaa taaaaaacag atacaggaat taaggaaagc ccttagtact acaaataagg    5400
```

```
caattgatga gataaggatt gcaggtgaaa gaactctgat agctgtccaa ggtgtgcaag      5460
attacattaa caatgttatt atccctatgc aagagaaact ccagtgcgat attttagcct      5520
cacagctatc tattgcccta ctcagatact atactaatat actgactgtt tttggaccaa      5580
gtataagaga tcctattact agtcaattt ctatacaagc tctcagtcaa gcattcaatg       5640
gtaatctaca ggcattgctt gatggattag ggtatactgg acaagactta catgatctca      5700
tagaaagtag atctatcact ggtcaaatta ttcacgctga tatgactgat ttattccttg      5760
tattgagaat caattatcca tctattacgg atatgcaagg agtggtaata tatgagctga      5820
attctatcac atatcatatt ggacctgaag agtggtacac tattatgcct aatttcatag      5880
ctgttcaggg atttctggta tctaatttcg atgaacgtaa atgttcaatt actaaaacaa      5940
gtatactgtg tcaacagaat tcaatttatc ctatgtcaac cgaaatgcaa agatgtataa      6000
aaggtgagat taaattctgt ccaaggtcca aagcaattgg gacattagtt aatcgattta      6060
tattaattaa tgggaatcta atggccaatt gtttgggtat tatctgtaga tgttataccct     6120 caggtcaaat tataacgcaa gacccaaata aattaatcac aattatatca caagaagaat      6180
gtagagaggt tggtgttgat gggattcgta taatggtggg gcctaaaaaa ttaccggatg      6240 ttatcttaa tgccagacta gaaataggtg tacctatctc attaagcaag ctggatgttg       6300
ggaccgactt ggcaattgct tcagctaaac tcaataactc taaggcactt ttggagcagt      6360
ctgataaaat cttaaattct atgtctaagt tggattcttt aaattcacgt atcttaggat      6420
ctgtctttat aattatgata atcttcgtga ctgtaattgt gattatttgg attatttgta      6480
aaaagtgtag aaataagagg aacaaattaa gtgcttctat tgaaccctc tacataccctc      6540 cctcttataa ttcaccccat agcatagtta aatctatttg aaatataagt gtataatctg      6600
atataacaga tgcagtagaa ttattaatca atgataatat tattatgata atgattcagt      6660
tagatgttca ttgtatctca taacttaata ttgacaaatt tcaattagtt aaatttattc      6720
tcttcataat atgtatttgt ttaattatcc tagattcatg tactgttatt aaattggtca     6780
tctttaataa ctaactcagc aatactatcc tatacacatg tattagctaa taacgatgta     6840
atattgccat ttaataataa gtacctagta gaatgggaag cattagctgt agtcaatgaa      6900
ccattacctg ctcaattaga aaaaacttag gaatccatgt taatgggagc tggccatcat      6960
ggaatctaat aacaacaagt actataaaga ttcaaaccgg tattttagca agatactaga      7020
tgagaacaag acggtaaata atcatctgta tagtcttagt ataaggataa ttaccgttat      7080
agctattgtt gtgagtctaa ttgcaacaac aataaccatc attaatgcta taagcggaag      7140
gactactctt aataataata tggacatgct actcaaccaa caagacaaga ttaataatat      7200
caaggaaatg atatttgatc gtatctatcc cctgataaat gccatgagta cagagcttgg      7260
tcttcacatt ccaactttat tggatgagct gactaaatca attgatcaaa aaatcaagat      7320
aatgactcca cccacttgaaa ctacaacatc taatctcaat tggtgtatca acccccaaa      7380 tggcattatt gtagatccta aaggttattg tgaaggcttg gaactgtcaa aaacttataa      7440
gttattactt gatcaattag atatgttaag aaagaaatca cttattatta ataagaaaag      7500
tattaatcag tgtagacttg ttgatagttc gaatatcgtc tttgcaacag ttaatataca      7560
atctacaccg agattcttaa atcttggtca cacagttagt aaccaacgta taacattcgg      7620
tcaaggaaca tatagtagca cttatattat aactatacaa gaggatggat taactgatgt      7680
tcagtaccga gtatttgaaa taggatatat ctcagatcaa tttggaacct tcccttctct      7740
aatcgtttcc agagtactac ctgtgcgaat ggtacttgga atggaatctt gtacactgac      7800
```

```
cagtgacaag tttgggggtt attttttatg catgaacatt ccgacacgct ctatatatga    7860
ttatgtcaac ataagagact taaagtcact atacgtcaca atccctcatt atggcaaaat    7920
taattacact tactttaatt ttgggaaagt cagaagccca catgaaattg ataagatttg    7980
gcttacatca gaaagggggac agatgatttc aggttacttt gcagcatttg ttacgattac   8040
aattagaaat tataacaatt atccctataa atgcttacat aacccgtgtc ttgaaagatc    8100
tgagagttat tgcaaaggat ggtacaaaaa tattacaggt actgatgatg ttccaatatt    8160
agcatatcta ttagttgaaa tgaatgatga ggaaggaccc ttaattacat tggttgagat    8220
accaccttac aattatacgg ctccttctca taattccctt tactatgatg ataaaattaa    8280
caaattaata atgacaacat ctcatatagg atacattcaa atcaatgaag tgcatgaagt    8340
cattgtcggg gataatctta aggctattct cttaaacaga ttatctgatg aacaccctac    8400
tcttactgct tgtagattta atcaggaaat taaagagcga catatatctg atggattaat    8460
aatatctaac tctgctctta ttgatataca agaacgtatg tatgttacag ttaaggctgt    8520
tccacccata ggaaattata acttcacggt agagttgcat tcacggtcaa atacatctta    8580
cgtagggttg ccaaggcagt tcaatgctag gtatgacaaa ctgcatctcg aatgctttgc    8640
ctgggatagg tcttggtggt gcgctttgat acctcaattt tcattaagtt ggaatgaatc    8700
tctttcagta gatactgcca tttcaactt aataaactgt aattaagttt gtggcttgtt     8760
ctagattgat catttgaata acagttgatt aagccaaagt tagtaaatac atacattaac    8820
ctgttcttga ccaagtatat atcccaatcc aattataaaa aacttaggac tcaaggtgtt    8880
gatggcaatg gagcaatcag attatcaaga tattttatat ccagaggtac atctcaacag    8940
tcctatagtt atctctaaat tagtgggtat tttggagtat tctaaggttg ttcacaatca    9000
gcagttatct gatcacacaa tagtcaagaa tatacaattt agattgagaa atggattcaa    9060
tagtccaaga atacaaacac tgttagttat gggtgaaatt atcaataaaa tcaaaaataa    9120 atcccaaat tatttgcaca taccttatcc tgaatgtaat caaaagttat ttaggatagc     9180
tgacccggag ttaacatcta aactagaagc cctcttggac aaaggtgaca cattatatct    9240
taagattaag acagagatca tagcttgttt cgataagtta aaaactaaaa tgagcataac    9300
caatgatctg attagtgaca ataggcagct aatttcagat ctacctataa ttgtcaaggg    9360
atctcaatgg ttttcccctt ttttgctctg gttctctgtt aaaactgaga ctaggaactg    9420
tattcgacaa aatcaaaaaa ctcgtgttag gtcacaatac cgacctcatt tgtcagaaac    9480
taaaagaatt acgctggtcg ttactcatga cttgatcaca atatttgacc acgtcaacaa    9540
atgtatatat catctgactt ttgagatgtt gttgatgtat tgtgatgtag tagaagggag    9600
gttaatgacc gaagcatcta tgagtctaga tcacagattt attaacctat tgtcgagggt    9660
ccagtatatg tgggatctat tagatgggat gtttgagagt ctaggaaatc agctatattc    9720
aatcattgca ctcttagaac ctctctctct tgcctatcta cagttgatgg atgcagaccc    9780
acagatacgg ggtacatttt tacaccattg cctttcagag ttggaagaac tcttatttag    9840
taaattccct tttgatcctg taatttatga aaatctaatt agtggacttg attacatcta    9900
tttaacagac gatattcatt taactgctga gatattttct ttctttagaa gttttggtca    9960 tccttatttta gaagcacaaa atgcagctag caatgttagg aaatatatga atcaacctaa   10020
agttatctca taccagactc taatgcaagg acatgcaatt ttttgtggca ttataataaa    10080
tgggttcaga gatcgtcacg gagggacatg gccacccgta gagctaccac atcatgcatc    10140
```

```
cgctgtaatt agaaatgctc agttatctgg agaaggatta cacctgagc agtgtgctca    10200
atactggagg tcattttgtg gatttaaatt taaatgtttt atgccattaa gtttagatag    10260
cgacctcacc atgtacctta gagacaaggc attatcacct attaagaatg agtgggactc    10320
tgtgtatgct aaagagtatt taagatacaa ccctggctta ccgactagct ctcgaagatt    10380
agtcaatgta tttcttgaag atgataaatt tgatccgtac gaaatgatta tgtacgtaat    10440
aaacggtgat tatttaaggg ataatgagtt caatctctca tatagtctta agaaaaagga    10500
gatcaaggag gtaggccgat tgttcgctaa aatgacttat aaaatgagag cttgtcaggt    10560
aatagcagaa aatttaattg caaatggagt tgggaaattt tttaaagaca atgggatggc    10620
gaaggatgaa cataaattaa ccaaaacatt acataagctg gccatttctg gtgtacctaa    10680
agataatttt caactctatt taagtgaatg ttgggaacaa gtggtagaac aatgcgtaac    10740
cagtacgcaa acaaaaaatc aaattatcag ttcacactca agaaaatcag ttgcatcaaa    10800
gtttccaaga tcaaatccca atgataggg tattctaaat agtggcagac atttgaataa    10860
acatccaaaa catccttcaa acaccgaata ctatgaaact gtcagtagtt ttataactac    10920
tgatctcaag aaatattgcc tcaactggcg ctatgaatca agtagtgtgt ttgcagaaag    10980
actcaatgag atttatgggt taccaggatt ttttcattgg cttcatagaa ttttggaaa     11040
atctgtatta tatgttagtg atccatccag tccacctgat tttgatcaac atgttgatat    11100
tgattcagtt ccaaatgatc atattttat caaatacca atgggtggga tagaaggatt      11160
ttgtcaaaaa ttatggacaa tcagcacaat cccattttta tatttagcag cttttgatac    11220
aggggttaga atatcttcgt tggttcaagg tgataatcaa gcaattgcag tgaccaaaag    11280
agttccatcg tcctggagtt attcgagaaa aaagaggag tcaactaaag ttacaacaca     11340
atatttttta aacttaagac aacgcttaca tgatataggt catgagttaa aggcaaatga    11400
gactattata tcttcacact ttttgttta ctctaagggt atttattatg atggtatact     11460
tctttcacaa tcccttaaaa gtattgcaag atgtgttttt tggtccgaga caattgtcga    11520
tgagactagg tcagcttgca gcaatatatc cactacccct gctaaagcta ttgaacgggg    11580
ttatgataaa ttcgtggcat acgctattaa tatatataag actatacacc aggtcttaat    11640
tgcattatct tttactatta atcccactat gactccggac ataacagaac ctttttataa    11700
aagtttagat ttacttaaaa acctcattct gataccagca ccattgggtg ggatgaatta    11760
catgaatatg agcagattat tgttagaaa cataggtgat cccattacag cttcatttgc    11820
tgacatcaag cgtatgatcg aatgcgggtt attagggcac aatgttctct cacaaataat    11880
gtatcagaaa tgtggtacct cgaaatactt agattgggct agtgacccct tattccataaa   11940
tcttccttat agtcaaagca tgaccaaagt attaaaaaat ataaccgcga gatatgttct    12000
catgcacagt cctaacccta gctaaaaga tttattccat gagaagtcac aagaagaaga    12060
tgagattctt gctgaatttt tgctggatcg tcagttaata atcccctagag ctgcacatga   12120
aattttatcg aattcagtaa caggagctag agagtcgatt gcaggatgc ttgatactac     12180
taaaggactt attcgagcca gtatgtcaag aggtggtctg acatcttcac ttgtgttgaa    12240
attgtcaaca tatgattatc aacaattag aacatgcctt gaatggcttt atgccctac      12300
cacaggaata gcagtaagtg ctgattcttg ttcagttttt ttagccagag ctattcgaaa    12360
aaggatgtgg gttcacctga ctaaaggaag agaaatttat ggcctagaag tgcctgatat    12420
attagaatgt atgcagagca atgtaattgt tgatcatgaa gattgttatt catgtattca    12480
aggatcaaga tactacacat ggtttttgt accttctaat tgtcagcttg atcagattaa    12540
```

```
caagtctaca aattctctac gggttcctta cattggctct actacagagg aaagaagtga   12600
catgaaatta tcatacgtca gatccctag taggccactt aaggcagcag tccgaattgc    12660
agcagtctac acatgggcat acggtgatga cgatctgtct tggcgtgagg cttggtactt   12720
ggcaaggact agggcaaatg ttactttcga tgagcttaaa ttagtaacac ccatagctac   12780
ctctacgaac ttggcacata gattaaggga caggagtact caagttaagt attcaggaac   12840
ttcattagta agagtggcac gctatacaac aatatccaat gataatatgt catttgtcat   12900
taatgacaaa aaggtagata ctaattttgt ctatcaacag gcatgttat tgggtttgag    12960 tatcctagaa tatatattta gatactgtaa aagtactggt caatcaaata ctgtagttca   13020
cttgcatgca gatgttaatt gttgcataat ccaaatgaca gatcaacctt atactccaag   13080
cttaacgaaa aaattacctg agattaaacc tattaataat aagttgattt atgatccagc   13140
tcctataatt gatactgatg cagctaggtt atattctcag aagtacttat cacacctgat   13200
agattttcca aattggtcaa tgaatcagct aaatgtagtt ttagcaaaag tagttgcaat   13260
atctattgtg gacttgataa ctaaagcgag taaagatcat ctcaatgaaa ttatggcagt   13320
tgttggagat gatgacatta atagctttat aacagaattt ttgctagttg atccgaggct   13380
atttacattg tacttaggtc aatacacgtc acttcaatgg gcatatgaaa ttcattatca   13440
ccgacccgta ggcaaatacc agatggcaga agtgttacac actttactgt caagagcaag   13500
taaaggtata tttaatatat taactaatgc ttttagtcat cctagagttt acaaaagatt   13560
ttgggaatgt ggattactgg agcctattta tggaccatac atagggagcc aaaatttata   13620
tagtacagta attgattacc tttacaatgc ttatataact tatttagatg cttatctatc   13680
tgatcatatc gaagatgcag acatagtaat atgtgagaca gaagaaactt gtctagctaa   13740
taggattgat aactatcaag gtaggcatct agccgtactt attgatcttt attgtgattc   13800
tactaggtgt cctaatataa aagggtcaga cacaatcatg cgaaactcaa ttctcaaatc   13860
ttttattgat aatgagagaa ggacaagtcc attaggtcta acatggaatc ttgatccatt   13920
actcatagat catttcagtt gttcaattac ttatctgagg agaggtatta ttaaacagat   13980
taggctaagg tttgatccaa acatatctat tgagttggtt aaattggcaa aacctgaagt   14040
gattcatcaa ggaccaaaaa taccgtcttc ttgggccctt atagatatta tcctgaggt    14100 caatgatctt aatacagttt tcggagaatt aaatagtaaa tggaaagata ttcctattgg   14160
acaaattaga attcaaaatt atgagatcca tgcttaccga agaattggag ttaattcaac   14220
tgcatgttat aaagcattgg aaatgctatc tgtactaacc cggtttatgt ctaacccagc   14280
aggagctttg tttttaggag agggtgcagg gtcaatgtta gttacctatc gtgcgtttat   14340
cccgttcaag agaatttatt ataatagtgg aatttctata caaatattc aaagccaaag    14400 agaactaagt ctatacccat ctgaagtagc cttggttgat aataaaatc gtttgaccag    14460 tgatcctgat atcaaagtct tatttaatgg caagccagaa tccacgtggg ttgggaatat   14520
agactgcttt gcttatattc tgagtcatat tgaaacttct agtttaacat taatccacag   14580
tgatattgaa tctagcttga gtaaaacaaa gaataagatt cttgaggagc tttgccatat   14640
tctatcaatg gcactgattt taggaaagat tggatctgta ttagttatta agctgttacc   14700
acgggttggt gactacacat attcattttg caagtatgcg tcagaattct accaacagaa   14760
tttttttatt ttacctagat ttagcaacat gtcatcatct gaaattact acgttggagt    14820 tcatttaaat accaatagac tggttgatcc agataggatt gtgcaatata taatcaggaa   14880
```

-continued

```
tctccaatct actccagtta ctttcttatc ttacattttg gaaactaaat atagaaataa      14940
tatggttaca aattatgggc tctgcttgtc tgatggacat aaaagcgatt acttgtcatc      15000
aatcaccaag atagaaaatg ttcttttatc atgtggattg gaattgaatg gacctaagat      15060
tatacagcaa ttatctggac atgactacgc caatggagag attagcttag aatcaagtat      15120
aatggtactg gttagagaat atctaaatgc aactatccaa ggtcgggaaa cactaggtct      15180
tttttcacct taccctgtgt tacatgagag tcagttaaga gaaattaaca ggtgcattgc      15240
attgaagtat gttgtatatt tacttttta ctcaacctct gtaggatcta gtagacaaat      15300
catgagcaat ctcagaaaag gagtattaat gtatgactta agagatgagt ttttcatgga      15360
aaggttatca acaaatttca agaaaaaaat aatgtcacaa gaggttaaaa ctacatggat      15420
ctttaatatt gatgtaccaa caagaaaagc tctgtataaa ttagttggtt attcacttat      15480
cattaatcac gtataacaag tgtattgagt tggtaatatt ctagatgaac aagtataggt      15540
ttatgtacag taagtgatta aatattagat tcaggtagat aaacttccta atagtgtatc      15600
ctatagataa cctaaggcta tttaatgtta gattaattag aaaaaaactc ttgaattatg      15660
atagacttca accctggct aagacttatc atttaaaatt ataaccaagt tgtcctgata      15720
atatcagatc tcattaatta cttgatagcg taatataaca ggtgcatgat gatccttat       15780 tactcatata cctgttatta agctcctgtt caaattatcc cctatttaag ttgccttta        15840 aattacctaa tatgttttgt aatgagaaac attgatacat acaaagctaa agaagcctga     15900
ttttatctaa ggttgtatct aattgttgtc aatttataat tcggaatatc tgggccctaa      15960
acctcctcca aatatactaa aaggttttaa aaaaacaaaa aaggtttctt acttattgta      16020
cggacctata gctttctttt gtctggt                                         16047
```

<210> SEQ ID NO 2
<211> LENGTH: 519
<212> TYPE: PRT
<213> ORGANISM: Feline Paramyxovirus-Type 2
<220> FEATURE:
<223> OTHER INFORMATION: Nucleocapsid protein, Strain Gordon

<400> SEQUENCE: 2

```
Met Ala Ser Leu Leu Arg Ser Leu Ala Ala Phe Lys Lys His Arg Glu
1               5                   10                  15

Gln Pro Thr Val Pro Ser Gly Ser Gly Gly Thr Ile Lys Gly Leu Lys
            20                  25                  30

Asn Thr Ile Ile Val Pro Val Pro Gly Asp Thr Val Ile Thr Thr Arg
        35                  40                  45

Ser Asn Leu Leu Phe Arg Leu Val Tyr Ile Ile Gly Asn Pro Asp Thr
    50                  55                  60

Pro Leu Ser Thr Ser Thr Gly Ala Ile Ile Ser Leu Leu Thr Leu Phe
65                  70                  75                  80

Val Glu Ser Pro Gly Gln Leu Ile Gln Arg Ile Ala Asp Asp Pro Asp
                85                  90                  95

Ala Val Phe Lys Leu Val Glu Val Val Pro Glu Val Gly Asn Pro Gly
            100                 105                 110

Glu Leu Thr Phe Ala Ser Arg Gly Ile Asn Leu Asp Lys Gln Ala Gln
        115                 120                 125

Gln Tyr Phe Arg Leu Ala Glu Lys Asn Asp Gln Gly Tyr Tyr Val Ser
    130                 135                 140

Leu Gly Phe Glu Asn Pro Pro Asn Asp Asp Asp Ile Thr Ser Ser Pro
145                 150                 155                 160
```

Glu Ile Phe Asn Tyr Ile Leu Ala Ser Val Leu Ala Gln Ile Trp Ile
                165                 170                 175

Leu Leu Ala Lys Ala Val Thr Ala Pro Asp Thr Ala Ala Glu Ala Glu
            180                 185                 190

Asn Arg Arg Trp Ile Lys Leu Met Gln Gln Arg Arg Val Asp Gly Glu
        195                 200                 205

Leu Arg Leu Ser Lys Gly Trp Leu Asp Leu Val Arg Asn Lys Ile Ala
    210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
            260                 265                 270

Ile Lys Phe Gly Ile Glu Thr Arg Tyr Pro Ala Leu Ala Leu His Glu
        275                 280                 285

Phe Ser Gly Glu Leu Ala Thr Ile Glu Gly Leu Met Lys Leu Tyr Gln
    290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Ser Gly Leu Asn Phe
            340                 345                 350

Thr Arg Ser Phe Phe Asp Pro Thr Tyr Phe Arg Leu Gly Gln Glu Met
        355                 360                 365

Val Arg Arg Ser Ser Gly Met Val Asn Ser Ser Phe Ala Lys Glu Leu
    370                 375                 380

Gly Leu Ser Glu His Glu Thr Gln Leu Val Ser Gln Ile Ile Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Ala Lys Asp Asn Ile Thr Asp Arg Ser Glu Asp
            420                 425                 430

Pro Leu Ile Ala Ile Pro Gly Ser Ser Gly Gln Pro Leu Pro Gly Tyr
        435                 440                 445

Asp Pro Asn Ile Ser Gly Asp Ser Tyr Arg Ile Asp Ser Ser Thr Lys
    450                 455                 460

Asp Thr Asn Asn Ile Ser Asp Gly Gly Thr Asn Pro Ser His Asp Val
465                 470                 475                 480

Ser Asn Ser Ala Met Glu Glu Leu Arg Arg Leu Val Glu Ser Thr Asn
                485                 490                 495

Lys Ile Asp Thr Lys Lys Ser Glu Ser Pro Gly Ile Val Asn His Tyr
            500                 505                 510

Asn Asp Thr Asp Leu Leu Arg
        515

<210> SEQ ID NO 3
<211> LENGTH: 491
<212> TYPE: PRT
<213> ORGANISM: Feline Paramyxovirus-Type 2
<220> FEATURE:
<223> OTHER INFORMATION: Phospho

```
Met Ser Ala Glu Gln Ile Gln Val Arg His Gly Leu Glu Ser Leu
1               5                   10                  15

Gln Glu Ile Lys Asn Asn Pro Pro Ser Gln Asp Val Asn Leu Ala
            20                  25                  30

Arg Glu Ile Tyr Glu Ser Ile Lys Gln Thr Gly Thr Pro Ser Thr Gln
        35                  40                  45

Gly Gly Thr Ile Thr Gly Asn Asn Thr Ala Ser Gly Cys Asp Asn Tyr
50                  55                  60

Ser Met His Ser Gln Gly Ser Gly Pro Ser Val Ser Gly Ala Asp Lys
65                  70                  75                  80

Asn Ile Glu Arg Leu Thr Gly Pro Asp Tyr Ser Glu Leu Trp Asp Pro
                85                  90                  95

Glu Gly Asn Leu Cys Met Leu Phe Glu Ser Asp Asp Asp Asn Asn
            100                 105                 110

Tyr Ser Glu Ile Asn Gly Arg Ser Thr Ala Ile Glu Gly Leu Asp Glu
        115                 120                 125

Gln Asn Asn Lys Asp Pro Gly Ile Lys Gln Ser Gly Asp Gln Cys Ser
    130                 135                 140

Glu Gly Val Ser Lys Ile Asn Ser Ser Ser Pro Gln Glu Ala Thr
145                 150                 155                 160

Leu Ser Ser Gly Arg Ser Asp Ile Ser Gly Thr Gly Val Ser Pro Cys
                165                 170                 175

Ala Ser Leu Asp Ile Thr Val Asn Glu Leu Glu Asp Ala Thr Val Lys
            180                 185                 190

Asn Ser Asn Asn Met Lys Gly Asn Trp Pro Ile Pro Lys Leu Leu Val
        195                 200                 205

Lys Pro Pro Pro Arg Met Lys Ser Leu Ser Asp Ser Val Thr Pro Leu
    210                 215                 220

Lys Gly Ala Thr Asp Gly Lys Ser Val Leu Pro Gly Met Glu Ile Thr
225                 230                 235                 240

Leu Ser Gly Lys Asn Gly Ala Thr Leu Pro Val His Pro Phe Thr Gln
                245                 250                 255

Pro Ile Lys Asp Ser Asn Ala Asp Val Ser Asn Val Arg Gln His Val
            260                 265                 270

Pro Ser Val Thr Asp Gly His Ser Asp Asp Asn Glu Glu Val Pro Gly
        275                 280                 285

Leu His Lys Glu Thr Ile Asp Lys Ala Asp Leu Ser Met Gln Asp Ile
    290                 295                 300

Tyr Asn Leu Ile Leu Gly Phe Lys Asp Asp Tyr Arg Lys Leu Ser Asn
305                 310                 315                 320

Lys Leu Asp Met Ile Leu Glu Met Lys Gln Asp Ile Asp Asn Leu Lys
                325                 330                 335

Lys Ser Ser Ala Lys Ile Gln Leu Ala Leu Ser Thr Ile Glu Gly His
            340                 345                 350

Leu Ser Ser Val Met Ile Ala Ile Pro Gly Ser Gly Ile Asp Ile Asn
        355                 360                 365

Gln Asp Glu Lys Lys Asp Gln Leu Asn Ser Asp Leu Lys Pro Leu Leu
    370                 375                 380

Gly Arg Asp His Cys Arg Ala Phe Arg Glu Val Thr Asn Pro Leu Asp
385                 390                 395                 400

Glu Thr Ser Leu Thr Asn Ala Pro Thr Lys His Val Ala Lys Ile Asn
                405                 410                 415
```

-continued

```
Lys Asn Cys Thr Leu Gln Lys Ile Asn Asn Asn Glu Thr Ser Ala Ile
            420                 425                 430

Lys Phe Val Pro Asn Asp Ser His Ala Ser Ile Ser Thr Ile Lys Ser
        435                 440                 445

Ile Val Lys Ser Ser Asn Leu Asn Gln Glu Leu Lys Val Lys Leu Leu
    450                 455                 460

Thr Ile Leu Ser Gln Ile Lys Gly Val Asp Asn Ile Lys Glu Phe Tyr
465                 470                 475                 480

Glu Lys Val Met Ile Leu Ile Lys Asn Asn Asn
                485                 490

<210> SEQ ID NO 4
<211> LENGTH: 337
<212> TYPE: PRT
<213> ORGANISM: Feline Paramyxovirus-Type 2
<220> FEATURE:
<223> OTHER INFORMATION: Matrix protein, Strain Gordon

<400> SEQUENCE: 4

Met Thr Glu Ile Phe Asn Leu Asp Glu Ser Ser Trp Ser Val Lys Gly
1               5                   10                  15

Thr Leu Asp Pro Leu Thr Pro Asp Thr Tyr Pro Asp Gly Arg Leu Val
            20                  25                  30

Pro Lys Ile Arg Val Ile Asp Pro Gly Leu Gly Asp Arg Lys Ser Gly
        35                  40                  45

Gly Tyr Met Tyr Leu Leu Leu His Gly Val Ile Glu Asp Ser Glu Thr
    50                  55                  60

Val Ile Asn Pro Lys Gly Arg Ala Phe Gly Ala Phe Pro Leu Gly Val
65                  70                  75                  80

Gly Gln Ser Thr Glu Asn Pro Glu Asp Leu Phe Lys Glu Ile Leu Thr
                85                  90                  95

Leu Asn Ile Val Thr Arg Arg Thr Ala Gly Phe Asn Glu Lys Leu Val
            100                 105                 110

Tyr Tyr Asn Thr Thr Pro Leu Asn Leu Leu Thr Pro Trp Lys Lys Val
        115                 120                 125

Leu Ala Tyr Gly Ser Ile Phe Thr Ala Asn Gln Val Cys Asn Asn Thr
    130                 135                 140

Ser Ser Ile Pro Ile Asp Ile Pro Gln Lys Phe Arg Pro Val Tyr Leu
145                 150                 155                 160

Thr Val Thr Lys Leu Ser Asp Asp Gly Tyr Tyr Gln Ile Pro Lys Met
                165                 170                 175

Ile Gln Asp Phe Lys Ser Ser Asn Ser Val Ala Phe Asn Ile Leu Val
            180                 185                 190

His Leu Ser Met Gly Thr Ile Leu Leu Asp Ser Ser Lys Gly Ser Arg
        195                 200                 205

Val Gly Asn Pro Ala Glu Asn Leu Ile Thr Phe Met Ile His Ile Gly
    210                 215                 220

Asn Phe Lys Arg Lys Asn Asn Lys Ala Tyr Ser Pro Glu Tyr Cys Lys
225                 230                 235                 240

Arg Lys Ile Met Arg Leu Gly Leu Ile Phe Ser Leu Gly Ala Ile Gly
                245                 250                 255

Gly Thr Ser Leu His Ile Arg Cys Thr Gly Lys Met Ser Lys Arg Leu
            260                 265                 270

Gln Ala Tyr Leu Gly Phe Lys Arg Thr Leu Cys Tyr Pro Leu Met Tyr
        275                 280                 285
```

```
Val Asn Glu Gly Leu Asn Lys Thr Leu Trp Arg Asn Glu Cys Lys Ile
290                 295                 300
Glu Lys Val Gln Ala Val Leu Gln Pro Ser Val Pro Asn Glu Phe Lys
305                 310                 315                 320
Ile Tyr Asp Asp Ile Ile Ile Asp Asn Thr Asn Gly Leu Phe Lys Val
                325                 330                 335
Lys
```

<210> SEQ ID NO 5
<211> LENGTH: 541
<212> TYPE: PRT
<213> ORGANISM: Feline Paramyxovirus-Type 2
<220> FEATURE:
<223> OTHER INFORMATION: Fusion protein, Strain Gordon

<400> SEQUENCE: 5

```
Met Tyr Lys Ile Lys Val Val Ile Met Gly Phe Leu Leu Leu Ser Asp
1               5                   10                  15
Ile Thr Phe Ala Gln Val Gly Trp Asp Asn Leu Thr Ser Ile Gly Val
                20                  25                  30
Ile Ser Thr Lys Gln Tyr Asn Tyr Lys Ile Thr Thr Leu Asn Thr Asn
                35                  40                  45
Gln Leu Met Val Ile Lys Met Val Pro Asn Ile Ser Ser Ile Ile Asn
50                  55                  60
Cys Thr Lys Leu Glu Leu Ala Lys Tyr Arg Glu Leu Ile Thr Gly Ile
65                  70                  75                  80
Leu Arg Pro Ile Asn Glu Ser Leu Glu Leu Met Asn Ser Tyr Ile Asn
                85                  90                  95
Met Arg Thr Gly Ser Glu Arg Phe Ile Gly Ala Val Ile Ala Gly Val
                100                 105                 110
Ala Leu Gly Val Ala Thr Ala Ala Gln Ile Thr Ser Gly Ile Ala Leu
                115                 120                 125
His Asn Ser Ile Met Asn Lys Lys Gln Ile Gln Glu Leu Arg Lys Ala
                130                 135                 140
Leu Ser Thr Thr Asn Lys Ala Ile Asp Glu Ile Arg Ile Ala Gly Glu
145                 150                 155                 160
Arg Thr Leu Ile Ala Val Gln Gly Val Gln Asp Tyr Ile Asn Asn Val
                165                 170                 175
Ile Ile Pro Met Gln Glu Lys Leu Gln Cys Asp Ile Leu Ala Ser Gln
                180                 185                 190
Leu Ser Ile Ala Leu Leu Arg Tyr Tyr Thr Asn Ile Leu Thr Val Phe
                195                 200                 205
Gly Pro Ser Ile Arg Asp Pro Ile Thr Ser Thr Ile Ser Ile Gln Ala
                210                 215                 220
Leu Ser Gln Ala Phe Asn Gly Asn Leu Gln Ala Leu Leu Asp Gly Leu
225                 230                 235                 240
Gly Tyr Thr Gly Gln Asp Leu His Asp Leu Ile Glu Ser Arg Ser Ile
                245                 250                 255
Thr Gly Gln Ile Ile His Ala Asp Met Thr Asp Leu Phe Leu Val Leu
                260                 265                 270
Arg Ile Asn Tyr Pro Ser Ile Thr Asp Met Gln Gly Val Val Ile Tyr
                275                 280                 285
Glu Leu Asn Ser Ile Thr Tyr His Ile Gly Pro Glu Glu Trp Tyr Thr
                290                 295                 300
Ile Met Pro Asn Phe Ile Ala Val Gln Gly Phe Leu Val Ser Asn Phe
```

```
305                 310                 315                 320

Asp Glu Arg Lys Cys Ser Ile Thr Lys Thr Ser Ile Leu Cys Gln Gln
                325                 330                 335

Asn Ser Ile Tyr Pro Met Ser Thr Glu Met Gln Arg Cys Ile Lys Gly
            340                 345                 350

Glu Ile Lys Phe Cys Pro Arg Ser Lys Ala Ile Gly Thr Leu Val Asn
        355                 360                 365

Arg Phe Ile Leu Ile Asn Gly Asn Leu Met Ala Asn Cys Leu Gly Ile
    370                 375                 380

Ile Cys Arg Cys Tyr Thr Ser Gly Gln Ile Ile Thr Gln Asp Pro Asn
385                 390                 395                 400

Lys Leu Ile Thr Ile Ile Ser Gln Glu Glu Cys Arg Glu Val Gly Val
                405                 410                 415

Asp Gly Ile Arg Ile Met Val Gly Pro Lys Lys Leu Pro Asp Val Ile
            420                 425                 430

Phe Asn Ala Arg Leu Glu Ile Gly Val Pro Ile Ser Leu Ser Lys Leu
        435                 440                 445

Asp Val Gly Thr Asp Leu Ala Ile Ala Ser Ala Lys Leu Asn Asn Ser
    450                 455                 460

Lys Ala Leu Leu Glu Gln Ser Asp Lys Ile Leu Asn Ser Met Ser Lys
465                 470                 475                 480

Leu Asp Ser Leu Asn Ser Arg Ile Leu Gly Ser Val Phe Ile Ile Met
                485                 490                 495

Ile Ile Phe Val Thr Val Ile Val Ile Ile Trp Ile Ile Cys Lys Lys
            500                 505                 510

Cys Arg Asn Lys Arg Asn Lys Leu Ser Ala Ser Ile Glu Pro Leu Tyr
        515                 520                 525

Ile Pro Pro Ser Tyr Asn Ser Pro His Ser Ile Val Lys
    530                 535                 540

<210> SEQ ID NO 6
<211> LENGTH: 595
<212> TYPE: PRT
<213> ORGANISM: Feline Paramyxovirus-Type 2
<220> FEATURE:
<223> OTHER INFORMATION: Hemagglutinin, Strain Gordon

<400> SEQUENCE: 6

Met Glu Ser Asn Asn Asn Lys Tyr Tyr Lys Asp Ser Asn Arg Tyr Phe
1               5                   10                  15

Ser Lys Ile Leu Asp Glu Asn Lys Thr Val Asn Asn His Leu Tyr Ser
            20                  25                  30

Leu Ser Ile Arg Ile Ile Thr Val Ile Ala Ile Val Val Ser Leu Ile
        35                  40                  45

Ala Thr Thr Ile Thr Ile Ile Asn Ala Ile Ser Gly Arg Thr Thr Leu
    50                  55                  60

Asn Asn Asn Met Asp Met Leu Leu Asn Gln Gln Asp Lys Ile Asn Asn
65                  70                  75                  80

Ile Lys Glu Met Ile Phe Asp Arg Ile Tyr Pro Leu Ile Asn Ala Met
                85                  90                  95

Ser Thr Glu Leu Gly Leu His Ile Pro Thr Leu Leu Asp Glu Leu Thr
            100                 105                 110

Lys Ser Ile Asp Gln Lys Ile Lys Ile Met Thr Pro Pro Leu Glu Thr
        115                 120                 125

Thr Thr Ser Asn Leu Asn Trp Cys Ile Asn Pro Pro Asn Gly Ile Ile
```

-continued

```
            130                 135                 140
Val Asp Pro Lys Gly Tyr Cys Glu Gly Leu Glu Leu Ser Lys Thr Tyr
145                 150                 155                 160

Lys Leu Leu Leu Asp Gln Leu Asp Met Leu Arg Lys Lys Ser Leu Ile
                165                 170                 175

Ile Asn Lys Lys Ser Ile Asn Gln Cys Arg Leu Val Asp Ser Ser Asn
                180                 185                 190

Ile Val Phe Ala Thr Val Asn Ile Gln Ser Thr Pro Arg Phe Leu Asn
                195                 200                 205

Leu Gly His Thr Val Ser Asn Gln Arg Ile Thr Phe Gly Gln Gly Thr
            210                 215                 220

Tyr Ser Ser Thr Tyr Ile Ile Thr Ile Gln Glu Asp Gly Leu Thr Asp
225                 230                 235                 240

Val Gln Tyr Arg Val Phe Glu Ile Gly Tyr Ile Ser Asp Gln Phe Gly
                245                 250                 255

Thr Phe Pro Ser Leu Ile Val Ser Arg Val Leu Pro Val Arg Met Val
                260                 265                 270

Leu Gly Met Glu Ser Cys Thr Leu Thr Ser Asp Lys Phe Gly Gly Tyr
            275                 280                 285

Phe Leu Cys Met Asn Ile Pro Thr Arg Ser Ile Tyr Asp Tyr Val Asn
            290                 295                 300

Ile Arg Asp Leu Lys Ser Leu Tyr Val Thr Ile Pro His Tyr Gly Lys
305                 310                 315                 320

Ile Asn Tyr Thr Tyr Phe Asn Phe Gly Lys Val Arg Ser Pro His Glu
                325                 330                 335

Ile Asp Lys Ile Trp Leu Thr Ser Glu Arg Gly Gln Met Ile Ser Gly
                340                 345                 350

Tyr Phe Ala Ala Phe Val Thr Ile Thr Ile Arg Asn Tyr Asn Asn Tyr
            355                 360                 365

Pro Tyr Lys Cys Leu His Asn Pro Cys Leu Glu Arg Ser Glu Ser Tyr
            370                 375                 380

Cys Lys Gly Trp Tyr Lys Asn Ile Thr Gly Thr Asp Val Pro Ile
385                 390                 395                 400

Leu Ala Tyr Leu Leu Val Glu Met Asn Asp Glu Gly Pro Leu Ile
                405                 410                 415

Thr Leu Val Glu Ile Pro Pro Tyr Asn Tyr Thr Ala Pro Ser His Asn
                420                 425                 430

Ser Leu Tyr Tyr Asp Asp Lys Ile Asn Lys Leu Ile Met Thr Thr Ser
            435                 440                 445

His Ile Gly Tyr Ile Gln Ile Asn Glu Val His Glu Val Ile Val Gly
            450                 455                 460

Asp Asn Leu Lys Ala Ile Leu Leu Asn Arg Leu Ser Asp Glu His Pro
465                 470                 475                 480

Thr Leu Thr Ala Cys Arg Phe Asn Gln Glu Ile Lys Glu Arg His Ile
                485                 490                 495

Ser Asp Gly Leu Ile Ile Ser Asn Ser Ala Leu Ile Asp Ile Gln Glu
                500                 505                 510

Arg Met Tyr Val Thr Val Lys Ala Val Pro Ile Gly Asn Tyr Asn
                515                 520                 525

Phe Thr Val Glu Leu His Ser Arg Ser Asn Thr Ser Tyr Val Gly Leu
            530                 535                 540

Pro Arg Gln Phe Asn Ala Arg Tyr Asp Lys Leu His Leu Glu Cys Phe
545                 550                 555                 560
```

```
Ala Trp Asp Arg Ser Trp Trp Cys Ala Leu Ile Pro Gln Phe Ser Leu
                565                 570                 575

Ser Trp Asn Glu Ser Leu Ser Val Asp Thr Ala Ile Phe Asn Leu Ile
            580                 585                 590

Asn Cys Asn
        595
```

<210> SEQ ID NO 7
<211> LENGTH: 2202
<212> TYPE: PRT
<213> ORGANISM: Feline Paramyxovirus-Type 2
<220> FEATURE:
<223> OTHER INFORMATION: Polymerase, Strain Gordon

<400> SEQUENCE: 7

```
Met Glu Gln Ser Asp Tyr Gln Asp Ile Leu Tyr Pro Glu Val His Leu
1               5                   10                  15

Asn Ser Pro Ile Val Ile Ser Lys Leu Val Gly Ile Leu Glu Tyr Ser
            20                  25                  30

Lys Val Val His Asn Gln Gln Leu Ser Asp His Thr Ile Val Lys Asn
        35                  40                  45

Ile Gln Phe Arg Leu Arg Asn Gly Phe Asn Ser Pro Arg Ile Gln Thr
    50                  55                  60

Leu Leu Val Met Gly Glu Ile Ile Asn Lys Ile Lys Asn Lys Tyr Pro
65                  70                  75                  80

Asn Tyr Leu His Ile Pro Tyr Pro Glu Cys Asn Gln Lys Leu Phe Arg
                85                  90                  95

Ile Ala Asp Pro Glu Leu Thr Ser Lys Leu Glu Ala Leu Leu Asp Lys
            100                 105                 110

Gly Asp Thr Leu Tyr Leu Lys Ile Lys Thr Glu Ile Ile Ala Cys Phe
        115                 120                 125

Asp Lys Leu Lys Thr Lys Met Ser Ile Thr Asn Asp Leu Ile Ser Asp
    130                 135                 140

Asn Arg Gln Leu Ile Ser Asp Leu Pro Ile Ile Val Lys Gly Ser Gln
145                 150                 155                 160

Trp Phe Phe Pro Phe Leu Leu Trp Phe Ser Val Lys Thr Glu Thr Arg
                165                 170                 175

Asn Cys Ile Arg Gln Asn Gln Lys Thr Arg Val Arg Ser Gln Tyr Arg
            180                 185                 190

Pro His Leu Ser Glu Thr Lys Arg Ile Thr Leu Val Val Thr His Asp
        195                 200                 205

Leu Ile Thr Ile Phe Asp His Val Asn Lys Cys Ile Tyr His Leu Thr
    210                 215                 220

Phe Glu Met Leu Leu Met Tyr Cys Asp Val Val Glu Gly Arg Leu Met
225                 230                 235                 240

Thr Glu Ala Ser Met Ser Leu Asp His Arg Phe Ile Asn Leu Leu Ser
                245                 250                 255

Arg Val Gln Tyr Met Trp Asp Leu Leu Asp Gly Met Phe Glu Ser Leu
            260                 265                 270

Gly Asn Gln Leu Tyr Ser Ile Ile Ala Leu Leu Glu Pro Leu Ser Leu
        275                 280                 285

Ala Tyr Leu Gln Leu Met Asp Ala Asp Pro Gln Ile Arg Gly Thr Phe
    290                 295                 300

Leu His His Cys Leu Ser Glu Leu Glu Glu Leu Leu Phe Ser Lys Phe
305                 310                 315                 320
```

```
Pro Phe Asp Pro Val Ile Tyr Glu Asn Leu Ile Ser Gly Leu Asp Tyr
            325                 330                 335

Ile Tyr Leu Thr Asp Asp Ile His Leu Thr Ala Glu Ile Phe Ser Phe
            340                 345                 350

Phe Arg Ser Phe Gly His Pro Tyr Leu Glu Ala Gln Asn Ala Ala Ser
            355                 360                 365

Asn Val Arg Lys Tyr Met Asn Gln Pro Lys Val Ile Ser Tyr Gln Thr
            370                 375                 380

Leu Met Gln Gly His Ala Ile Phe Cys Gly Ile Ile Asn Gly Phe
385                 390                 395                 400

Arg Asp Arg His Gly Gly Thr Trp Pro Val Glu Leu Pro His His
                405                 410                 415

Ala Ser Ala Val Ile Arg Asn Ala Gln Leu Ser Gly Glu Gly Leu Thr
            420                 425                 430

Pro Glu Gln Cys Ala Gln Tyr Trp Arg Ser Phe Cys Gly Phe Lys Phe
            435                 440                 445

Lys Cys Phe Met Pro Leu Ser Leu Asp Ser Asp Leu Thr Met Tyr Leu
            450                 455                 460

Arg Asp Lys Ala Leu Ser Pro Ile Lys Asn Glu Trp Asp Ser Val Tyr
465                 470                 475                 480

Ala Lys Glu Tyr Leu Arg Tyr Asn Pro Gly Leu Pro Thr Ser Ser Arg
                485                 490                 495

Arg Leu Val Asn Val Phe Leu Glu Asp Asp Lys Phe Asp Pro Tyr Glu
            500                 505                 510

Met Ile Met Tyr Val Ile Asn Gly Asp Tyr Leu Arg Asp Asn Glu Phe
            515                 520                 525

Asn Leu Ser Tyr Ser Leu Lys Glu Lys Glu Ile Lys Glu Val Gly Arg
            530                 535                 540

Leu Phe Ala Lys Met Thr Tyr Lys Met Arg Ala Cys Gln Val Ile Ala
545                 550                 555                 560

Glu Asn Leu Ile Ala Asn Gly Val Gly Lys Phe Phe Lys Asp Asn Gly
                565                 570                 575

Met Ala Lys Asp Glu His Lys Leu Thr Lys Thr Leu His Lys Leu Ala
            580                 585                 590

Ile Ser Gly Val Pro Lys Asp Asn Phe Gln Leu Tyr Leu Ser Glu Cys
            595                 600                 605

Trp Glu Gln Val Val Glu Gln Cys Val Thr Ser Thr Gln Thr Lys Asn
            610                 615                 620

Gln Ile Ile Ser Ser His Ser Arg Lys Ser Val Ala Ser Lys Phe Pro
625                 630                 635                 640

Arg Ser Asn Pro Asn Asp Arg Gly Ile Leu Asn Ser Gly Arg His Leu
                645                 650                 655

Asn Lys His Pro Lys His Pro Ser Asn Thr Glu Tyr Tyr Glu Thr Val
            660                 665                 670

Ser Ser Phe Ile Thr Thr Asp Leu Lys Lys Tyr Cys Leu Asn Trp Arg
            675                 680                 685

Tyr Glu Ser Ser Ser Val Phe Ala Glu Arg Leu Asn Glu Ile Tyr Gly
            690                 695                 700

Leu Pro Gly Phe Phe His Trp Leu His Arg Ile Leu Glu Lys Ser Val
705                 710                 715                 720

Leu Tyr Val Ser Asp Pro Ser Ser Pro Pro Asp Phe Asp Gln His Val
                725                 730                 735
```

-continued

Asp Ile Asp Ser Val Pro Asn Asp His Ile Phe Ile Lys Tyr Pro Met
            740                 745                 750

Gly Gly Ile Glu Gly Phe Cys Gln Lys Leu Trp Thr Ile Ser Thr Ile
        755                 760                 765

Pro Phe Leu Tyr Leu Ala Ala Phe Asp Thr Gly Val Arg Ile Ser Ser
    770                 775                 780

Leu Val Gln Gly Asp Asn Gln Ala Ile Ala Val Thr Lys Arg Val Pro
785                 790                 795                 800

Ser Ser Trp Ser Tyr Ser Arg Lys Lys Glu Glu Ser Thr Lys Val Thr
                805                 810                 815

Thr Gln Tyr Phe Leu Asn Leu Arg Gln Arg Leu His Asp Ile Gly His
            820                 825                 830

Glu Leu Lys Ala Asn Glu Thr Ile Ile Ser Ser His Phe Phe Val Tyr
        835                 840                 845

Ser Lys Gly Ile Tyr Tyr Asp Gly Ile Leu Leu Ser Gln Ser Leu Lys
    850                 855                 860

Ser Ile Ala Arg Cys Val Phe Trp Ser Glu Thr Ile Val Asp Glu Thr
865                 870                 875                 880

Arg Ser Ala Cys Ser Asn Ile Ser Thr Thr Leu Ala Lys Ala Ile Glu
                885                 890                 895

Arg Gly Tyr Asp Lys Phe Val Ala Tyr Ala Ile Asn Ile Tyr Lys Thr
            900                 905                 910

Ile His Gln Val Leu Ile Ala Leu Ser Phe Thr Ile Asn Pro Thr Met
        915                 920                 925

Thr Pro Asp Ile Thr Glu Pro Phe Tyr Lys Ser Leu Asp Leu Leu Lys
    930                 935                 940

Asn Leu Ile Leu Ile Pro Ala Pro Leu Gly Gly Met Asn Tyr Met Asn
945                 950                 955                 960

Met Ser Arg Leu Phe Val Arg Asn Ile Gly Asp Pro Ile Thr Ala Ser
                965                 970                 975

Phe Ala Asp Ile Lys Arg Met Ile Glu Cys Gly Leu Leu Gly His Asn
            980                 985                 990

Val Leu Ser Gln Ile Met Tyr Gln Lys Cys Gly Thr Ser Lys Tyr Leu
        995                 1000                1005

Asp Trp Ala Ser Asp Pro Tyr Ser Ile Asn Leu Pro Tyr Ser Gln Ser
    1010                1015                1020

Met Thr Lys Val Leu Lys Asn Ile Thr Ala Arg Tyr Val Leu Met His
1025                1030                1035                1040

Ser Pro Asn Pro Met Leu Lys Asp Leu Phe His Glu Lys Ser Gln Glu
                1045                1050                1055

Glu Asp Glu Ile Leu Ala Glu Phe Leu Leu Asp Arg Gln Leu Ile Ile
            1060                1065                1070

Pro Arg Ala Ala His Glu Ile Leu Ser Asn Ser Val Thr Gly Ala Arg
        1075                1080                1085

Glu Ser Ile Ala Gly Met Leu Asp Thr Thr Lys Gly Leu Ile Arg Ala
    1090                1095                1100

Ser Met Ser Arg Gly Gly Leu Thr Ser Ser Leu Val Leu Lys Leu Ser
1105                1110                1115                1120

Thr Tyr Asp Tyr Gln Gln Phe Arg Thr Cys Leu Glu Trp Leu Tyr Ala
                1125                1130                1135

Pro Thr Thr Gly Ile Ala Val Ser Ala Asp Ser Cys Ser Val Phe Leu
            1140                1145                1150

Ala Arg Ala Ile Arg Lys Arg Met Trp Val His Leu Thr Lys Gly Arg

-continued

```
            1155                1160                1165

Glu Ile Tyr Gly Leu Glu Val Pro Asp Ile Leu Glu Cys Met Gln Ser
        1170                1175                1180

Asn Val Ile Val Asp His Glu Asp Cys Tyr Ser Cys Ile Gln Gly Ser
1185                1190                1195                1200

Arg Tyr Tyr Thr Trp Phe Phe Val Pro Ser Asn Cys Gln Leu Asp Gln
            1205                1210                1215

Ile Asn Lys Ser Thr Asn Ser Leu Arg Val Pro Tyr Ile Gly Ser Thr
        1220                1225                1230

Thr Glu Glu Arg Ser Asp Met Lys Leu Ser Tyr Val Arg Ser Pro Ser
            1235                1240                1245

Arg Pro Leu Lys Ala Ala Val Arg Ile Ala Ala Val Tyr Thr Trp Ala
        1250                1255                1260

Tyr Gly Asp Asp Asp Leu Ser Trp Arg Glu Ala Trp Tyr Leu Ala Arg
1265                1270                1275                1280

Thr Arg Ala Asn Val Thr Phe Asp Glu Leu Lys Leu Val Thr Pro Ile
            1285                1290                1295

Ala Thr Ser Thr Asn Leu Ala His Arg Leu Arg Asp Arg Ser Thr Gln
        1300                1305                1310

Val Lys Tyr Ser Gly Thr Ser Leu Val Arg Val Ala Arg Tyr Thr Thr
        1315                1320                1325

Ile Ser Asn Asp Asn Met Ser Phe Val Ile Asn Asp Lys Lys Val Asp
        1330                1335                1340

Thr Asn Phe Val Tyr Gln Gln Gly Met Leu Leu Gly Leu Ser Ile Leu
1345                1350                1355                1360

Glu Tyr Ile Phe Arg Tyr Cys Lys Ser Thr Gly Gln Ser Asn Thr Val
            1365                1370                1375

Val His Leu His Ala Asp Val Asn Cys Cys Ile Ile Gln Met Thr Asp
        1380                1385                1390

Gln Pro Tyr Thr Pro Ser Leu Thr Lys Lys Leu Pro Glu Ile Lys Pro
        1395                1400                1405

Ile Asn Asn Lys Leu Ile Tyr Asp Pro Ala Pro Ile Ile Asp Thr Asp
        1410                1415                1420

Ala Ala Arg Leu Tyr Ser Gln Lys Tyr Leu Ser His Leu Ile Asp Phe
1425                1430                1435                1440

Pro Asn Trp Ser Met Asn Gln Leu Asn Val Val Leu Ala Lys Val Val
            1445                1450                1455

Ala Ile Ser Ile Val Asp Leu Ile Thr Lys Ala Ser Lys Asp His Leu
        1460                1465                1470

Asn Glu Ile Met Ala Val Val Gly Asp Asp Asp Ile Asn Ser Phe Ile
        1475                1480                1485

Thr Glu Phe Leu Leu Val Asp Pro Arg Leu Phe Thr Leu Tyr Leu Gly
        1490                1495                1500

Gln Tyr Thr Ser Leu Gln Trp Ala Tyr Glu Ile His Tyr His Arg Pro
1505                1510                1515                1520

Val Gly Lys Tyr Gln Met Ala Glu Val Leu His Thr Leu Leu Ser Arg
            1525                1530                1535

Ala Ser Lys Gly Ile Phe Asn Ile Leu Thr Asn Ala Phe Ser His Pro
        1540                1545                1550

Arg Val Tyr Lys Arg Phe Trp Glu Cys Gly Leu Leu Glu Pro Ile Tyr
        1555                1560                1565

Gly Pro Tyr Ile Gly Ser Gln Asn Leu Tyr Ser Thr Val Ile Asp Tyr
        1570                1575                1580
```

```
Leu Tyr Asn Ala Tyr Ile Thr Tyr Leu Asp Ala Tyr Leu Ser Asp His
1585                1590                1595                1600

Ile Glu Asp Ala Asp Ile Val Ile Cys Glu Thr Glu Thr Cys Leu
            1605                1610                1615

Ala Asn Arg Ile Asp Asn Tyr Gln Gly Arg His Leu Ala Val Leu Ile
        1620                1625                1630

Asp Leu Tyr Cys Asp Ser Thr Arg Cys Pro Asn Ile Lys Gly Ser Asp
            1635                1640                1645

Thr Ile Met Arg Asn Ser Ile Leu Lys Ser Phe Ile Asp Asn Glu Arg
        1650                1655                1660

Arg Thr Ser Pro Leu Gly Leu Thr Trp Asn Leu Asp Pro Leu Leu Ile
1665                1670                1675                1680

Asp His Phe Ser Cys Ser Ile Thr Tyr Leu Arg Arg Gly Ile Ile Lys
            1685                1690                1695

Gln Ile Arg Leu Arg Phe Asp Pro Asn Ile Ser Ile Glu Leu Val Lys
        1700                1705                1710

Leu Ala Lys Pro Glu Val Ile His Gln Gly Pro Lys Ile Pro Ser Ser
        1715                1720                1725

Trp Ala Leu Ile Asp Ile Asn Pro Glu Val Asn Asp Leu Asn Thr Val
1730                1735                1740

Phe Gly Glu Leu Asn Ser Lys Trp Lys Asp Ile Pro Ile Gly Gln Ile
1745                1750                1755                1760

Arg Ile Gln Asn Tyr Glu Ile His Ala Tyr Arg Arg Ile Gly Val Asn
            1765                1770                1775

Ser Thr Ala Cys Tyr Lys Ala Leu Glu Met Leu Ser Val Leu Thr Arg
        1780                1785                1790

Phe Met Ser Asn Pro Ala Gly Ala Leu Phe Leu Gly Glu Gly Ala Gly
        1795                1800                1805

Ser Met Leu Val Thr Tyr Arg Ala Phe Ile Pro Phe Lys Arg Ile Tyr
        1810                1815                1820

Tyr Asn Ser Gly Ile Ser Ile Gln Asn Ile Gln Ser Gln Arg Glu Leu
1825                1830                1835                1840

Ser Leu Tyr Pro Ser Glu Val Ala Leu Val Asp Asn Lys Asn Arg Leu
            1845                1850                1855

Thr Ser Asp Pro Asp Ile Lys Val Leu Phe Asn Gly Lys Pro Glu Ser
            1860                1865                1870

Thr Trp Val Gly Asn Ile Asp Cys Phe Ala Tyr Ile Leu Ser His Ile
        1875                1880                1885

Glu Thr Ser Ser Leu Thr Leu Ile His Ser Asp Ile Glu Ser Ser Leu
        1890                1895                1900

Ser Lys Thr Lys Asn Lys Ile Leu Glu Glu Leu Cys His Ile Leu Ser
1905                1910                1915                1920

Met Ala Leu Ile Leu Gly Lys Ile Gly Ser Val Leu Val Ile Lys Leu
            1925                1930                1935

Leu Pro Arg Val Gly Asp Tyr Thr Tyr Ser Phe Cys Lys Tyr Ala Ser
            1940                1945                1950

Glu Phe Tyr Gln Gln Asn Phe Phe Ile Leu Pro Arg Phe Ser Asn Met
        1955                1960                1965

Ser Ser Ser Glu Ile Tyr Tyr Val Gly Val His Leu Asn Thr Asn Arg
        1970                1975                1980

Leu Val Asp Pro Asp Arg Ile Val Gln Tyr Ile Ile Arg Asn Leu Gln
1985                1990                1995                2000
```

Ser Thr Pro Val Thr Phe Leu Ser Tyr Ile Leu Glu Thr Lys Tyr Arg
                2005                2010                2015

Asn Asn Met Val Thr Asn Tyr Gly Leu Cys Leu Ser Asp Gly His Lys
            2020                2025                2030

Ser Asp Tyr Leu Ser Ser Ile Thr Lys Ile Glu Asn Val Leu Leu Ser
        2035                2040                2045

Cys Gly Leu Glu Leu Asn Gly Pro Lys Ile Ile Gln Gln Leu Ser Gly
    2050                2055                2060

His Asp Tyr Ala Asn Gly Glu Ile Ser Leu Glu Ser Ser Ile Met Val
2065                2070                2075                2080

Leu Val Arg Glu Tyr Leu Asn Ala Thr Ile Gln Gly Arg Glu Thr Leu
                2085                2090                2095

Gly Leu Phe Ser Pro Tyr Pro Val Leu His Glu Ser Gln Leu Arg Glu
            2100                2105                2110

Ile Asn Arg Cys Ile Ala Leu Lys Tyr Val Val Tyr Leu Leu Phe Tyr
        2115                2120                2125

Ser Thr Ser Val Gly Ser Ser Arg Gln Ile Met Ser Asn Leu Arg Lys
    2130                2135                2140

Gly Val Leu Met Tyr Asp Leu Arg Asp Glu Phe Phe Met Glu Arg Leu
2145                2150                2155                2160

Ser Thr Asn Phe Lys Lys Lys Ile Met Ser Gln Glu Val Lys Thr Thr
                2165                2170                2175

Trp Ile Phe Asn Ile Asp Val Pro Thr Arg Lys Ala Leu Tyr Lys Leu
            2180                2185                2190

Val Gly Tyr Ser Leu Ile Ile Asn His Val
        2195                2200

<210> SEQ ID NO 8
<211> LENGTH: 16045
<212> TYPE: DNA
<213> ORGANISM: Feline Paramyxovirus-Type 2
<220> FEATURE:
<223> OTHER INFORMATION: complementary sequence of the genome of Feline Paramyxovirus-Type 2 (FPaV-2), Strain TV25

<400> SEQUENCE: 8

```
accagacaaa gatgtctgtg acctattcta acggttagat tattacttga tatttaggaa      60
taacgattcc attagtcagg taagggagag gaatcagtta ttctataatg gctagtttac     120
tcaggtcact tgcggcattc aagaaacaca gagaacaacc aactgttcct tctgggtcag     180
gagggacgat caaaggatta aaaaatacaa ttattgtgcc tgttcctgga gatacagtca     240
tcactaccag atcgaactta ctgttcagat tagtctacat aattggtaat ccagatacac     300
ctttaagcac ttcaacaggg gcaataatat cattgttgac attatttgtt gaatctccag     360
gtcaattaat tcaaagaatc gctgatgatc ctgatgctgt ttttaaatta gtagaggtgg     420
ttcctgaggt tggtaatcct ggagaattaa cttttgcatc tagaggaatt aacttggata     480
aacaagctca acaatacttt agattggctg agaaaaatga tcaaggatat tatgtaagtt     540
tggggtttga aaatccacca aatgatgatg atataacgtc aagtcctgaa atcttaaatt     600
atattttagc atctgtactt gcacagatct ggattctcct agctaaggct gtaactgctc     660
cagacacagg tggtgaggct gaaaatcgta ggtggattaa attgatgcaa caacgcagag     720
tggatggtga gcttagatta agtaaaggat ggttggactt agtgaggaat aaaatcgcat     780
cggatatcac aattagaagg tttatggtag cattagttct tgacattaaa cgttctcctg     840
gaacaagacc aagaattgct gaaatgattt gtgatataga caattatatt gtggaggccg     900
```

```
gactggcaag ttttctgtta actatcaaat ttggtataga aacacgttac ccagcattgg    960
cgttacatga gttttcgggg gaattagcca ctattgaagg actcatgaaa ttgtaccagt   1020
ctatgggaga aatggcacca tacatggtca ttctagagaa ttcgatccag actaggttta   1080
gtgctgggtc ttatccgtta ctctggagct atgctatggg tgttggtgta aacttgaga   1140 gatcaatgag tggattaaac ttcacaagaa gtttctttga tcctacgtac ttcaggttgg   1200
gtcaggagat ggtaagaagg tcttcaggaa tggttaatag ctcatttgct aaagaacttg   1260
gactatctga acatgaaaca caacttgtta gccagatcat taactctggt ggtgaatcag   1320
gtataccgaa atttgatgga tttagagcaa acccaacaac atttctaggg gctaaggaca   1380
acatcactga taggagtgaa gatccattga ttgcaattcc agggtcatca ggacaaccat   1440
tgccaggtca tgaccccaat atctcaggtg actcatatag aattgatagt agcactaaag   1500
acacgaacaa tatatcagat ggaggaacaa atccaagtca tgatgtttcc aattctgcta   1560
tggaagagct gagaagattg gtagagtcta ccaacaagat tgatacaaag aaatctgaaa   1620
gcccaggcat tgttaatcat tacaacgata ctgaccttct gagataataa ggatatattc   1680
aggtagatct ttacagaatt taaattaaga aaaacttagg acctcaaggt tcacactcct   1740
ctggccttca tcagaactcg gccaattcct cactcactcc atgtcagcag aacaaatcca   1800
acaagttaga catggccttg aatccttgca agagatcaaa acaaccctc cacccctctca   1860 agatgtcaat cttgccaggg aaatttacga atccattaaa caaacaggaa caccttcaac   1920
acaaggaggg accattacag gaaataatac tacgtcaggg tgtgacaatt actcaatgca   1980
tagccaggga tcaggtcctt ctgtttcagg tgctgacaag aatatcgaga gacttactgg   2040
acccgattat tcagaattat gggatccaga aggtaacctc tgcatgctat tcgaaagcga   2100
tgatgatgac aacaattatt cagagattaa tggccggtct accgctatcg aaggattgga   2160
tgaacagaat aataaggacc caggtattaa acaatcagga gatcagtgtt ctgaaggagt   2220
gtctaagatt aattcatctt ctagtcccca agaagctaca ttatcttctg ggagatctga   2280
tatatctggg acaggagtat ctccctgtgc ctctttggat ataactgtta atgaattaga   2340
agatgcaact gttaagaata gtaataatat gaaaggaaat tggccaatcc caaagttgct   2400
tgtcaaacca ccaccaagaa tgaaatcact ttctgactct gttacaccat taaaagggc   2460 caccgacggg aaatcagtct tacctgggat ggagattaca ttgtccggga agaatggtgc   2520
aaccctacct gtacacccat ttacacaacc tgtaaaagac tcaaatgcag atgtaagcaa   2580
tgtccgtcaa catgtcccaa gtgtgactga tggttatagt gatgataatg aggaagtacc   2640
cggtttgcat aaagaaacta tagacaaagc tgatctatct atgcaggaca tatacaattt   2700
aattcttgga tttaaggatg attacaggaa actatcaaat aaattggata tgatactaga   2760
gatgaaacaa gatattgata atcttaaaaa gagtagtgca aaaatacaac ttgcattatc   2820
aacaattgaa ggacatctgt ccagtgttat gattgctatt ccaggttcag gtattgatat   2880
gaatcaagat gagaagaagg atcaattaaa ctctgactta aagccattac tagggaggga   2940
ccattgccgt gcatttcgtg aagtcactaa tcctttagat gaaacgtcat tgaccaacgc   3000
tccgaccaaa catgttgcta agatcaacaa aaattgcact cttcagaaaa tcaataagaa   3060
tgagacatct gcaattaagt ttgtacctaa tgatagctat gcaagtatct cgactatcaa   3120
gtctattgtc aaatcctcaa accttaatca agagcttaaa gtcaagttac tgacaattct   3180
atctcaaatt aaaggggtag acaatattaa ggagtttttat gagaaagtta tgatattgat   3240
```

```
caagaataat aactgatctt gactaatcaa tagatactac ttatcaaatc tagctctgac    3300
atcaagtgaa ttcatcttta ttaacaagta ttaatcttaa ataattataa aaaacttagg    3360
agttcaggat cagtgggtca tatacaatat gactgagata ttcaatctgg atgaaagttc    3420
atggtcagtc aagggaacac tggacccatt gacgcctgat acttatcctg atgggcgcct    3480
agtacccaag attcgggtta ttgatcccgg tctaggtgat cgtaaaagtg aggatatat    3540 gtacttactc cttcacggtg tcatcgagga cagtgagacc gtcataaatc cgaaagggag    3600
agcatttgga gctttccctt taggtgtagg gcaatcaacc gagaacccag aagacttatt    3660
taaggaaata ttaaccctca acattgttac tcgcaggact gctggcttca atgaaaaatt    3720
ggtgtattat aatactacac ctctaaatct actaaccccct tggaaaaaag tactagcata    3780
tggaagtatc tttactgcta atcaggtctg caataataca agttctatcc ctatagacat    3840
tcctcagaaa tttcgacctg tctatttaac tgttaccaag ttatcggatg atggatatta    3900 tcagataccct aaaatgatac aggatttcaa atcatcaaac tctgttgcat ttaacatcct    3960
tgtgcatcta tcaatgggaa caattttact tgactcatct aaaggctctc gagtaggaaa    4020
tcctgcagaa aatttgatca cattcatgat tcatattggg aatttcaaac ggaagaataa    4080
taaagcttat tctcccgaat attgtaagag gaaaataatg aggcttggat taatcttctc    4140
actaggagcc attggtggaa caagtttgca tattcgatgc acaggcaaaa tgagtaagcg    4200
attacaagcc tacttagggt ttaaaagaac tttatgttat cctctgatgt atgtcaatga    4260
gggtctaaac aaaaccttat ggagaaatga atgcagaatt gagaaggttc aagcagtatt    4320
acagccatca gttccgaatg aatttaagat ttatgatgat ataatcattg ataacacgaa    4380
tggcctcttt aaggttaagt aagctgtgac tagtatcagg agttactagt caaaatcatg    4440
tgttgatatc cgaattaata gctttaagtt gaatatatta aacctgtgat aattcaaatt    4500
tgaaacataa ttagtatgta gtattgtatt aatcagtttg taatcttgtt tgaggatcca    4560
aattataacc tattaggtat tgccactcca gcttacaggt aaatctaagc gaatatacaa    4620
ataattgata ttcgggatta aacaatactt gcatattaat ccataggtat attagatttt    4680
actatattca attattataa tgtttattga gttaagctct catgattata aaaaacttag    4740
gattccacat aatcacagtt tgattgccaa ttgatgtgtt tagtattagt tgtgtgaaat    4800
attgatatta ataaggttaa tcaactttg tacagaagtg aaggtgtaat tagatagaaa    4860
tagattaatc cttagtagcc gttttgataa ttgaattgat tcttgtttta attctgaatt    4920
gagattatta atcaccagct cggcataatg tataagatta aggttgtaat catgggtttt    4980
ttactgttat cagatattac atttgcacag gtaggttggg ataatttaac ctcaattgga    5040
gttataagta ctaaacaata taactataag ataactactt tgaatactaa tcaactcatg    5100
gtgattaaaa tggtacccaa tatatcatca attattaact gtactaaact tgaattagca    5160
aaatataggg aactgattac aggaatactg agaccaatta atgaatcatt agaattgatg    5220
aattcatata tcaacatgag aacaggttca gagagattca taggggctgt tatagcagga    5280
gtagctctag gggttgcaac tgcggcgcag ataacatcgg gaattgcctt acataattcg    5340
attatgaata aaaaacagat acaggaatta aggaaagccc ttagtactac aaataaggca    5400
attgatgaga taaggattgc aggtgaaaga actctgatag ctgtccaagg tgtgcaagat    5460
tacattaaca atgttattat ccctatgcaa gagaaactcc agtgcgatat tttagcctca    5520
cagctatcta ttgccctact cagatactat actaatatac tgactgtttt tggaccaagt    5580
ataagagatc ctattactag tacaatttct atacaagctc tcagtcaagc attcaatggt    5640
```

```
aatctacagg cattgcttga tggattaggg tatactggac aagacttaca tgatctcata    5700
gaaagtagat ctatcactgg tcaaataatt cacgctgata tgactgattt attccttata    5760
ttgagaatca attatccatc tattacggat atgcaaggag tggtaatata tgagctgaat    5820
tctatcacat atcatattgg acctgaagag tggtacacta ttatgcctaa tttcatagct    5880
gttcagggat ttctggtatc taatttcgat gaacgtaaat gttcaattac taaaacaagt    5940
atactgtgtc aacagaattc aatttatcct atgtcaaccg aaatgcaaag atgtataaaa    6000
ggtgagatta aattctgtcc aaggtccaaa gcaattggga cattagttaa tcgatttata    6060
ttaattaatg ggaatctaat ggccaattgt ttgggtatta tttgtagatg ttatacctca    6120
ggtcaaatta taacgcaaga cccaaataaa ttaatcacaa ttatatcaca agaagaatgt    6180
agagaggttg gtgttgatgg gattcgtata atggtgggac ctaaaaaatt accgatgtt     6240
atctttaatg ccagactaga aataggtgta cctatctcat taagcaagct ggatgttggg    6300
accgatttgg caattgcttc agctaaactc aataactcta aggcactttt ggagcagtct    6360
gataaaatct taaattctat gtctaagttg gattctttaa attcacgtat cttaggatct    6420
gtctttataa tgatgataat cttgtgatt gtaattgtga ttatttggat tatttgtaag     6480
aagtgtagaa ataagaggaa caaattaagt gcttctattg aaccctcta catacctccc     6540
tcttataatt caccccatag catagttaaa tctatttgaa atataagtgt ataatctgat    6600
ataacagatg cagtagaatt attaatcaat gataatatta ttatgataat gattcagtta    6660
gatgttcatt atatctcata acttaatatt gacaaatttc aattagttaa atttattctc    6720
ttcataatat gtatttgttt aattatccta gattaatgta ttgttattaa actggtcatc    6780
tttaataccg aactcagcaa tactatccta tacacatgta ttagctaata acgatgtaat    6840
attgccattt aataataagt acctagtaga atgggaagca ttagctgtag tcaatgaatc    6900
attatctgct caattagaaa aaayttagga atccatgtta atgggagttg gccatcatgg    6960
agtctaataa caacaagtac tataaagatt caaaccggta ttttagcaag atactagatg    7020
agaacaagac ggtaaataat catctgtata gtcttagtat aaggataatt accgttatag    7080
ctattgttgt gagtctaatt gcaacaacaa taaccatcat taatgctata agcggaagga    7140
ctactcttaa taataatatg gacatgctac tcaaccaaca agacaagatt aataatatca    7200
aggaaatgat atttgatcgt atctatcccc tgataaatgc catgagtaca gagcttggtc    7260
ttcacattcc aactttattg gatgagctga ctaaatcaat tgatcaaaaa atcaagataa    7320
tgactccacc acttgaaact acgacatcta atctcaattg gtgtatcaac cccccaaatg    7380
gcattattgt agatcctaaa ggttactgtg aaggcttgga actgtcaaaa acttataagt    7440
tattacttga tcaattagat atgttaagaa agaaatcact tattattaat aagaaaagta    7500
ttaatcagtg tagacttgtt gatagctcga atatcatctt tgcaacagtt aatatacaat    7560
ctacaccgag attcttaaat cttggtcaca cagttagtaa ccaacgtata acattcggtc    7620
aaggaacata tagtagcact tatattataa ctatacaaga ggatggatta actgatgttc    7680
agtaccgagt atttgaaata ggatatatct cagatcaatt tggaaccttc ccttctctaa    7740
tcgtttctag agtactacct gtgcgaatgg tacttggaat ggaatcttgt acactgacca    7800
gtgacaagtt cgggggttat tttttatgca tgaacattcc gacacgctct atatatgatt    7860
atgtcaacat aagagactta aagtcactat acgtcacaat ccctcattat ggcaaaatta    7920
attacactta ctttaatttt ggaaaagtca gaagcccaca tgaaattgat aagatttggc    7980
```

```
ttacatcaga aaggggacag atgatttcag gttactttgc agcatttgtt acgattacaa    8040
ttagaaatta taacaattat ccctataaat gcttacataa cccgtgtctt gaaagatctg    8100
agagttattg caaaggatgg tacaaaaata ttacaggtac tgatgatgtt ccaatattag    8160
catatctatt agttgaaatg aaggatgagg aaggacettt aattacactg gttgaaatac    8220
caccttacaa ttatacggct ccttctcata attcccttta ctatgatgat aaaattaaca    8280
aattaataat gacaacatct catataggat acattcaaat caatgaagtg catgaagtca    8340
ttgtcgggga taatcttaag gctattctct taaacagatt atctgatgaa caccctactc    8400
ttactgcttg tagatttaat caggaaatta aagagcgaca tatatctgat gggttaataa    8460
tatctaactc tgctcttatt gatatacaag aacgtatgta tattacagtt aaggctgttc    8520
cacccatagg aaattataac ttcacggtag agttgcattc acggtcaaat acatcttacg    8580
tagggttgcc aaggcagttc aatgctaggt atgacaaact gcatctcgaa tgctttgcct    8640
gggataggtc ttggtggtgc gctttgatac ctcaattttc attaagttgg aatgaatctc    8700
tttcagtaga tactgccatt tcaacttaa taaactgtaa ttaagtttgt ggcttgttct    8760
agattgatca tttgaataac agttgattaa gccgaagtta gtaaatacat acattaacct    8820
gttcttgacc aagtatgtat cctaatccaa ttataaaaaa cttaggactc aaggtgttga    8880
tggcaatgga gcaatcagat tatcaagata ttttatatcc agaggtacat ctcaacagtc    8940
ctatagttat ctctaaatta gtgggtattt tggagtattc taaggttgtt cacaatcagc    9000
agttatctga tcacacaata gtcaagaata tacaatttag attgagaaat ggattcaata    9060
gtccaagagt acaaacactg ttagttatgg gtgaaattat caataaaatc aaaaataaat    9120
acccaaatta tttgcacata ccttatcctg aatgtaatca aaagttattt aggatggctg    9180
acccggagtt aacatctaaa ctagaagccc tcttggacaa aggtgacaca ttatatctta    9240
agattaagac agagatcata gcttgtttcg ataagttaaa aactaaaatg agcataacca    9300
atgatctgat tagtgacaat aggcagctaa tttcagatct acctctaatt gtcaagggat    9360
ctcaatggtt tttcccttttt ttgctctggt tttctgttaa aactgagact aggaactgta    9420
ttcgacaaaa tcaaaaaact cgtgttaggt cacaataccg acctcatttg tcagaaacta    9480
aaagaattac gctggtcgtt acccctgact tgatcacaat atttgaccac gtcaacaaat    9540
gtatatatca tctgactttt gagatgttgt tgatgtattg tgatgtagta aagggaggt    9600 taatgaccga agcatctatg agtctagatc acagatttat taacctattg tcgagggtcc    9660
agtatatgtg ggatctatta gatgggatgt ttgagagtct aggaaatcag ctatattcaa    9720
tcattgcact cttagaacct ctctctcttg cctatctaca gttgatggat gcagacccac    9780
agatacgggg tacatttta caccattgcc tttcagagtt ggaagaactc ttatttagta    9840
aatccccttt tgatcctgtg atttatgaaa atctaattag tggacttgat tacatctatt    9900
taacagacga tattcattta actgctgaga tattttcttt cttagaagt tttggtcatc    9960 cttatttaga agcacaaaat gcagctagca atgttaggaa atatatgaat caacctaaag    10020
ttatctcata ccagactcta atgcaaggac atgcaatttt ttgtggcatt ataataaatg    10080
ggttcagaga tcgtcacgga gggacatggc cacctgtaga gctaccacat catgcatccg    10140
ctgtaattag aaatgctcag ttatctggag aaggattaac acctgagcag tgtgctcaat    10200 actggagtc atttttgtgga tttaaattta atgttttat gccattaagt ctagatagcg    10260
acctcaccat gtaccttaga gataaggcat tatcacctat taagaatgag tgggattctg    10320
tgtatgctaa agagtatttta agatacaacc ctggcttacc gactagctct cgaagattag    10380
```

```
tcaatgtatt tctagaagat gataaatttg atccgtacga aatgattatg tacgtaataa   10440
acggtgatta tttaagggat aatgagttca atctctcata tagtcttaaa gaaaaggaga   10500
tcaaggaggt aggccgattg ttcgctaaaa tgacttataa gatgagagct tgtcaggtaa   10560
tagcagaaaa tttaattgca aatggagttg ggaaattttt taaagacaat gggatggcga   10620
aggatgaaca taaattaacc aaaacattac ataagctggc tatttctggt gtacctaaag   10680
ataattctca actctattta agtgaatgtt gggaacaagt ggtagaacaa tgcgtaacca   10740
gtacgcaaac aaaaaatcaa attatcagtt cacactcagg aaaatcagtt gcatcaaagt   10800
tttcaagatc aaatcccaat gatagggagta ttctaaatag tggtagacat ttgaataaac   10860
atccaaaaca tccatcaaac accgaatact atgaaactgt cagtagtttt ataactactg   10920
atctcaagaa atattgcctc aactggcgct atgaatcaag tagtgtgttt gcagaaagac   10980
tcaatgagat ttatgggtta ccaggatttt tccattggct tcatagaatt ttggagaaat   11040
ctgtattata tgttagtgat ccatccagtc cacctgattt tgatcaacat gtcgatattg   11100
attcagttcc aaatgatcat attttatca atacccaat gggtgggata aaggattttt   11160
gtcaaaaatt atggacaatc agcacaatcc cattttata tttagcagcc tttgatacag   11220
gggttagaat atcttcgttg gttcaaggtg ataatcaagc aattgcagtg accaaaagag   11280
ttccatcatc ctggagttat tcgagaaaaa aagaggagtc aactaaagtt acaacacaat   11340 atttttaaa cttgagacaa cgcttacatg atataggtca tgagttaaag gcaaatgaga   11400
ctattatatc ttcacacttt tttgtttact ctaagggtat ttattatgat ggtatacttc   11460
tttcacaatc ccttaaaagt attgcaagat gtgttttttg gtccgagaca attgtcgatg   11520
agactaggtc agcttgcagc aatatatcca ctacccttgc taaagctatt gaacggggtt   11580
atgataaatt tgtagcatac gctattaata tatataagac tatacaccag gtcttaattg   11640
cattatcttt tactattaat cccactatga ctccggacat aacagaacct ttttataaaa   11700
gtttagattt acttaaaaac ctcattctga taccagcacc attgggtggg atgaattaca   11760
tgaatatgag cagattattt gttaggaaca taggtgatcc cattacagct tcatttgctg   11820
acatcaagcg tatgatcgaa tgcgggttat tagggcacaa tgttctctca caaataatgt   11880
atcagaaatg tggtacctcg aaatacttag attgggctag tgacccttat tccataaatc   11940
ttccttatag tcaaagcatg accaaagtat taaaaaatat aaccgcgaga tatgttctca   12000
tgcatagtcc taaccctatg ctaaaagatt tattccatga gaagtcacaa gaagaggatg   12060
agattcttgc tgaattttg ctggatcgtc agttaataat ccctagagct gcacatgaaa   12120
ttttatcgaa ttcagtaaca ggagctagag agtcgattgc agggatgctt gatactacta   12180
aaggacttat tcgagccagt atgtcaagag gtggtctgac atcttcactt gttttgaaat   12240
tgtcaacata tgattatcaa caatttagaa catgccttga atggctttat gcccctacca   12300
caggaatagc agtaagtgct gattcttgtt cagttttttt agccagagct attcgaaaaa   12360
ggatgtgggt tcacctgact aaaggaagag aaatttatgg cctagaagtg cctgatatat   12420
tagaatgtat gcagagcaat gtaattgttg atcatgaaga ttgttattca tgtattcaag   12480
gatcaagata ctacacatgg ttttttgtac cttctaattg tcagcttgat cagattaaca   12540
agtctacaaa ttctctacgg gttccttaca ttggctctac tacagaggaa agaagtgaca   12600
tgaaattatc atacgtcaga tcccctagta ggccacttaa ggcagcagtc cgaattgcag   12660
cagtctacac atgggcatac ggtgatgacg atctgtcttg gcgtgaggct tggtacttgg   12720
```

```
caaggactag ggcaaatgtt actttcgatg agcttaaatt agtaacaccc atagctacct    12780
ctactaactt ggcacataga ttaagggaca ggagtactca agttaagtat tcaggaactt    12840
cattggtaag agtggcacgc tatacaacaa tatccaatga taatatgtca tttgttatta    12900
atgacaaaaa ggtagatact aattttgtct atcaacaggg catgttattg ggtttgagta    12960
tcctagaata tatatttaga tactgtaaaa gtactggtca atcaaatact gtagttcact    13020
tgcatgcaga tgttaattgt tgcataatcc aaatgacaga tcaaccttat actccaagct    13080
taacgaaaaa attacctgag attaaaccta ttaataataa attgatttat gatccagctc    13140
ctataattga tactgatgca gctaggttat attctcagaa gtacttatca cacctgatag    13200
attttccaaa ttggtcaatg aatcagctaa atgtagtttt agcaaaagta gttgcaatat    13260
ctattgtgga cttgataact aaagcgagta agatcatct caatgaaatt atggcagttg    13320
ttggagatga tgacattaat agctttataa cagaattttt gctagttgat ccgaggctat    13380
ttacattgta cttaggtcaa tacacgtcac ttcaatgggc atatgaaatt cattatcacc    13440
gacccgtagg caaataccag atggcagaag tgttacacac tttactgtca agagcaagta    13500
aaggtatatt taatatattg actaatgcct ttagtcatcc tagagtttac aaaagatttt    13560
gggaatgtgg attactggag cctatttatg gaccatacat agggagccaa aatttatata    13620
gtacagtaat tgattacctt tacaatgctt ataaactta tttagatgct tatctatctg    13680
atcatatcga agatgcagac atagtaatat gtgagacaga agaaacttgt ctagctaata    13740
ggattgataa ctatcaaggt aggcatctcg ccgtacttat tgatctttat tgtgattcta    13800
ctaggtgtcc taatataaaa gggtcagaca caatcatgcg aaactcaatt ctcaaatctt    13860
ttattgataa tgagagaagg acaagtccat taggtctaac atggaatctt gatccattac    13920
tcatagatca tttcagttgt tcaattactt atctgaggag aggtattatt aaacagatta    13980
ggctaaggtt tgatccaaac atatctattg agttggttaa attggcaaaa cctgaagtga    14040
ttcatcaagg accaaaaata ccgtcttctt gggccttat agatattaat cctgaggtca    14100
atgatcttaa tacagttttc ggagaattaa atagtaaatg gaaagatatt cctattggac    14160
aaattagaat tcaaaatttt gagatccatg cttaccgaag aattggagtt aattcaactg    14220
catgttataa agcattggaa atgctatctg tactaactcg gtttatgtct aacccagcag    14280
gagctttgtt tttaggagag ggtgcagggt caatgttagt tacctatcgt gcgtttatcc    14340
cgttcaagag aatttattat aatagtggag tttctataca aatattcaa agccaaaggg    14400
aactaagtct atacccatct gaagtagcct tggtcgataa taaaaatcgt ttgaccagtg    14460
atcctgatat caaagtctta tttaatggca agccagaatc cacgtgggtt gggaatatag    14520
actgctttgc ttatattctg agtcatattg aaacttctag tttaacatta atccacagtg    14580
atattgaatc tagcttgagt aaaacaaaga ataagattct tgaggagctt tgccatattc    14640
tatcaatggc actgattcta ggaaagatg gatctgtatt agttattaag ctattaccac    14700
gggttggtga ctacacatat tcattttgca agtatgcgtc agaattctac caacagaatt    14760
tcttcatttt acctagattt agtaacatgt catcatctga aatttactac gttggagttc    14820
atttaaatac caatagactg gttgatccag ataggattgt gcaatatata atcaggaatc    14880
tccaatctac tccagtcact ttcttatctt acattttgga aactaaatat agaaataata    14940
tggttacaaa ttatgggctc tgtttgtctg atggacataa aagcgattac ttgtcatcaa    15000
tcaccaagat agaaaatgtt cttttatcat gtggattgga attgaatgga cctaagatta    15060
ttcagcaatt atctggacat gactacgcca atggagagat tagcttagaa tcaagtataa    15120
```

```
tggtactggt cagagaatat ctaaatgcaa ctatccaagg tcgagaaaca ctaggtcttt  15180
tttcacctta ccctgtgtta catgagagtc agttaagaga aattaacagg tgcattgcat  15240
tgaagtatgt tgtatattta cttttttact caacctctgt aggatctagt agacagatca  15300
tgagcaatct cagaaaagga gtattaatgt atgacttaag agatgagttt ttcatggaaa  15360
ggttatcaac aaatttcaag aaaaaaataa tgtcacaaga ggttaaaact acatggatct  15420
ttaatattga tgtaccaaca agaaaagctc tgtataaatt agttggttat tcacttatca  15480
ttaatcacgt ataacaagtg tattgagttg gtaatattct agatgaacaa gtataggttt  15540
atgtacagta agtgattaaa tattagattc aggtagataa acttcctaat agtgtatcct  15600
atagataacc taaggctatt tgatgttaga ttaattagaa aaaacttctt gaattatgat  15660
agacttcaac ccctggctaa gacttatcat ttaaaattat aaccaagttg tcctgataat  15720
atcagatctc attaattact tgatagcgta atataacagg tgcatgatga tcctttatta  15780
ctcatatacc tgttattaag ctcctgttca cattatcccc tatttaagtt gccttttaaa  15840
ttacctaata tgtttagtaa tgagaaacat tgatacatac aaagctaaag aagcctgatt  15900
ttatctaagg ttgtatctaa ttgttgtcaa tttataattc ggaatatctg ggccctaaac  15960
ctcctccaaa tatactaaaa ggttttaaaa aaacaaaaaa ggtttcttac ttattgtacg  16020
gacctatagc tttcttttgt ctggt                                        16045
```

```
<210> SEQ ID NO 9
<211> LENGTH: 519
<212> TYPE: PRT
<213> ORGANISM: Feline Paramyxovirus-Type 2
<220> FEATURE:
<223> OTHER INFORMATION: Nucleocapsid protein, Strain TV25

<400> SEQUENCE: 9

Met Ala Ser Leu Leu Arg Ser Leu Ala Ala Phe Lys Lys His Arg Glu
1               5                   10                  15

Gln Pro Thr Val Pro Ser Gly Ser Gly Gly Thr Ile Lys Gly Leu Lys
            20                  25                  30

Asn Thr Ile Ile Val Pro Val Pro Gly Asp Thr Val Ile Thr Thr Arg
        35                  40                  45

Ser Asn Leu Leu Phe Arg Leu Val Tyr Ile Ile Gly Asn Pro Asp Thr
    50                  55                  60

Pro Leu Ser Thr Ser Thr Gly Ala Ile Ile Ser Leu Leu Thr Leu Phe
65                  70                  75                  80

Val Glu Ser Pro Gly Gln Leu Ile Gln Arg Ile Ala Asp Asp Pro Asp
                85                  90                  95

Ala Val Phe Lys Leu Val Glu Val Val Pro Glu Val Gly Asn Pro Gly
            100                 105                 110

Glu Leu Thr Phe Ala Ser Arg Gly Ile Asn Leu Asp Lys Gln Ala Gln
        115                 120                 125

Gln Tyr Phe Arg Leu Ala Glu Lys Asn Asp Gln Gly Tyr Tyr Val Ser
    130                 135                 140

Leu Gly Phe Glu Asn Pro Pro Asn Asp Asp Asp Ile Thr Ser Ser Pro
145                 150                 155                 160

Glu Ile Leu Asn Tyr Ile Leu Ala Ser Val Leu Ala Gln Ile Trp Ile
                165                 170                 175

Leu Leu Ala Lys Ala Val Thr Ala Pro Asp Thr Gly Gly Glu Ala Glu
            180                 185                 190
```

Asn Arg Arg Trp Ile Lys Leu Met Gln Gln Arg Arg Val Asp Gly Glu
            195                 200                 205

Leu Arg Leu Ser Lys Gly Trp Leu Asp Leu Val Arg Asn Lys Ile Ala
    210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
            260                 265                 270

Ile Lys Phe Gly Ile Glu Thr Arg Tyr Pro Ala Leu Ala Leu His Glu
        275                 280                 285

Phe Ser Gly Glu Leu Ala Thr Ile Glu Gly Leu Met Lys Leu Tyr Gln
290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Ser Gly Leu Asn Phe
            340                 345                 350

Thr Arg Ser Phe Phe Asp Pro Thr Tyr Phe Arg Leu Gly Gln Glu Met
        355                 360                 365

Val Arg Arg Ser Ser Gly Met Val Asn Ser Ser Phe Ala Lys Glu Leu
370                 375                 380

Gly Leu Ser Glu His Glu Thr Gln Leu Val Ser Gln Ile Ile Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Ala Lys Asp Asn Ile Thr Asp Arg Ser Glu Asp
            420                 425                 430

Pro Leu Ile Ala Ile Pro Gly Ser Ser Gly Pro Leu Pro Gly His
        435                 440                 445

Asp Pro Asn Ile Ser Gly Asp Ser Tyr Arg Ile Asp Ser Ser Thr Lys
450                 455                 460

Asp Thr Asn Asn Ile Ser Asp Gly Gly Thr Asn Pro Ser His Asp Val
465                 470                 475                 480

Ser Asn Ser Ala Met Glu Glu Leu Arg Arg Leu Val Glu Ser Thr Asn
                485                 490                 495

Lys Ile Asp Thr Lys Lys Ser Glu Ser Pro Gly Ile Val Asn His Tyr
            500                 505                 510

Asn Asp Thr Asp Leu Leu Arg
        515

<210> SEQ ID NO 10
<211> LENGTH: 491
<212> TYPE: PRT
<213> ORGANISM: Feline Paramyxovirus-Type 2
<220> FEATURE:
<223> OTHER INFORMATION: Phosphoprotein, Strain TV25

<400> SEQUENCE: 10

Met Ser Ala Glu Gln Ile Gln Gln Val Arg His Gly Leu Glu Ser Leu
1               5                   10                  15

Gln Glu Ile Lys Asn Asn Pro Pro Ser Gln Asp Val Asn Leu Ala
            20                  25                  30

-continued

Arg Glu Ile Tyr Glu Ser Ile Lys Gln Thr Gly Thr Pro Ser Thr Gln
            35                  40                  45

Gly Gly Thr Ile Thr Gly Asn Asn Thr Thr Ser Gly Cys Asp Asn Tyr
 50                  55                  60

Ser Met His Ser Gln Gly Ser Gly Pro Ser Val Ser Gly Ala Asp Lys
 65                  70                  75                  80

Asn Ile Glu Arg Leu Thr Gly Pro Asp Tyr Ser Glu Leu Trp Asp Pro
                85                  90                  95

Glu Gly Asn Leu Cys Met Leu Phe Glu Ser Asp Asp Asp Asn Asn
            100                 105                 110

Tyr Ser Glu Ile Asn Gly Arg Ser Thr Ala Ile Glu Gly Leu Asp Glu
            115                 120                 125

Gln Asn Asn Lys Asp Pro Gly Ile Lys Gln Ser Gly Asp Gln Cys Ser
130                 135                 140

Glu Gly Val Ser Lys Ile Asn Ser Ser Ser Pro Gln Glu Ala Thr
145                 150                 155                 160

Leu Ser Ser Gly Arg Ser Asp Ile Ser Gly Thr Gly Val Ser Pro Cys
                165                 170                 175

Ala Ser Leu Asp Ile Thr Val Asn Glu Leu Glu Asp Ala Thr Val Lys
            180                 185                 190

Asn Ser Asn Asn Met Lys Gly Asn Trp Pro Ile Pro Lys Leu Leu Val
            195                 200                 205

Lys Pro Pro Arg Met Lys Ser Leu Ser Asp Ser Val Thr Pro Leu
    210                 215                 220

Lys Gly Ala Thr Asp Gly Lys Ser Val Leu Pro Gly Met Glu Ile Thr
225                 230                 235                 240

Leu Ser Gly Lys Asn Gly Ala Thr Leu Pro Val His Pro Phe Thr Gln
                245                 250                 255

Pro Val Lys Asp Ser Asn Ala Asp Val Ser Asn Val Arg Gln His Val
            260                 265                 270

Pro Ser Val Thr Asp Gly Tyr Ser Asp Asn Glu Glu Val Pro Gly
            275                 280                 285

Leu His Lys Glu Thr Ile Asp Lys Ala Asp Leu Ser Met Gln Asp Ile
            290                 295                 300

Tyr Asn Leu Ile Leu Gly Phe Lys Asp Asp Tyr Arg Lys Leu Ser Asn
305                 310                 315                 320

Lys Leu Asp Met Ile Leu Glu Met Lys Gln Asp Ile Asp Asn Leu Lys
                325                 330                 335

Lys Ser Ser Ala Lys Ile Gln Leu Ala Leu Ser Thr Ile Glu Gly His
            340                 345                 350

Leu Ser Ser Val Met Ile Ala Ile Pro Gly Ser Gly Ile Asp Met Asn
            355                 360                 365

Gln Asp Glu Lys Lys Asp Gln Leu Asn Ser Asp Leu Lys Pro Leu Leu
            370                 375                 380

Gly Arg Asp His Cys Arg Ala Phe Arg Glu Val Thr Asn Pro Leu Asp
385                 390                 395                 400

Glu Thr Ser Leu Thr Asn Ala Pro Thr Lys His Val Ala Lys Ile Asn
                405                 410                 415

Lys Asn Cys Thr Leu Gln Lys Ile Asn Lys Asn Glu Thr Ser Ala Ile
            420                 425                 430

Lys Phe Val Pro Asn Asp Ser Tyr Ala Ser Ile Ser Thr Ile Lys Ser
            435                 440                 445

Ile Val Lys Ser Ser Asn Leu Asn Gln Glu Leu Lys Val Lys Leu Leu

-continued

```
    450                 455                 460

Thr Ile Leu Ser Gln Ile Lys Gly Val Asp Asn Ile Lys Glu Phe Tyr
465                 470                 475                 480

Glu Lys Val Met Ile Leu Ile Lys Asn Asn Asn
                485                 490

<210> SEQ ID NO 11
<211> LENGTH: 337
<212> TYPE: PRT
<213> ORGANISM: Feline Paramyxovirus-Type 2
<220> FEATURE:
<223> OTHER INFORMATION: Matrix protein, Strain TV25

<400> SEQUENCE: 11

Met Thr Glu Ile Phe Asn Leu Asp Glu Ser Ser Trp Ser Val Lys Gly
1               5                   10                  15

Thr Leu Asp Pro Leu Thr Pro Asp Thr Tyr Pro Asp Gly Arg Leu Val
            20                  25                  30

Pro Lys Ile Arg Val Ile Asp Pro Gly Leu Gly Asp Arg Lys Ser Gly
        35                  40                  45

Gly Tyr Met Tyr Leu Leu Leu His Gly Val Ile Glu Asp Ser Glu Thr
    50                  55                  60

Val Ile Asn Pro Lys Gly Arg Ala Phe Gly Ala Phe Pro Leu Gly Val
65                  70                  75                  80

Gly Gln Ser Thr Glu Asn Pro Glu Asp Leu Phe Lys Glu Ile Leu Thr
                85                  90                  95

Leu Asn Ile Val Thr Arg Arg Thr Ala Gly Phe Asn Glu Lys Leu Val
            100                 105                 110

Tyr Tyr Asn Thr Thr Pro Leu Asn Leu Leu Thr Pro Trp Lys Lys Val
        115                 120                 125

Leu Ala Tyr Gly Ser Ile Phe Thr Ala Asn Gln Val Cys Asn Asn Thr
    130                 135                 140

Ser Ser Ile Pro Ile Asp Ile Pro Gln Lys Phe Arg Pro Val Tyr Leu
145                 150                 155                 160

Thr Val Thr Lys Leu Ser Asp Asp Gly Tyr Tyr Gln Ile Pro Lys Met
                165                 170                 175

Ile Gln Asp Phe Lys Ser Ser Asn Ser Val Ala Phe Asn Ile Leu Val
            180                 185                 190

His Leu Ser Met Gly Thr Ile Leu Leu Asp Ser Ser Lys Gly Ser Arg
        195                 200                 205

Val Gly Asn Pro Ala Glu Asn Leu Ile Thr Phe Met Ile His Ile Gly
    210                 215                 220

Asn Phe Lys Arg Lys Asn Asn Lys Ala Tyr Ser Pro Glu Tyr Cys Lys
225                 230                 235                 240

Arg Lys Ile Met Arg Leu Gly Leu Ile Phe Ser Leu Gly Ala Ile Gly
                245                 250                 255

Gly Thr Ser Leu His Ile Arg Cys Thr Gly Lys Met Ser Lys Arg Leu
            260                 265                 270

Gln Ala Tyr Leu Gly Phe Lys Arg Thr Leu Cys Tyr Pro Leu Met Tyr
        275                 280                 285

Val Asn Glu Gly Leu Asn Lys Thr Leu Trp Arg Asn Glu Cys Arg Ile
    290                 295                 300

Glu Lys Val Gln Ala Val Leu Gln Pro Ser Val Pro Asn Glu Phe Lys
305                 310                 315                 320

Ile Tyr Asp Asp Ile Ile Ile Asp Asn Thr Asn Gly Leu Phe Lys Val
```

```
                325                 330                 335

Lys

<210> SEQ ID NO 12
<211> LENGTH: 543
<212> TYPE: PRT
<213> ORGANISM: Feline Paramyxovirus-Type 2
<220> FEATURE:
<223> OTHER INFORMATION: Fusion protein, Strain TV25

<400> SEQUENCE: 12

Met Tyr Lys Ile Lys Val Val Ile Met Gly Phe Leu Leu Leu Ser Asp
1               5                   10                  15

Ile Thr Phe Ala Gln Val Gly Trp Asp Asn Leu Thr Ser Ile Gly Val
            20                  25                  30

Ile Ser Thr Lys Gln Tyr Asn Tyr Lys Ile Thr Thr Leu Asn Thr Asn
        35                  40                  45

Gln Leu Met Val Ile Lys Met Val Pro Asn Ile Ser Ser Ile Ile Asn
    50                  55                  60

Cys Thr Lys Leu Glu Leu Ala Lys Tyr Arg Glu Leu Ile Thr Gly Ile
65                  70                  75                  80

Leu Arg Pro Ile Asn Glu Ser Leu Glu Leu Met Asn Ser Tyr Ile Asn
                85                  90                  95

Met Arg Thr Gly Ser Glu Arg Phe Ile Gly Ala Val Ile Ala Gly Val
            100                 105                 110

Ala Leu Gly Val Ala Thr Ala Ala Gln Ile Thr Ser Gly Ile Ala Leu
        115                 120                 125

His Asn Ser Ile Met Asn Lys Lys Gln Ile Gln Glu Leu Arg Lys Ala
    130                 135                 140

Leu Ser Thr Thr Asn Lys Ala Ile Asp Glu Ile Arg Ile Ala Gly Glu
145                 150                 155                 160

Arg Thr Leu Ile Ala Val Gln Gly Val Gln Asp Tyr Ile Asn Asn Val
                165                 170                 175

Ile Ile Pro Met Gln Glu Lys Leu Gln Cys Asp Ile Leu Ala Ser Gln
            180                 185                 190

Leu Ser Ile Ala Leu Leu Arg Tyr Tyr Thr Asn Ile Leu Thr Val Phe
        195                 200                 205

Gly Pro Ser Ile Arg Asp Pro Ile Thr Ser Thr Ile Ser Ile Gln Ala
    210                 215                 220

Leu Ser Gln Ala Phe Asn Gly Asn Leu Gln Ala Leu Leu Asp Gly Leu
225                 230                 235                 240

Gly Tyr Thr Gly Gln Asp Leu His Asp Leu Ile Glu Ser Arg Ser Ile
                245                 250                 255

Thr Gly Gln Ile Ile His Ala Asp Met Thr Asp Leu Phe Leu Ile Leu
            260                 265                 270

Arg Ile Asn Tyr Pro Ser Ile Thr Asp Met Gln Gly Val Val Ile Tyr
        275                 280                 285

Glu Leu Asn Ser Ile Thr Tyr His Ile Gly Pro Glu Glu Trp Tyr Thr
    290                 295                 300

Ile Met Pro Asn Phe Ile Ala Val Gln Gly Phe Leu Val Ser Asn Phe
305                 310                 315                 320

Asp Glu Arg Lys Cys Ser Ile Thr Lys Thr Ser Ile Leu Cys Gln Gln
                325                 330                 335

Asn Ser Ile Tyr Pro Met Ser Thr Glu Met Gln Arg Cys Ile Lys Gly
            340                 345                 350
```

```
Glu Ile Lys Phe Cys Pro Arg Ser Lys Ala Ile Gly Thr Leu Val Asn
            355                 360                 365

Arg Phe Ile Leu Ile Asn Gly Asn Leu Met Ala Asn Cys Leu Gly Ile
370                 375                 380

Ile Cys Arg Cys Tyr Thr Ser Gly Gln Ile Ile Thr Gln Asp Pro Asn
385                 390                 395                 400

Lys Leu Ile Thr Ile Ile Ser Gln Glu Cys Arg Glu Val Gly Val
                405                 410                 415

Asp Gly Ile Arg Ile Met Val Gly Pro Lys Lys Leu Pro Asp Val Ile
            420                 425                 430

Phe Asn Ala Arg Leu Glu Ile Gly Val Pro Ile Ser Leu Ser Lys Leu
            435                 440                 445

Asp Val Gly Thr Asp Leu Ala Ile Ala Ser Ala Lys Leu Asn Asn Ser
450                 455                 460

Lys Ala Leu Leu Glu Gln Ser Asp Lys Ile Leu Asn Ser Met Ser Lys
465                 470                 475                 480

Leu Asp Ser Leu Asn Ser Arg Ile Leu Gly Ser Val Phe Ile Met Met
                485                 490                 495

Ile Ile Phe Val Ile Val Ile Val Ile Ile Trp Ile Ile Cys Lys Lys
            500                 505                 510

Cys Arg Asn Lys Arg Asn Lys Leu Ser Ala Ser Ile Glu Pro Leu Tyr
            515                 520                 525

Ile Pro Pro Ser Tyr Asn Ser Pro His Ser Ile Val Lys Ser Ile
            530                 535                 540

<210> SEQ ID NO 13
<211> LENGTH: 595
<212> TYPE: PRT
<213> ORGANISM: Feline Paramyxovirus-Type 2
<220> FEATURE:
<223> OTHER INFORMATION: Hemagglutinin, Strain TV25

<400> SEQUENCE: 13

Met Glu Ser Asn Asn Asn Lys Tyr Tyr Lys Asp Ser Asn Arg Tyr Phe
1               5                   10                  15

Ser Lys Ile Leu Asp Glu Asn Lys Thr Val Asn Asn His Leu Tyr Ser
            20                  25                  30

Leu Ser Ile Arg Ile Ile Thr Val Ile Ala Ile Val Ser Leu Ile
        35                  40                  45

Ala Thr Thr Ile Thr Ile Ile Asn Ala Ile Ser Gly Arg Thr Thr Leu
    50                  55                  60

Asn Asn Asn Met Asp Met Leu Leu Asn Gln Gln Asp Lys Ile Asn Asn
65                  70                  75                  80

Ile Lys Glu Met Ile Phe Asp Arg Ile Tyr Pro Leu Ile Asn Ala Met
                85                  90                  95

Ser Thr Glu Leu Gly Leu His Ile Pro Thr Leu Leu Asp Glu Leu Thr
            100                 105                 110

Lys Ser Ile Asp Gln Lys Ile Lys Ile Met Thr Pro Pro Leu Glu Thr
        115                 120                 125

Thr Thr Ser Asn Leu Asn Trp Cys Ile Asn Pro Asn Gly Ile Ile
    130                 135                 140

Val Asp Pro Lys Gly Tyr Cys Glu Gly Leu Glu Leu Ser Lys Thr Tyr
145                 150                 155                 160

Lys Leu Leu Leu Asp Gln Leu Asp Met Leu Arg Lys Lys Ser Leu Ile
                165                 170                 175
```

```
Ile Asn Lys Lys Ser Ile Asn Gln Cys Arg Leu Val Asp Ser Ser Asn
            180                 185                 190
Ile Ile Phe Ala Thr Val Asn Ile Gln Ser Thr Pro Arg Phe Leu Asn
        195                 200                 205
Leu Gly His Thr Val Ser Asn Gln Arg Ile Thr Phe Gly Gln Gly Thr
    210                 215                 220
Tyr Ser Ser Thr Tyr Ile Ile Thr Ile Gln Glu Asp Gly Leu Thr Asp
225                 230                 235                 240
Val Gln Tyr Arg Val Phe Glu Ile Gly Tyr Ile Ser Asp Gln Phe Gly
                245                 250                 255
Thr Phe Pro Ser Leu Ile Val Ser Arg Val Leu Pro Val Arg Met Val
            260                 265                 270
Leu Gly Met Glu Ser Cys Thr Leu Thr Ser Asp Lys Phe Gly Gly Tyr
        275                 280                 285
Phe Leu Cys Met Asn Ile Pro Thr Arg Ser Ile Tyr Asp Tyr Val Asn
    290                 295                 300
Ile Arg Asp Leu Lys Ser Leu Tyr Val Thr Ile Pro His Tyr Gly Lys
305                 310                 315                 320
Ile Asn Tyr Thr Tyr Phe Asn Phe Gly Lys Val Arg Ser Pro His Glu
                325                 330                 335
Ile Asp Lys Ile Trp Leu Thr Ser Glu Arg Gly Gln Met Ile Ser Gly
            340                 345                 350
Tyr Phe Ala Ala Phe Val Thr Ile Thr Ile Arg Asn Tyr Asn Asn Tyr
        355                 360                 365
Pro Tyr Lys Cys Leu His Asn Pro Cys Leu Glu Arg Ser Glu Ser Tyr
    370                 375                 380
Cys Lys Gly Trp Tyr Lys Asn Ile Thr Gly Thr Asp Asp Val Pro Ile
385                 390                 395                 400
Leu Ala Tyr Leu Leu Val Glu Met Lys Asp Glu Gly Pro Leu Ile
                405                 410                 415
Thr Leu Val Glu Ile Pro Pro Tyr Asn Tyr Thr Ala Pro Ser His Asn
            420                 425                 430
Ser Leu Tyr Tyr Asp Asp Lys Ile Asn Lys Leu Ile Met Thr Thr Ser
        435                 440                 445
His Ile Gly Tyr Ile Gln Ile Asn Glu Val His Glu Val Ile Val Gly
    450                 455                 460
Asp Asn Leu Lys Ala Ile Leu Leu Asn Arg Leu Ser Asp Glu His Pro
465                 470                 475                 480
Thr Leu Thr Ala Cys Arg Phe Asn Gln Glu Ile Lys Glu Arg His Ile
                485                 490                 495
Ser Asp Gly Leu Ile Ile Ser Asn Ser Ala Leu Ile Asp Ile Gln Glu
            500                 505                 510
Arg Met Tyr Ile Thr Val Lys Ala Val Pro Pro Ile Gly Asn Tyr Asn
        515                 520                 525
Phe Thr Val Glu Leu His Ser Arg Ser Asn Thr Ser Tyr Val Gly Leu
    530                 535                 540
Pro Arg Gln Phe Asn Ala Arg Tyr Asp Lys Leu His Leu Glu Cys Phe
545                 550                 555                 560
Ala Trp Asp Arg Ser Trp Cys Ala Leu Ile Pro Gln Phe Ser Leu
                565                 570                 575
Ser Trp Asn Glu Ser Leu Ser Val Asp Thr Ala Ile Phe Asn Leu Ile
            580                 585                 590
```

```
Asn Cys Asn
        595

<210> SEQ ID NO 14
<211> LENGTH: 2202
<212> TYPE: PRT
<213> ORGANISM: Feline Paramyxovirus-Type 2
<220> FEATURE:
<223> OTHER INFORMATION: Polymerase, Strain TV25

<400> SEQUENCE: 14

Met Glu Gln Ser Asp Tyr Gln Asp Ile Leu Tyr Pro Glu Val His Leu
1               5                   10                  15

Asn Ser Pro Ile Val Ile Ser Lys Leu Val Gly Ile Leu Glu Tyr Ser
            20                  25                  30

Lys Val Val His Asn Gln Gln Leu Ser Asp His Thr Ile Val Lys Asn
        35                  40                  45

Ile Gln Phe Arg Leu Arg Asn Gly Phe Asn Ser Pro Arg Val Gln Thr
    50                  55                  60

Leu Leu Val Met Gly Glu Ile Ile Asn Lys Ile Lys Asn Lys Tyr Pro
65                  70                  75                  80

Asn Tyr Leu His Ile Pro Tyr Pro Glu Cys Asn Gln Lys Leu Phe Arg
                85                  90                  95

Met Ala Asp Pro Glu Leu Thr Ser Lys Leu Glu Ala Leu Leu Asp Lys
            100                 105                 110

Gly Asp Thr Leu Tyr Leu Lys Ile Lys Thr Glu Ile Ile Ala Cys Phe
        115                 120                 125

Asp Lys Leu Lys Thr Lys Met Ser Ile Thr Asn Asp Leu Ile Ser Asp
    130                 135                 140

Asn Arg Gln Leu Ile Ser Asp Leu Pro Leu Ile Val Lys Gly Ser Gln
145                 150                 155                 160

Trp Phe Phe Pro Phe Leu Leu Trp Phe Ser Val Lys Thr Glu Thr Arg
                165                 170                 175

Asn Cys Ile Arg Gln Asn Gln Lys Thr Arg Val Arg Ser Gln Tyr Arg
            180                 185                 190

Pro His Leu Ser Glu Thr Lys Arg Ile Thr Leu Val Val Thr Pro Asp
        195                 200                 205

Leu Ile Thr Ile Phe Asp His Val Asn Lys Cys Ile Tyr His Leu Thr
    210                 215                 220

Phe Glu Met Leu Leu Met Tyr Cys Asp Val Val Glu Gly Arg Leu Met
225                 230                 235                 240

Thr Glu Ala Ser Met Ser Leu Asp His Arg Phe Ile Asn Leu Leu Ser
                245                 250                 255

Arg Val Gln Tyr Met Trp Asp Leu Leu Asp Gly Met Phe Glu Ser Leu
            260                 265                 270

Gly Asn Gln Leu Tyr Ser Ile Ile Ala Leu Leu Glu Pro Leu Ser Leu
        275                 280                 285

Ala Tyr Leu Gln Leu Met Asp Ala Asp Pro Gln Ile Arg Gly Thr Phe
    290                 295                 300

Leu His His Cys Leu Ser Glu Leu Glu Glu Leu Leu Phe Ser Lys Ser
305                 310                 315                 320

Pro Phe Asp Pro Val Ile Tyr Glu Asn Leu Ile Ser Gly Leu Asp Tyr
                325                 330                 335

Ile Tyr Leu Thr Asp Asp Ile His Leu Thr Ala Glu Ile Phe Ser Phe
            340                 345                 350
```

```
Phe Arg Ser Phe Gly His Pro Tyr Leu Glu Ala Gln Asn Ala Ala Ser
            355                 360                 365

Asn Val Arg Lys Tyr Met Asn Gln Pro Lys Val Ile Ser Tyr Gln Thr
370                 375                 380

Leu Met Gln Gly His Ala Ile Phe Cys Gly Ile Ile Asn Gly Phe
385                 390                 395                 400

Arg Asp Arg His Gly Gly Thr Trp Pro Val Leu Pro His His
                405                 410                 415

Ala Ser Ala Val Ile Arg Asn Ala Gln Leu Ser Gly Glu Gly Leu Thr
                420                 425                 430

Pro Glu Gln Cys Ala Gln Tyr Trp Arg Ser Phe Cys Gly Phe Lys Phe
            435                 440                 445

Lys Cys Phe Met Pro Leu Ser Leu Asp Ser Asp Leu Thr Met Tyr Leu
    450                 455                 460

Arg Asp Lys Ala Leu Ser Pro Ile Lys Asn Glu Trp Asp Ser Val Tyr
465                 470                 475                 480

Ala Lys Glu Tyr Leu Arg Tyr Asn Pro Gly Leu Pro Thr Ser Ser Arg
                485                 490                 495

Arg Leu Val Asn Val Phe Leu Glu Asp Asp Lys Phe Asp Pro Tyr Glu
                500                 505                 510

Met Ile Met Tyr Val Ile Asn Gly Asp Tyr Leu Arg Asp Asn Glu Phe
            515                 520                 525

Asn Leu Ser Tyr Ser Leu Lys Glu Lys Glu Ile Lys Glu Val Gly Arg
    530                 535                 540

Leu Phe Ala Lys Met Thr Tyr Lys Met Arg Ala Cys Gln Val Ile Ala
545                 550                 555                 560

Glu Asn Leu Ile Ala Asn Gly Val Gly Lys Phe Phe Lys Asp Asn Gly
                565                 570                 575

Met Ala Lys Asp Glu His Lys Leu Thr Lys Thr Leu His Lys Leu Ala
                580                 585                 590

Ile Ser Gly Val Pro Lys Asp Asn Ser Gln Leu Tyr Leu Ser Glu Cys
            595                 600                 605

Trp Glu Gln Val Val Glu Gln Cys Val Thr Ser Thr Gln Thr Lys Asn
    610                 615                 620

Gln Ile Ile Ser Ser His Ser Gly Lys Ser Val Ala Ser Lys Phe Ser
625                 630                 635                 640

Arg Ser Asn Pro Asn Asp Arg Gly Ile Leu Asn Ser Gly Arg His Leu
                645                 650                 655

Asn Lys His Pro Lys His Pro Ser Asn Thr Glu Tyr Tyr Glu Thr Val
                660                 665                 670

Ser Ser Phe Ile Thr Thr Asp Leu Lys Lys Tyr Cys Leu Asn Trp Arg
            675                 680                 685

Tyr Glu Ser Ser Ser Val Phe Ala Glu Arg Leu Asn Glu Ile Tyr Gly
    690                 695                 700

Leu Pro Gly Phe Phe His Trp Leu His Arg Ile Leu Glu Lys Ser Val
705                 710                 715                 720

Leu Tyr Val Ser Asp Pro Ser Pro Asp Phe Asp Gln His Val
                725                 730                 735

Asp Ile Asp Ser Val Pro Asn Asp His Ile Phe Ile Lys Tyr Pro Met
                740                 745                 750

Gly Gly Ile Lys Gly Phe Cys Gln Lys Leu Trp Thr Ile Ser Thr Ile
            755                 760                 765

Pro Phe Leu Tyr Leu Ala Ala Phe Asp Thr Gly Val Arg Ile Ser Ser
```

```
                770               775               780
Leu Val Gln Gly Asp Asn Gln Ala Ile Ala Val Thr Lys Arg Val Pro
785               790               795               800

Ser Ser Trp Ser Tyr Ser Arg Lys Glu Glu Ser Thr Lys Val Thr
            805               810               815

Thr Gln Tyr Phe Leu Asn Leu Arg Gln Arg Leu His Asp Ile Gly His
            820               825               830

Glu Leu Lys Ala Asn Glu Thr Ile Ile Ser Ser His Phe Phe Val Tyr
            835               840               845

Ser Lys Gly Ile Tyr Tyr Asp Gly Ile Leu Leu Ser Gln Ser Leu Lys
            850               855               860

Ser Ile Ala Arg Cys Val Phe Trp Ser Glu Thr Ile Val Asp Glu Thr
865               870               875               880

Arg Ser Ala Cys Ser Asn Ile Ser Thr Thr Leu Ala Lys Ala Ile Glu
            885               890               895

Arg Gly Tyr Asp Lys Phe Val Ala Tyr Ala Ile Asn Ile Tyr Lys Thr
            900               905               910

Ile His Gln Val Leu Ile Ala Leu Ser Phe Thr Ile Asn Pro Thr Met
            915               920               925

Thr Pro Asp Ile Thr Glu Pro Phe Tyr Lys Ser Leu Asp Leu Leu Lys
            930               935               940

Asn Leu Ile Leu Ile Pro Ala Pro Leu Gly Gly Met Asn Tyr Met Asn
945               950               955               960

Met Ser Arg Leu Phe Val Arg Asn Ile Gly Asp Pro Ile Thr Ala Ser
            965               970               975

Phe Ala Asp Ile Lys Arg Met Ile Glu Cys Gly Leu Leu Gly His Asn
            980               985               990

Val Leu Ser Gln Ile Met Tyr Gln Lys Cys Gly Thr Ser Lys Tyr Leu
            995              1000              1005

Asp Trp Ala Ser Asp Pro Tyr Ser Ile Asn Leu Pro Tyr Ser Gln Ser
           1010              1015              1020

Met Thr Lys Val Leu Lys Asn Ile Thr Ala Arg Tyr Val Leu Met His
1025              1030              1035              1040

Ser Pro Asn Pro Met Leu Lys Asp Leu Phe His Glu Lys Ser Gln Glu
           1045              1050              1055

Glu Asp Glu Ile Leu Ala Glu Phe Leu Leu Asp Arg Gln Leu Ile Ile
           1060              1065              1070

Pro Arg Ala Ala His Glu Ile Leu Ser Asn Ser Val Thr Gly Ala Arg
           1075              1080              1085

Glu Ser Ile Ala Gly Met Leu Asp Thr Thr Lys Gly Leu Ile Arg Ala
           1090              1095              1100

Ser Met Ser Arg Gly Gly Leu Thr Ser Ser Leu Val Leu Lys Leu Ser
1105              1110              1115              1120

Thr Tyr Asp Tyr Gln Gln Phe Arg Thr Cys Leu Glu Trp Leu Tyr Ala
           1125              1130              1135

Pro Thr Thr Gly Ile Ala Val Ser Ala Asp Ser Cys Ser Val Phe Leu
           1140              1145              1150

Ala Arg Ala Ile Arg Lys Arg Met Trp Val His Leu Thr Lys Gly Arg
           1155              1160              1165

Glu Ile Tyr Gly Leu Glu Val Pro Asp Ile Leu Glu Cys Met Gln Ser
           1170              1175              1180

Asn Val Ile Val Asp His Glu Asp Cys Tyr Ser Cys Ile Gln Gly Ser
1185              1190              1195              1200
```

```
Arg Tyr Tyr Thr Trp Phe Phe Val Pro Ser Asn Cys Gln Leu Asp Gln
                1205                1210                1215

Ile Asn Lys Ser Thr Asn Ser Leu Arg Val Pro Tyr Ile Gly Ser Thr
                1220                1225                1230

Thr Glu Glu Arg Ser Asp Met Lys Leu Ser Tyr Val Arg Ser Pro Ser
                1235                1240                1245

Arg Pro Leu Lys Ala Ala Val Arg Ile Ala Ala Val Tyr Thr Trp Ala
                1250                1255                1260

Tyr Gly Asp Asp Asp Leu Ser Trp Arg Glu Ala Trp Tyr Leu Ala Arg
1265                1270                1275                1280

Thr Arg Ala Asn Val Thr Phe Asp Glu Leu Lys Leu Val Thr Pro Ile
                1285                1290                1295

Ala Thr Ser Thr Asn Leu Ala His Arg Leu Arg Asp Arg Ser Thr Gln
                1300                1305                1310

Val Lys Tyr Ser Gly Thr Ser Leu Val Arg Val Ala Arg Tyr Thr Thr
                1315                1320                1325

Ile Ser Asn Asp Asn Met Ser Phe Val Ile Asn Asp Lys Lys Val Asp
                1330                1335                1340

Thr Asn Phe Val Tyr Gln Gln Gly Met Leu Leu Gly Leu Ser Ile Leu
1345                1350                1355                1360

Glu Tyr Ile Phe Arg Tyr Cys Lys Ser Thr Gly Gln Ser Asn Thr Val
                1365                1370                1375

Val His Leu His Ala Asp Val Asn Cys Cys Ile Ile Gln Met Thr Asp
                1380                1385                1390

Gln Pro Tyr Thr Pro Ser Leu Thr Lys Lys Leu Pro Glu Ile Lys Pro
                1395                1400                1405

Ile Asn Asn Lys Leu Ile Tyr Asp Pro Ala Pro Ile Ile Asp Thr Asp
                1410                1415                1420

Ala Ala Arg Leu Tyr Ser Gln Lys Tyr Leu Ser His Leu Ile Asp Phe
1425                1430                1435                1440

Pro Asn Trp Ser Met Asn Gln Leu Asn Val Val Leu Ala Lys Val Val
                1445                1450                1455

Ala Ile Ser Ile Val Asp Leu Ile Thr Lys Ala Ser Lys Asp His Leu
                1460                1465                1470

Asn Glu Ile Met Ala Val Val Gly Asp Asp Asp Ile Asn Ser Phe Ile
                1475                1480                1485

Thr Glu Phe Leu Leu Val Asp Pro Arg Leu Phe Thr Leu Tyr Leu Gly
                1490                1495                1500

Gln Tyr Thr Ser Leu Gln Trp Ala Tyr Glu Ile His Tyr His Arg Pro
1505                1510                1515                1520

Val Gly Lys Tyr Gln Met Ala Glu Val Leu His Thr Leu Leu Ser Arg
                1525                1530                1535

Ala Ser Lys Gly Ile Phe Asn Ile Leu Thr Asn Ala Phe Ser His Pro
                1540                1545                1550

Arg Val Tyr Lys Arg Phe Trp Glu Cys Gly Leu Leu Glu Pro Ile Tyr
                1555                1560                1565

Gly Pro Tyr Ile Gly Ser Gln Asn Leu Tyr Ser Thr Val Ile Asp Tyr
                1570                1575                1580

Leu Tyr Asn Ala Tyr Ile Thr Tyr Leu Asp Ala Tyr Leu Ser Asp His
1585                1590                1595                1600

Ile Glu Asp Ala Asp Ile Val Ile Cys Glu Thr Glu Glu Thr Cys Leu
                1605                1610                1615
```

Ala Asn Arg Ile Asp Asn Tyr Gln Gly Arg His Leu Ala Val Leu Ile
    1620                1625                1630

Asp Leu Tyr Cys Asp Ser Thr Arg Cys Pro Asn Ile Lys Gly Ser Asp
        1635                1640                1645

Thr Ile Met Arg Asn Ser Ile Leu Lys Ser Phe Ile Asp Asn Glu Arg
    1650                1655                1660

Arg Thr Ser Pro Leu Gly Leu Thr Trp Asn Leu Asp Pro Leu Leu Ile
1665                1670                1675                1680

Asp His Phe Ser Cys Ser Ile Thr Tyr Leu Arg Arg Gly Ile Ile Lys
            1685                1690                1695

Gln Ile Arg Leu Arg Phe Asp Pro Asn Ile Ser Ile Glu Leu Val Lys
        1700                1705                1710

Leu Ala Lys Pro Glu Val Ile His Gln Gly Pro Lys Ile Pro Ser Ser
    1715                1720                1725

Trp Ala Leu Ile Asp Ile Asn Pro Glu Val Asn Asp Leu Asn Thr Val
    1730                1735                1740

Phe Gly Glu Leu Asn Ser Lys Trp Lys Asp Ile Pro Ile Gly Gln Ile
1745                1750                1755                1760

Arg Ile Gln Asn Phe Glu Ile His Ala Tyr Arg Arg Ile Gly Val Asn
            1765                1770                1775

Ser Thr Ala Cys Tyr Lys Ala Leu Glu Met Leu Ser Val Leu Thr Arg
        1780                1785                1790

Phe Met Ser Asn Pro Ala Gly Ala Leu Phe Leu Gly Glu Gly Ala Gly
        1795                1800                1805

Ser Met Leu Val Thr Tyr Arg Ala Phe Ile Pro Phe Lys Arg Ile Tyr
    1810                1815                1820

Tyr Asn Ser Gly Val Ser Ile Gln Asn Ile Gln Ser Gln Arg Glu Leu
1825                1830                1835                1840

Ser Leu Tyr Pro Ser Glu Val Ala Leu Val Asp Asn Lys Asn Arg Leu
        1845                1850                1855

Thr Ser Asp Pro Asp Ile Lys Val Leu Phe Asn Gly Lys Pro Glu Ser
        1860                1865                1870

Thr Trp Val Gly Asn Ile Asp Cys Phe Ala Tyr Ile Leu Ser His Ile
    1875                1880                1885

Glu Thr Ser Ser Leu Thr Leu Ile His Ser Asp Ile Glu Ser Ser Leu
    1890                1895                1900

Ser Lys Thr Lys Asn Lys Ile Leu Glu Glu Leu Cys His Ile Leu Ser
1905                1910                1915                1920

Met Ala Leu Ile Leu Gly Lys Ile Gly Ser Val Leu Val Ile Lys Leu
            1925                1930                1935

Leu Pro Arg Val Gly Asp Tyr Thr Tyr Ser Phe Cys Lys Tyr Ala Ser
            1940                1945                1950

Glu Phe Tyr Gln Gln Asn Phe Phe Ile Leu Pro Arg Phe Ser Asn Met
        1955                1960                1965

Ser Ser Ser Glu Ile Tyr Tyr Val Gly Val His Leu Asn Thr Asn Arg
        1970                1975                1980

Leu Val Asp Pro Asp Arg Ile Val Gln Tyr Ile Ile Arg Asn Leu Gln
1985                1990                1995                2000

Ser Thr Pro Val Thr Phe Leu Ser Tyr Ile Leu Glu Thr Lys Tyr Arg
            2005                2010                2015

Asn Asn Met Val Thr Asn Tyr Gly Leu Cys Leu Ser Asp Gly His Lys
        2020                2025                2030

Ser Asp Tyr Leu Ser Ser Ile Thr Lys Ile Glu Asn Val Leu Leu Ser

-continued

```
          2035                2040                2045
Cys Gly Leu Glu Leu Asn Gly Pro Lys Ile Ile Gln Gln Leu Ser Gly
        2050                2055                2060
His Asp Tyr Ala Asn Gly Glu Ile Ser Leu Glu Ser Ser Ile Met Val
2065                2070                2075                2080
Leu Val Arg Glu Tyr Leu Asn Ala Thr Ile Gln Gly Arg Glu Thr Leu
                2085                2090                2095
Gly Leu Phe Ser Pro Tyr Pro Val Leu His Glu Ser Gln Leu Arg Glu
                2100                2105                2110
Ile Asn Arg Cys Ile Ala Leu Lys Tyr Val Val Tyr Leu Leu Phe Tyr
                2115                2120                2125
Ser Thr Ser Val Gly Ser Ser Arg Gln Ile Met Ser Asn Leu Arg Lys
        2130                2135                2140
Gly Val Leu Met Tyr Asp Leu Arg Asp Glu Phe Phe Met Glu Arg Leu
2145                2150                2155                2160
Ser Thr Asn Phe Lys Lys Lys Ile Met Ser Gln Glu Val Lys Thr Thr
                2165                2170                2175
Trp Ile Phe Asn Ile Asp Val Pro Thr Arg Lys Ala Leu Tyr Lys Leu
                2180                2185                2190
Val Gly Tyr Ser Leu Ile Ile Asn His Val
        2195                2200
```

PARAMYXOVIRUS AND USES THEREOF

FIELD OF THE INVENTION

The present invention relates to a novel feline paramyxovirus and vaccines and treatments against said novel paramyxovirus. The invention further relates to the detection of said paramyxovirus and the diagnosis of infections with said paramyxovirus.

BACKGROUND OF THE INVENTION

Paramyxoviruses are enveloped, negative-sense single-stranded RNA ((-)ssRNA) viruses that have been associated with a number of infectious diseases in humans and animals. There are two subfamilies of Paramoxoviruses, Paramyxovirinae and Pneumovirinae and at least five genera within the subfamily Paramyxovirinae, namely Respirovirus, Rubulavirus, Morbillivirus, Henipavirus, and Avulavirus. Examples of Paramyxoviruses include canine distemper virus, measles virus, rinderpest virus, mumps virus and human parainfluenza viruses. Paramyxoviruses have a linear genome encoding seven viral polypeptides: a nucleocapsid protein, a phospho-protein, a matrix protein, a fusion protein, a haemagglutinin protein and a polymerase. Paramyxovirus virions are enveloped and can be spherical, filamentous or pleomorphic with a diameter of around 150 nm. Fusion proteins and attachment proteins (hemagglutinin, "H") appear as spikes on the virion surface. Matrix proteins ("M") inside the envelope stabilize the structure of the virus. The nucleocapsid core is composed of the genomic RNA, nucleocapsid proteins ("N"), phosphoproteins ("P") and polymerase proteins ("L" for "large protein"). The fusion protein ("F") projects from the envelope surface as a trimer, and mediates cell entry by inducing fusion between the viral envelope and the cell membrane.

Paramyxoviruses have for example been isolated from wild-living and domestic animals including cats, rodents and bats but also humans. Paramyxovirus infections, particularly of the Paramyxovirinae subfamily, have been associated with kidney diseases due to renal tissue damage shown in various species. Kidney disease, especially chronic kidney disease (CKD) is, for instance, among the most common diseases and one of the most common causes of death in domestic cats, particularly in older individuals. Lulich et al. (Compendium on continuing education for the practicing veterinarian (1992) 14(2):127-125) report a prevalence of chronic kidney disease among total domestic cat populations of about 1.5% and about 7.5% in domestic cats older than 10 years. The causes of these diseases can be very diverse. In many cases the exact etiology cannot be determined. On the other hand, it is known that chronic kidney disease most often occurs as a result of inflammation of the renal tubules and renal interstitial tissue. This is called idiopathic tubulointerstitial nephritis (TIN).

Several feline paramyxoviruses have been described in the art. US 2013/0230529 A1 and Woo et al. (Proc. Nat. Acad. Sci. (2012) 109(14):5435-5440) describe a feline morbillivirus (FmoPV) isolated in Hong Kong which is associated with TIN in domestic cats. Other research groups from Japan (Sakaguchi et al. (2014) General Virology, 95(7), 1464-1468; Furuya et al. (2014) Archives of virology, 159 (2), 371-373), Italy (Lorusso et al. (2013) Vet Ital. 51(3): 235-237) and the USA (Sharp et al. (2016) Emerging Infectious Diseases 22(4):760) also detected paramyxoviruses in urine samples from cats. Sieg et al. (Virus Genes (2015) 51(2):294-297) describe the discovery of feline paramyxoviruses in domestic cats with chronic kidney disease.

However, these paramyxoviruses are genetically diverse and there is a need to identify relevant paramyxoviruses and provide vaccines and treatments against said paramyxoviruses.

DESCRIPTION OF THE INVENTION

The present invention provides a novel feline paramyxovirus designated Feline Paramyxovirus-Type 2 (FPaV-2). The paramyxovirus of the present invention is a (-)ssRNA virus and has in one aspect a genome which is complementary to the nucleic acid according to SEQ ID NO:1 or SEQ ID NO:8. These two sequences represent the complementary DNA sequences of the genome of two strains of FPaV-2 that were isolated by the present inventors, the 'Gordon' strain (SEQ ID NO:1) and strain 'TV25' (SEQ ID NO: 8). SEQ ID NO:1 and SEQ ID NO:8 are given as DNA sequences that correspond to the positive RNA-strand into which the negative RNA strand viral genome is transcribed, i.e. they comprise the ORFs in 5' to 3' direction like an mRNA. The skilled person is aware that the viral genome of the paramyxovirus of the invention is a (-)ssRNA genome. Hence, in one aspect the invention also relates to the nucleic acid according to SEQ ID NO:1 or SEQ ID NO:8 or a sequence being at least 80%, at least 85%, at least 90%, at least 91%, at least 92%, at least 93%, at least 94%, at least 95%, at least 96%, at least 97%, at least 98%, at least 99% identical to SEQ ID NO:1 or SEQ ID NO:8. The nucleic acid sequence of SEQ ID NO:1 or SEQ ID NO:8 comprises six open reading frames (ORFs) for the six viral polypeptides of the paramyxovirus. The sequence of elements on the nucleic acid of SEQ ID NO:1 or SEQ ID NO:8 is (from 5' to 3'): 3' untranslated region (UTR) of the viral genome, nucleocapsid protein ("N") ORF, phosphoprotein ("P") ORF, matrix protein ("M") ORF, fusion protein ("F") ORF, hemagglutinin ("H") ORF, RNA-dependent RNA polymerase ("L" for "large protein") ORF, 5' UTR. The following Table 1 describes the structure of the nucleic acids of SEQ ID NOs:1 and 8:

TABLE 1

Overview of the genome of a paramyxovirus according to the present invention

| Genome region | nucleotide position (in SEQ ID NO: 1) | corresponding polypeptide sequences |
|---|---|---|
| 3' UTR | 1-107 | — |
| nucleocapsid protein ORF | 108-1667 | SEQ ID NO: 2, SEQ ID NO: 9 |
| intergenic sequence | 1668-1780 | — |
| phosphoprotein ORF | 1781-3256 | SEQ ID NO: 3, SEQ ID NO: 10 |
| intergenic sequence | 3257-3388 | — |
| matrix protein ORF | 3389-4402 | SEQ ID NO: 4, SEQ ID NO: 11 |
| intergenic sequence | 4403-4949 | — |
| fusion protein ORF | 4950-581 | SEQ ID NO: 5, SEQ ID NO: 12 |
| intergenic sequence | 6582-6958 | — |
| hemagglutinin ORF | 6959-8746 | SEQ ID NO: 6, SEQ ID NO: 13 |
| intergenic sequence | 8747-8887 | — |
| polymerase ORF | 8888-15496 | SEQ ID NO: 7, SEQ ID NO: 14 |
| 5' UTR | 15497-16047 | — |

TABLE 1-continued

Overview of the genome of a paramyxovirus according to the present invention

| Genome region | nucleotide position (in SEQ ID NO: 1) | corresponding polypeptide sequences |
| --- | --- | --- |

SEQ ID NOs:2 to 7 represent the polypeptide sequences of the open reading frames of SEQ ID NO:1 (Gordon strain) and SEQ ID NOs:9 to 14 represent the polypeptide sequences of the open reading frames of SEQ ID NO:8 (strain TV25).

The invention thus relates in one aspect to a nucleic acid comprising a polynucleotide having a nucleotide sequence selected from the group consisting of:
 (a) a nucleotide sequence according to SEQ ID NO:1 or SEQ ID NO:8;
 (b) a nucleotide sequence being at least 80%, at least 85%, at least 90%, at least 91%, at least 92%, at least 93%, at least 94%, at least 95%, at least 96%, at least 97%, at least 98%, at least 99% identical to SEQ ID NO:1 or SEQ ID NO:8;
 (c) a nucleotide sequence encoding a polypeptide having an amino acid sequence selected from the group consisting of SEQ ID NO:2, SEQ ID NO:9 (i.e. the nucleocapsid protein), SEQ ID NO:3, SEQ ID NO:10 (i.e. the phosphoprotein), SEQ ID NO:4, SEQ ID NO:11 (i.e. the matrix protein), SEQ ID NO:5, SEQ ID NO:12 (i.e. the fusion protein), SEQ ID NO:6, SEQ ID NO:13 (i.e. the hemagglutinin) SEQ ID NO:7 and SEQ ID NO:14 (i.e. the polymerase);
 (d) a nucleotide sequence encoding a polypeptide having an amino acid sequence which is
  (i) at least 90%, preferably at least 95%, more preferably at least 98% identical to SEQ ID NO:2,
  (ii) at least 76%, preferably at least 80%, more preferably at least 90%, more preferably at least 95% and most preferably at least 98% identical to SEQ ID NO:3,
  (iii) at least 92%, preferably at least 95%, more preferably at least 98% identical to SEQ ID NO:4,
  (iv) at least 89%, preferably at least 90%, more preferably at least 95%, more preferably at least 98% identical to SEQ ID NO:5,
  (v) at least 86%, preferably at least 90%, more preferably at least 95%, most preferably at least 98% identical to SEQ ID NO:6 and/or
  (vi) at least 91%, preferably at least 95%, more preferably at least 98% identical to SEQ ID NO:7; and
 (e) the complementary strand of any of the nucleotide sequences of (a) to (d).

The nucleic acids of the present invention code for the genome of a feline paramyxovirus. Said paramyxovirus is in one embodiment able to induce an infection, particularly an infection of the urogenital system, more in particular an infection of the urinary system, or renal disease, particularly chronic renal disease in a human or non-human mammal, preferably a felid, canid, rodent or human, most preferably a domestic cat (Felis silvestris catus sometimes also referred to as Felis catus). SEQ ID NOs: 2 to 7 relate to the polypeptide gene products of the six open reading frames (ORFs) in SEQ ID NO:1. SEQ ID NOs: 9 to 14 relate to the polypeptide gene products of the six open reading frames (ORFs) in SEQ ID NO:8. Hence, the polypeptide encoded by the nucleic acid of item (d)(i) is a viral nucleocapsid protein, the polypeptide encoded by the nucleic acid of item (d)(ii) is a viral phosphoprotein, the polypeptide encoded by the nucleic acid of item (d)(iii) is a viral matrix protein, the polypeptide encoded by the nucleic acid of item (d)(iv) is a viral fusion protein, the polypeptide encoded by the nucleic acid of item (d)(v) is a viral hemagglutinin and the polypeptide encoded by the nucleic acid of item (d)(vi) is a viral polymerase.

Preferably herein, the nucleic acid of the invention comprises
 (i) a nucleic acid sequence encoding a polypeptide having an amino acid sequence which is at least 90% identical to SEQ ID NO:2,
 (ii) a nucleic acid sequence encoding a polypeptide having an amino acid sequence which is at least 76% identical to SEQ ID NO:3,
 (iii) a nucleic acid sequence encoding a polypeptide having an amino acid sequence which is at least 92% identical to SEQ ID NO:4,
 (vi) a nucleic acid sequence encoding a polypeptide having an amino acid sequence which is at least 89% identical to SEQ ID NO:5,
 (v) a nucleic acid sequence encoding a polypeptide having an amino acid sequence which is at least 86% identical to SEQ ID NO:6, and/or
 (vi) a nucleic acid sequence encoding a polypeptide having an amino acid sequence which is at least 91% identical to SEQ ID NO:7.

Also part of the invention is a polypeptide having an amino acid sequence
 (a) selected from the group consisting of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13 and SEQ ID NO:14; or
 (b) an amino acid sequence which is at least 90%, preferably at least 95%, more preferably at least 97%, most preferably at least 98% identical to SEQ ID NO:2,
 (c) an amino acid sequence which is at least 76%, preferably at least 80%, more preferably at least 85%, more preferably at least 90%, more preferably at least 95%, more preferably at least 97%, most preferably at least 98% identical to SEQ ID NO:3,
 (d) an amino acid sequence which is at least 92%, preferably at least 95%, more preferably at least 97%, most preferably at least 98% identical to SEQ ID NO:4,
 (e) an amino acid sequence which is at least 89%, preferably at least 90%, more preferably at least 95%, more preferably at least 97%, most preferably at least 98% identical to SEQ ID NO:5,
 (f) an amino acid sequence which is at least 86%, preferably at least 90%, more preferably at least 95%, more preferably at least 97%, most preferably at least 98% identical to SEQ ID NO:6, or
 (g) an amino acid sequence which is at least 91%, preferably at least 95%, more preferably at least 97%, most preferably at least 98% identical to SEQ ID NO:7.

The polypeptide may in some embodiments comprise one or more post-translational modifications such as a glycosylation.

The invention also pertains to a feline paramyxovirus the genome of which comprises a ribonucleic acid complementary to the nucleic acid of the invention as set out herein above. In particular, the invention relates to the paramyxovirus which has been deposited on 16 Aug. 2016 at the Collection Nationale de Cultures de Microorganismes (CNCM), Institut Pasteur, 25 Rue du Docteur Roux, F-75724 Paris Cedex 15, France under accession no. CNCM I-5123. This strain is herein designated the 'Gordon' strain. The invention further pertains to any descendant of the paramyxovirus deposited as CNCM I-5123, whereby said descendant may be attenuated or non-attenuated. Hence, the paramyxovirus of the present invention may be selected from the group consisting of: a paramyxovirus deposited as CNCM I-5123, a descendant of the paramyxovirus deposited as CNCM I-5123, an attenuated descendant of the paramyxovirus deposited as CNCM I-5123, and a paramyxovirus strain having the same characteristics as the paramyxovirus deposited as CNCM I-5123.

The paramyxovirus of the present invention preferably comprises one or more polypeptide(s) having an amino acid sequence
(a) selected from the group consisting of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13 and SEQ ID NO:14; or
(b) an amino acid sequence which is at least 90%, preferably at least 95%, more preferably at least 97%, most preferably at least 98% identical to SEQ ID NO:2,
(c) an amino acid sequence which is at least 76%, preferably at least 80%, more preferably at least 85%, more preferably at least 90%, more preferably at least 95%, more preferably at least 97%, most preferably at least 98% identical to SEQ ID NO:3,
(d) an amino acid sequence which is at least 92%, preferably at least 95%, more preferably at least 97%, most preferably at least 98% identical to SEQ ID NO:4,
(e) an amino acid sequence which is at least 89%, preferably at least 90%, more preferably at least 95%, more preferably at least 97%, most preferably at least 98% identical to SEQ ID NO:5,
(f) an amino acid sequence which is at least 86%, preferably at least 90%, more preferably at least 95%, more preferably at least 97%, most preferably at least 98% identical to SEQ ID NO:6, and/or
(g) an amino acid sequence which is at least 91%, preferably at least 95%, more preferably at least 97%, most preferably at least 98% identical to SEQ ID NO:7.
Preferably, the paramyxovirus of the present invention comprises the polypeptides of SEQ ID NO:2, SEQ ID NO:3, SEQ ID NO:4, SEQ ID NO:5, SEQ ID NO:6 and SEQ ID NO:7 or the polypeptides of SEQ ID NO:9, SEQ ID NO:10, SEQ ID NO:11, SEQ ID NO:12, SEQ ID NO:13 and SEQ ID NO:14 or all the polypeptides of items (b) to (g).

In accordance with the present invention, the term "at least % identical to" in connection with nucleic acid sequences or amino acid sequences describes the number of matches ("hits") of identical nucleic acids or amino acids of two or more aligned sequences as compared to the number of residues making up the overall length of the sequences (or the overall compared part thereof). In other terms, using an alignment, for two or more sequences or subsequences, the percentage of residues that are the same (e.g. at least 84%, 85%, 86%, 87%, 88%, 89%, 90%, 91%, 92%, 93%, 94%, 95%, 96%, 97%, 98% or 99% identity) may be determined, when the (sub)sequences are compared and aligned for maximum correspondence over a window of comparison, or over a designated region as measured using a sequence comparison algorithm as known in the art, or when manually aligned and visually inspected.

It is well known in the art how to determine percent sequence identity between/among sequences using, for example, algorithms such as those based on CLUSTALW computer program (Thompson Nucl. Acids Res. 2 (1994), 4673-4680) or FASTA (Pearson and Lipman, Proc. Natl. Acad. Sci., 1988, 85; 2444). Although the FASTA algorithm typically does not consider internal non-matching deletions or additions in sequences, i.e., gaps, in its calculation, this can be corrected manually to avoid an overestimation of the % sequence identity. CLUSTALW, however, does take sequence gaps into account in its identity calculations. Also available to those having skill in this art are the BLAST and BLAST 2.0 algorithms (Altschul, Nucl. Acids Res., 25 (1977), 3389). The BLASTN program for nucleic acid sequences uses as default a word length (W) of 11, an expectation (E) of 10, M=5, N=4, and a comparison of both strands. For amino acid sequences, the BLASTP program uses as default a word length (W) of 3, and an expectation (E) of 10. The BLOSUM62 scoring matrix (Henikoff, Proc. Natl. Acad. Sci., 89 (1989), 10915) uses alignments (B) of 50, expectation (E) of 10, M=5, N=4, and a comparison of both strands. All those programs may be used for the purposes of the present invention. However, preferably the BLAST program is used. Accordingly, all the nucleic acid molecules or amino acid sequences having the prescribed function and further having a sequence identity of at least 84%, 85%, 86%, 87%, 88%, 89%, 90%, 91%, 92%, 93%, 94%, 95%, 96%, 97%, 98% or 99% as determined with any of the above recited or further programs available to the skilled person and preferably with the BLAST program fall under the scope of the invention.

In one aspect said paramyxovirus is able to induce an infection, particularly an infection of the urogenital system, more in particular an infection of the urinary system, or renal/kidney disease, particularly chronic renal disease in a human or non-human mammal, most preferably tubulo-interstitial nephritis (TIN) in a subject, preferably a mammal, more preferably in a feline, even more preferably in a domestic cat (*Felis silvestris catus*).

However, the paramyxovirus of the present invention may also be attenuated relative to the paramyxovirus which has been deposited on 16 Aug. 2016 at the Collection Nationale de Cultures de Microorganismes (CNCM), Institut Pasteur, 25 Rue du Docteur Roux, F-75724 Paris Cedex 15, France under accession no. CNCM I-5123, e.g. for use in an immunogenic composition or vaccine.

Methods for attenuating the paramyxovirus of the present invention are known to the skilled person. Traditional methods of attenuating viruses may, for example, comprise the continuous passaging of the clinically isolated virus in embryonic hen eggs and chicken embryos and/or chicken embryo cell cultures (e.g. see Buynak et al. (1966), Experimental Biology and Medicine, 123(3), 768-775) or the adaption of wild-type virus to cell lines of foreign species and serial passaging to reduce virulence and pathogenicity (e.g. see Enders et al. (1960), New England Journal of Medicine, 263(4), 153-159). More recent approaches are, for instance, based on restricting the virulence through engineering the codon pair bias of the wild-type virus (e.g. see Coleman et al. (2008), Science, 320(5884), 1784-1787) or the genetic modification of the clinically isolated virus strains by deletion of some viral proteins which are responsible for virulence and pathogenicity (e.g. see Xu et al. (2014) Journal of virology, 88(5), 2600-2610).

Hence, the invention further relates to the use of the nucleic acid molecule according to the invention (particularly the nucleic acid according to SEQ ID NO:1 or SEQ ID NO:8 or the nucleic acid which is at least 80% identical to SEQ ID NO:1 or SEQ ID NO:8) for producing an attenuated feline paramyxovirus, wherein one or more mutations are introduced into the nucleic acid molecule. Consequently, the invention also provides a method of producing an attenuated feline paramyxovirus comprising the step of introducing one or more mutations into the nucleic acid molecule according to the invention, particularly to the nucleic acid according to SEQ ID NO:1 or SEQ ID NO:8 or the nucleic acid which is at least 80% identical to SEQ ID NO:1 or SEQ ID NO:8.

The term "attenuated" paramyxovirus, as described herein, is in particular directed to a paramyxovirus which is attenuated in vitro and/or in vivo, more particular in susceptible cell lines and/or the host.

As mentioned herein, "attenuated" particularly relates to a reduced virulence of a pathogen, in particular of the paramyxovirus, wherein "virulence" is understood to be the degree of pathogenicity, and wherein "pathogenicity" is directed to the ability of the pathogen to induce clinical signs in the host or the offspring of the host. Possible clinical signs of the infection with the paramyxovirus of the present invention comprise, for example, an increased thirst, increased urination, weight loss, decreased appetite, lethargy, and vomiting in the subject. Possible laboratory findings associated with an infection with the paramyxovirus of the present invention in a subject comprise, for example, increased levels of creatinine and symmetric dimethyl arginine (SDMA). Possible histological findings associated with an infection with the paramyxovirus of the present invention in a subject comprise, for example, cortical and medullary scarring, tubular degeneration, interstitial inflammation due to infiltration of primarily lymphocytes, plasma cells, macrophages and granulocytes.

The term "host", as used herein, is in particular directed to mammals infectable with the feline paramyxovirus of the present invention, in particular the subjects as defined below, preferably a feline, more preferably a domestic cat.

In the context of the present invention, the term "subject" (e.g. the subject which is susceptible to an infection with the paramyxovirus of the invention or which is treated with the vaccine of the present invention or which is diagnosed in the context of the present invention) is an animal, preferably a mammal, particularly a mammal selected from the group consisting of a member of the orders of Carnivora (preferred), Rodentia, Chiroptera and Primates, more preferably of the family of Felidae, Canidae, Cricetidae, Muridae, or Hominidae. Preferably, the subject is a member of the family of Felidae, particularly of the genera of *Felis* (which is preferred herein), *Lynx, Panthera*, Neofelis, Caracal, *Leopardus, Puma, Acinonyx*, Prionailurus, and Otocolobus. Canidae include for example the genera *Canis* and *Vulpes*, e.g. *Canis lupus*, preferably *Canis lupus familiaris* (the domestic dog). However, the invention is not limited to these species, orders and families.

The *Felis* genus includes for example the species of *Felis silvestris*, e.g. *Felis silvestris silvestris* (European wildcat), feral cat, preferably *Felis silvestris catus* (also known as *Felis catus*, i.e. the domestic cat), *Felis chaus, Felis nigripes, Felis* margarita, and *Felis bieti*.

The genus *Panthera* e.g. includes Tiger (*Panthera tigris*), Lion (*Panthera leo*), Jaguar (*Panthera onca*), Leopard (*Panthera pardus*), Snow leopard (*Panthera uncial*), and Liger.

Other Felidae include but are not limited to *Lynx lynx, Lynx rufus, Acinonyx jubatus* (Cheetah), *Puma concolor* (Cougar), *Leopardus pardalis* (Ocelot).

Mammals of the family of Hominidae include Bornean orangutan (*Pongo pygmaeus*), Sumatran orangutan (*Pongo abelii*), Gorilla gorilla, Chimpanzee (*Pan troglodytes*), Bonobo (*Pan paniscus*), and *Homo sapiens sapiens* (human).

Chiroptera (bats) include Megachiroptera (megabats) and Microchiroptera (microbats). The mammal may also be a typical pet species, e.g. guinea pig (*Cavia porcellus*), domestic rabbit (*Oryctolagus cuniculus*), fancy mouse (*Mus musculus*), fancy rat (*Rattus norvegicus*), ferret (*Mustela putorius furo*), or Syrian hamster (*Mesocricetus auratus*). Mammalian pet and zoo animals are preferred herein. The mammal is preferably a felid, canid, rodent, human or bat, more preferably a felid ("feline"), most preferably a domestic cat.

The present invention further provides a DNA construct comprising the nucleic acid molecule according to the invention, wherein said DNA construct is in particular a DNA vector such as a plasmid. DNA vectors or plasmids into which the nucleotide molecule of the present invention can be inserted will be recognized by those of ordinary skill in the art. The DNA construct, as described herein, is preferably an isolated DNA construct. As used herein, the term "comprising the nucleic acid molecule" or "comprising a DNA molecule", respectively, is in particular understood to be equivalent to the term "comprising the sequence of the nucleic acid molecule" or "comprising the sequence of a DNA molecule", respectively. Thus, the invention also relates to a vector comprising said nucleic acid of the invention and a host cell comprising said vector.

Further, the present invention provides a RNA transcript of the DNA construct described herein, wherein said RNA transcript is preferably an isolated RNA transcript. The present invention also provides a cell transfected with the DNA construct described herein, wherein said cell is preferably an isolated cell. Thus, the present invention also provides a feline paramyxovirus produced by the aforementioned cell, wherein said feline paramyxovirus is preferably an isolated feline paramyxovirus. Further, the present invention provides a cell transfected with the RNA transcript mentioned herein, wherein said cell is preferably an isolated cell. Hence, the present invention also provides a feline paramyxovirus produced by the aforementioned cell, wherein said feline paramyxovirus is preferably an isolated feline paramyxovirus. Host cells in which the paramyxovirus of the present invention or the polypeptides of the invention can be produced include but are not limited to cells selected from HEK293, HEK293T, Vero, CrFK, LLC-MK2, BHK21, CHO, BSR-T7/5, MA-104 and HELA cells.

The present invention further provides a feline paramyxovirus whose genome comprises the nucleic acid molecule of the present invention or whose genome comprises an RNA molecule encoded by a nucleic acid molecule of the present invention, wherein said feline paramyxovirus is preferably an isolated feline paramyxovirus. In another aspect, the present invention provides a method for producing a feline paramyxovirus, said method comprising transfecting a cell with the DNA construct described herein or the nucleic acid of the invention.

The paramyxovirus according to the current invention may also be a chimeric virus, i.e. a paramyxovirus of the present invention the genome of which comprises a heterologous nucleic acid sequence. The chimeric virus may for example be encoded by a vector which further comprises a heterologous nucleotide sequence. In accordance with the invention a chimeric virus may, thus, be encoded by a viral vector to which heterologous nucleotide sequences have been added, inserted or substituted for native or non-native sequences. A chimeric virus may for instance be used for the generation of recombinant vaccines protecting against two or more viruses, e.g. two or more strains of paramyxoviruses. Attenuated and replication-defective viruses may be of used for vaccination purposes with live vaccines. The heterologous sequence may encode an antigen of any infectious pathogen or an antigen associated with any disease that is capable of eliciting an immune response.

The invention further relates to an antibody that is specific for the paramyxovirus of the invention and/or the polypeptide of the invention. The term "antibody" as used herein, unless indicated otherwise, is used broadly to refer to both, antibody molecules and a variety of antibody-derived molecules. Such antibody derived molecules comprise at least one variable region (either a heavy chain or a light chain variable region), as well as individual antibody light chains, individual antibody heavy chains, chimeric fusions between antibody chains and other molecules, and the like. Functional immunoglobulin fragments according to the present invention may be Fv, scFv, disulfide-linked Fv, Fab, and F(ab')$_2$. The antibodies may for example be IgMs, IgDs, IgEs, IgAs or IgGs (e.g. IgG1, IgG2, IgG2b, IgG3 or IgG4 or the respective IgG subclasses in the respective species). Also encompassed by the term "antibody" are polyclonal antibodies, monoclonal antibodies ("mAbs"), chimeric monoclonal antibodies; humanized antibodies, genetically engineered monoclonal antibodies. For example, such antibodies may be obtained by administering a non-human mammal such as a mouse or a rabbit with the (full) paramyxovirus of the invention or a part thereof (e.g. a polypeptide of the invention or antigenic fragment thereof) and subsequently isolating the antibodies or antibody-producing cells. Alternatively, antibody libraries can be screened for such antibodies. Methods for producing human (or feline or canine or any other desired species), humanized (or caninized, felinized or any other species) or chimeric antibodies are well-known in the art. For example, phage display and xenomouse-based technologies can be used for generating human, feline, canine or other species-based monoclonal antibodies. Antibodies generated or identified in accordance with the methods described herein above may be tested for specificity for antigens of the feline paramyxovirus of the invention and/or the ability to neutralize the feline paramyxovirus of the present invention using biological assays known in the art including. Preferred herein are antibodies that are specific against a surface epitope of the feline paramyxovirus of the present invention, particularly antibodies against the hemagglutinin protein (polypeptide according to SEQ ID NO:6 or SEQ ID NO:13) or the fusion protein (polypeptide according to SEQ ID NO:5 or SEQ ID NO:12). In the context of the antibodies of the present invention the terms "specific for" and "specific binding" refer to antibodies raised against the molecule of interest or a fragment thereof. An antibody is considered to be specific, if its affinity towards the molecule of interest or the aforementioned fragment thereof is at least 10-fold higher, preferably 50-fold higher, more preferably 100-fold higher, most preferably at least 1000-fold higher than towards other molecules comprised in a sample containing the molecule of interest. The antibodies of the invention may be used to detect the feline paramyxovirus of the invention in a sample and/or for diagnostic purposes, e.g. to monitor the efficacy of a therapy and/or disease progression.

In a further aspect, the present invention relates to immunogenic compositions and vaccines against the paramyxovirus of the present invention. Said vaccines may e.g. comprise (a) a paramyxovirus according to the present invention;
(b) a nucleic acid according the present invention;
(c) a polypeptide according to the present invention; or
(d) an antibody according to the present invention;
and a pharmaceutically acceptable carrier or excipient, preferably said carrier is suitable for intradermal or intramuscular application, optionally said vaccine further comprises an adjuvant.

Said immunogenic composition may e.g. comprise
(a) a nucleic acid according to claim 1;
(b) a polypeptide according to claim 4;
(c) a polypeptide according to claim 4, and which is fused to a heterologous or autologous (poly-)peptide
and optionally a pharmaceutically acceptable carrier or excipient, preferably said carrier is suitable for intradermal or intramuscular application, optionally said vaccine further comprises an adjuvant.

An "immunogenic composition" as used herein refers to a composition of matter that comprises at least one paramyxovirus, nucleic acid, polypeptide or antibody according to the present invention, or an immunogenic portion thereof, that elicits an immunological response (cellular or antibody-mediated immune response) in the host to the composition. In a specific aspect, an immunogenic composition induces an immune response and, more preferably, confers protective immunity against one or more of the clinical signs of a paramyxovirus infection.

The term "vaccine" as used in specific aspects of the present invention refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. The term "vaccine" as used in specific aspects of the present invention describes a modified live, attenuated vaccine for veterinary use comprising antigenic substances and is administered for the purpose of inducing a specific and active immunity against a disease provoked by a paramyxovirus infection, preferably by a feline paramyxovirus infection. In further specific aspects of the present invention the vaccine may inter alia be a live vaccine, a live-attenuated vaccine, an inactivated vaccine, or a conjugate vaccine.

Various physical and chemical methods of inactivation are known in the art. The term "inactivated" refers to a previously virulent or non-virulent virus that has been irradiated (ultraviolet (UV), X-ray, electron beam or gamma radiation), heated (for instance for 30 min to several hours at a temperature between 55° C. and 65° C., e.g. 3 h at 56° C.), or chemically treated to inactivate, kill, such virus while retaining its immunogenicity. In one aspect, the inactivated paramyxoviruses disclosed herein may be inactivated by treatment with an inactivating agent. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus. It is critical to adjust the amount of formalin to ensure that the material is inactivated but not so much that side effects from a high dosage occur.

More particularly, the term "inactivated" in the context of a virus means that the virus is incapable of replication in vivo or in vitro. For example, the term "inactivated" may refer to a virus that has been propagated in vitro, and has then been deactivated using chemical or physical means so that it is no longer capable of replicating. In another example, the term "inactivated" may refer to a virus that has been propagated, and then deactivated using chemical or physical means resulting in a suspension of the virus, fragments or components of the virus, which may be used as a component of a vaccine. As used herein, the terms "inactivated", "killed" or "KV" are used interchangeably.

The term "live vaccine" refers to a vaccine comprising a living, in particular, a living viral active component.

The optionally one or more pharmaceutically acceptable carriers or excipients, as mentioned herein include any and all solvents, dispersion media, coatings, adjuvants, stabilizing agents, diluents, preservatives, antibacterial and antifungal agents, isotonic agents, adsorption delaying agents, and the like. In some aspects, and especially those that include lyophilized immunogenic compositions, stabilizing agents include stabilizers for lyophilization or freeze-drying.

In a preferred aspect, the immunogenic composition of the invention comprises an amount of $10^1$ to $10^7$ viral particles of the attenuated paramyxovirus virus described herein per dose, preferably $10^3$ to $10^6$ particles per dose, more preferably $10^4$ to $10^6$ particles per dose.

In another preferred aspect, the immunogenic composition of the invention comprises an amount of the paramyxovirus according to the invention which is equivalent to a virus titre of at least about $10^3$ $TCID_{50}$/mL per dose, preferably between $10^3$ to $10^5$ $TCID_{50}$/ml per dose.

As used herein, the terms "vaccine" and "vaccine composition" are used interchangeably and in particular refer to a composition that will elicit a protective immune response in a subject that has been exposed to the composition. An immune response may include induction of antibodies and/or induction of a T-cell response.

The vaccine of the present invention may also be a marker vaccine, i.e. a vaccine that allows for the immunological differentiation or segregation of infected from vaccinated animals. For example, the marker vaccine may lack an immunogenic antigen present in the pathogen being vaccinated against (i.e. the paramyxovirus of the invention), thus creating a negative marker of vaccination. Such marker vaccines are also referred to as DIVA or SIVA vaccines ("Differentiation/Segregation of infected from vaccinated animals") in veterinary medicine and are particularly useful for productive livestock such as farm animals.

Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the clinical signs associated with the infection of the pathogen, in the delay of onset of viremia, in a reduced viral persistence, in a reduction of the overall viral load and/or in a reduction of viral excretion.

Thus, an "immune response" in particular means but is not limited to the development in a subset of a cellular and/or antibody-mediated immune response to the composition or vaccine of interest.

The vaccine may in one aspect comprise a fusion protein of the polypeptide of the invention with another peptide or polypeptide. The fusion partner may be a heterologous polypeptide/peptide or an autologous polypeptide/peptide. Heterologous polypeptides that can be fused to the polypeptide of the present invention include but are not limited to a polypeptide of a canarypox virus (in particular for a vaccine in cats), of a myxoma virus (particularly for a vaccine in rabbits) or of a herpes virus.

In another aspect, the present invention relates to a method of detecting the paramyxovirus of the invention in a sample from a subject. The sample in the context of the present invention is a biological sample, particularly a sample of bodily fluid or tissue obtained for the purpose of diagnosis, prognosis, or evaluation of a subject. "Subject" for the purposes of the present invention includes both humans and other mammals. Thus, the methods are applicable to both human diagnostics and veterinary applications. Preferred test samples include whole blood, serum, plasma, urine, saliva, sputum, aspirate, punctate and mucosal swabs. In addition, one of skill in the art would realize that some test samples would be more readily analyzed following a fractionation or purification procedure, for example, separation of whole blood into serum or plasma components. Thus, in a preferred embodiment of the invention the sample is selected from the group comprising a blood sample, a serum sample, a plasma sample, a saliva sample, an aspirate sample, a punctuate sample, a mucosal swab and a urine sample or an extract of any of the aforementioned samples. Also paraffin tissue section samples may be used. Preferably, the sample is a blood or a urine sample, most preferably a serum sample or a plasma sample. Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators. "Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

The detection can either be at the nucleic acid level, i.e. the genomic RNA of the virus is detected in a sample, or on the level of the viral proteins, e.g. using an immunoassay. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays. Also Western Blot assays or lateral flow immunoassays can be used. The viral nucleic acid can be detected e.g. with a reverse transcription and polymerase chain reaction (RT-PCR) using specific primers and/or probes. For example the detection of the nucleic acid can be performed directly in a urine sample of the subject. Also other nucleic acid based samples such as NASBA may be used. PCR assays may for example comprise formats such as nested PCR, semi-nested PCR and quantitative PCR.

In particular, the present invention relates to a method for detecting the paramyxovirus according to the invention in a sample, comprising the steps of
(i) contacting the sample with one or more oligonucleotide primers and/or probes which are specific for a nucleic acid according to the invention (i.e. which preferably hybridize under stringent conditions to said nucleic acid), and
(ii) detecting binding between said paramyxovirus and said one or more oligonucleotide primers and/or probes.

In another particular aspect, the present invention relates to a method for detecting the paramyxovirus according to the invention in a sample, comprising the steps of
(i) contacting the sample with an antibody according to the invention, and
(ii) detecting binding between said paramyxovirus and said antibody.

The method for detecting the paramyxovirus of the present invention can thus be based on the direct detection of the paramyxovirus in a sample. However, it can also be based on a more indirect approach, i.e. by detecting the presence of antibodies against said paramyxovirus in the sample. The presence of antibodies against said paramyxovirus indicates that the subject's immune system has already been in contact with the paramyxovirus such that a corresponding immune response was initiated. In this context, a true infection with the paramyxovirus can be distinguished from a subject vaccinated with a marker vaccine (DIVA, see above) by detecting antigens (i.e. the polypeptide of the invention or an antigenic fragment thereof) in the sample which were deleted from the marker vaccine.

Hence, the invention also pertains to a method for detecting the paramyxovirus according to the invention in a sample, comprising detecting the presence or absence of an antibody against said paramyxovirus in said sample. Suitable approaches for detecting the antibodies in the sample include immunoassays as described above (e.g. ELISA, particularly sandwich ELISA and lateral-flow assays). Hence, the invention also relates to methods (and corresponding kits) for detecting the paramyxovirus of the present invention in a sample, comprising contacting the sample with an antigen of the paramyxovirus and detecting binding of antibodies (if present) in the sample against said paramyxovirus to said antigen. Said antigen is preferably immobilized on a surface. The antibodies bound to said antigen can, for example, be detected by using a secondary detection antibody, e.g. in the case of a feline sample an antibody against feline immunoglobulin (Ig) such as a mouse-anti-cat Ig antibody. Exemplary antigenic epitopes of the polypeptides of the present invention are listed in the following Table 2:

| Polypeptide | Epitopes (residues in sequence) |
| --- | --- |
| Nucleocapsid protein (SEQ ID NO: 2, SEQ ID NO: 9) | 13-29, 38-46, 61-69, 92-97, 106-115, 147-160, 182-192, 242-249, 399-409, 424-483, 496-512 |
| Phospho protein (SEQ ID NO: 3, SEQ ID NO: 10) | 18-30, 39-96, 106-176, 186-202, 208-234, 242-249, 251-268, 270-289, 363-378, 396-411, 425-430, 436-442, |
| Fusion protein (SEQ ID NO: 5, SEQ ID NO: 12) | 210-217, 241-245, 297-302, 394-400, 528-538 |
| Hemagglutinin (SEQ ID NO: 6 SEQ ID NO: 13) | 1-11, 124-131, 140-145, 331-336, 391-398, 409-414, 423-435, 477-482, 521-526, 536-543 |

These epitopes (or fragments of the polypeptides of the invention containing one or more of said epitopes) can, for example, be used to raise antibodies against the paramyxovirus of the present invention.

In another aspect, the present invention relates to a method of diagnosing an infection of a subject with the paramyxovirus of the invention. In particular, the invention also pertains to a method for diagnosing an infection with the paramyxovirus according to the invention in a sample from a subject, preferably a feline, more preferably a domestic cat, comprising a method for detecting the paramyxovirus as described herein above, wherein the presence of said paramyxovirus is indicative for an infection. In another aspect, the present invention pertains to a method for diagnosing an infection with the paramyxovirus according to the invention in a sample from a subject, preferably a domestic cat, comprising a method for detecting an antibody against said paramyxovirus of the invention, wherein the presence of said antibody is indicative for an infection with said paramyxovirus.

In the context of the methods of detecting and methods of diagnosing of the present invention, the detection of the fusion protein or the hemagglutinin of the paramyxovirus is preferred. It is also preferred in one aspect that the viral polymerase is not detected or at least epitopes or regions corresponding to nucleotide residues 10055 to 10560 of the viral genome (SEQ ID NO:1 or 8) are not detected.

In another aspect, the present invention relates to a kit for the detection of the paramyxovirus of the invention. The kit may in one embodiment comprise one or more antibodies specific for the paramyxovirus of the present invention. In another embodiment, the kit may comprise oligonucleotide primers and/or probes for the detection of the paramyxovirus of the invention.

Finally, the invention relates to medical uses of the vaccines, nucleic acids, polypeptide, antibodies and immunogenic compositions of the invention and to methods of treating and/or preventing an infection with the paramyxovirus in a subject. For example, the vaccine or immunogenic composition of the present invention may be used to reduce the clinical signs of an infection with the paramyxovirus, preferably the clinical signs of an infection of the urogenital system, more in particular an infection of the urinary system, or renal/kidney disease, particularly chronic renal disease in a human or non-human mammal, most preferably tubulo-interstitial nephritis (TIN). In particular, the present invention relates to the vaccine or immunogenic composition of the present invention for use in treating or preventing an infection with a paramyxovirus, particularly the feline paramyxovirus of the present invention.

The invention further pertains to the vaccine or immunogenic composition of the invention for use in treating or preventing an infection, particularly an infection of the urogenital system, more in particular an infection of the urinary system, or renal/kidney disease, particularly chronic renal disease in a human or non-human mammal, most preferably tubulo-interstitial nephritis (TIN) in a mammal, preferably a feline, more preferably a domestic cat.

The invention also pertains to a method for treating or preventing an infection with a paramyxovirus, in particular, the feline paramyxovirus according to the invention in a subject, preferably a domestic cat, comprising the step of administering the vaccine or immunogenic composition to said subject.

The invention also relates to a method for treating or preventing a kidney disease, preferably chronic kidney disease, most preferably tubulo-interstitial nephritis (TIN), in a subject, preferably a feline, more preferably a domestic cat, comprising the step of administering the vaccine or immunogenic composition of the present invention to said subject.

In a preferred aspect, the vaccine or immunogenic composition of the present invention is used for preventing an infection with the paramyxovirus of the invention in a subject.

The present invention also relates to the immunogenic composition or the vaccine of the present invention for use in a method of reducing or preventing the clinical signs or disease caused by an infection with a pathogenic paramyxovirus, preferably the paramyxovirus of the invention, in a subject, or for use in a method of treating or preventing an infection with a pathogenic paramyxovirus, preferably the paramyxovirus of the invention, in a subject, wherein preferably said subject is a feline. The present invention further relates to the immunogenic composition or the vaccine of the present invention for use in a method of protecting a subject, preferably a feline, from an infection with a paramyxovirus, preferably the paramyxovirus according to the invention or from clinical signs or disease caused by an infection with a pathogenic paramyxovirus, preferably the paramyxovirus of the invention.

The invention further pertains to a method of immunizing a subject, preferably a feline, against a clinical disease or against clinical signs caused by a paramyxovirus, preferably the paramyxovirus of the invention, in a subject, said method comprising the step of administering to the subject, preferably a feline, an immunogenic composition or vaccine according to the invention, whereby said virus fails to cause clinical signs of paramyxovirus infection but is capable of inducing an immune response that immunizes the subject, preferably the feline, against pathogenic forms of paramyxovirus, preferably the paramyxovirus of the invention.

The invention thus also relates to a method of protecting or reducing the clinical signs of a paramyxovirus infection (preferably with the paramyxovirus of the invention) in a subject, preferably a feline, against a clinical disease or against clinical signs caused by a paramyxovirus, preferably the paramyxovirus of the invention, in a subject, said method comprising the step of administering to the subject, preferably a feline, an immunogenic composition or vaccine according to the invention, whereby said virus fails to cause clinical signs of paramyxovirus infection but is capable of inducing an immune response that immunizes the subject, preferably the feline, against pathogenic forms of paramyxovirus, preferably the paramyxovirus of the invention.

The invention further pertains to a kit for vaccinating a subject, preferably a feline, against diseases associated with and/or reducing the incidence or the severity of one or more clinical signs associated with or caused by a paramyxovirus, preferably the paramyxovirus according to the invention, in a subject comprising:
(a) a dispenser capable of administering a vaccine to the subject, preferably a feline; and
(b) the immunogenic composition or the vaccine according to the invention, and
(c) optionally an instruction leaflet.

All cited patent and non-patent documents are herewith incorporated by reference in their entirety.

Shown is the analysis of the cell culture supernatant from passage 3 of CrFK and LLC-MK2 cells, respectively, after infection with the FPaV-2 "Gordon" strain. M: DNA size standard; 1: cell culture supernatant of CrFK cells; 2: cell culture supernatant of LLC-MK2 cells; 3: water; 4: positive control.

Figure 2:
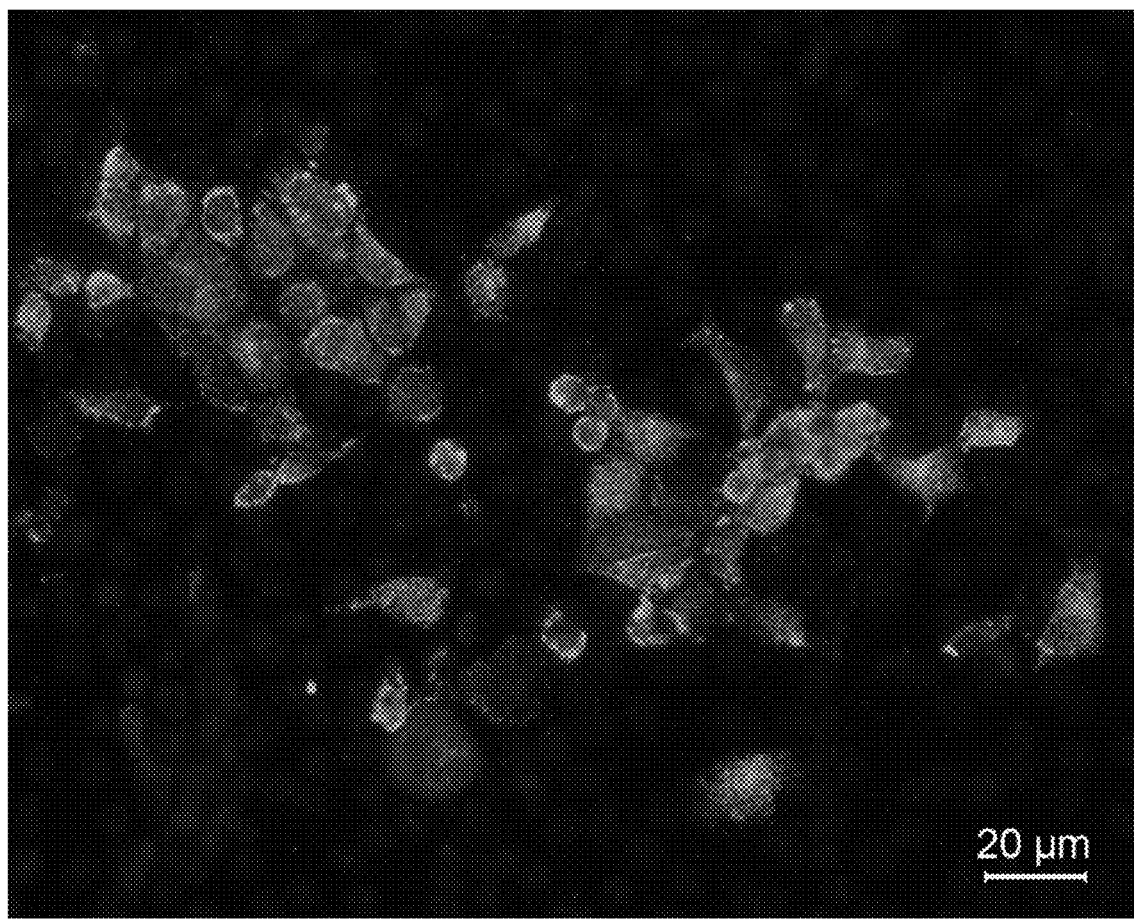

FIG. 2: Immunofluorescence of LLC-MK2 cells infected with the FPaV-2 "Gordon" isolate.

Cell nuclei stained with DAPI. Cells that are FPaV-2 infected show green fluorescence. Magnification: 200×; staining 5 days after infection.

Figure 3:
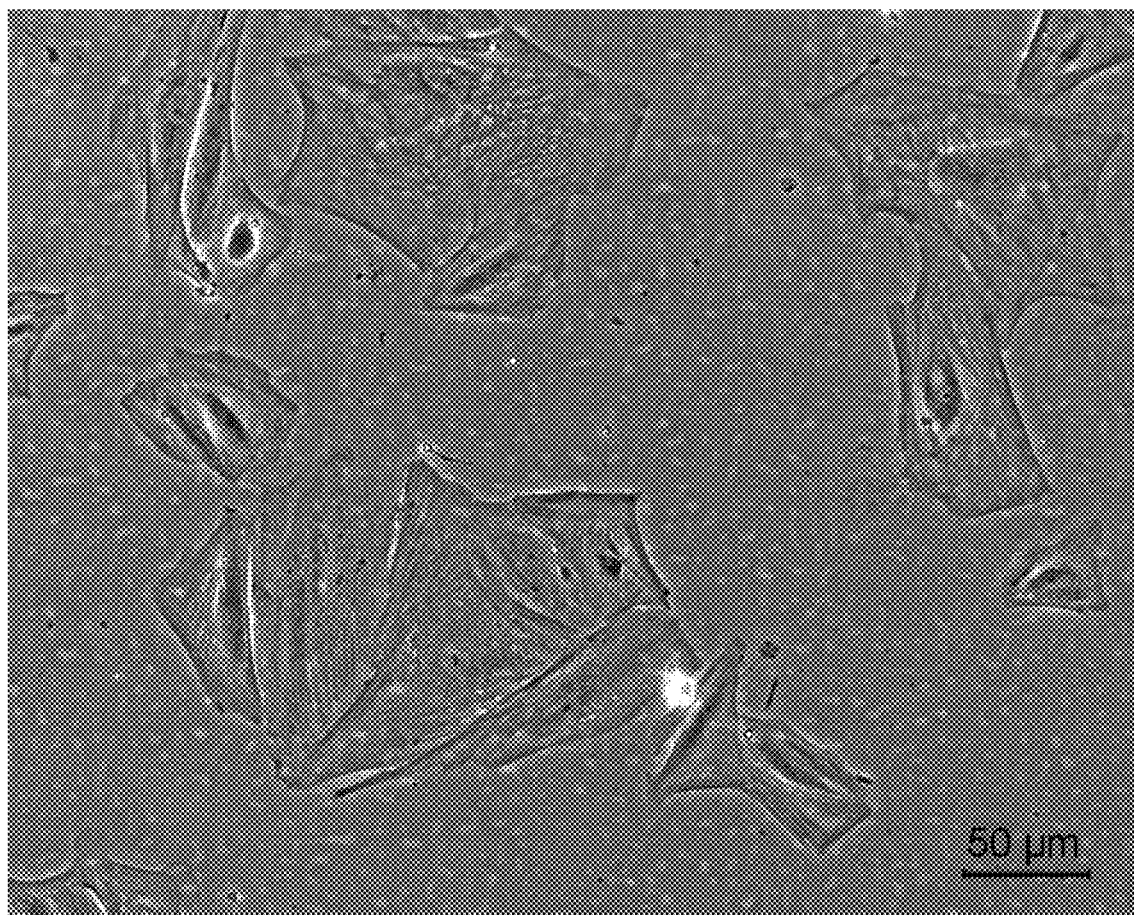

FIG. 3: Isolation of feline primary kidney cells. Magnification: 100×, 48 hours after seeding.

Figure 4:
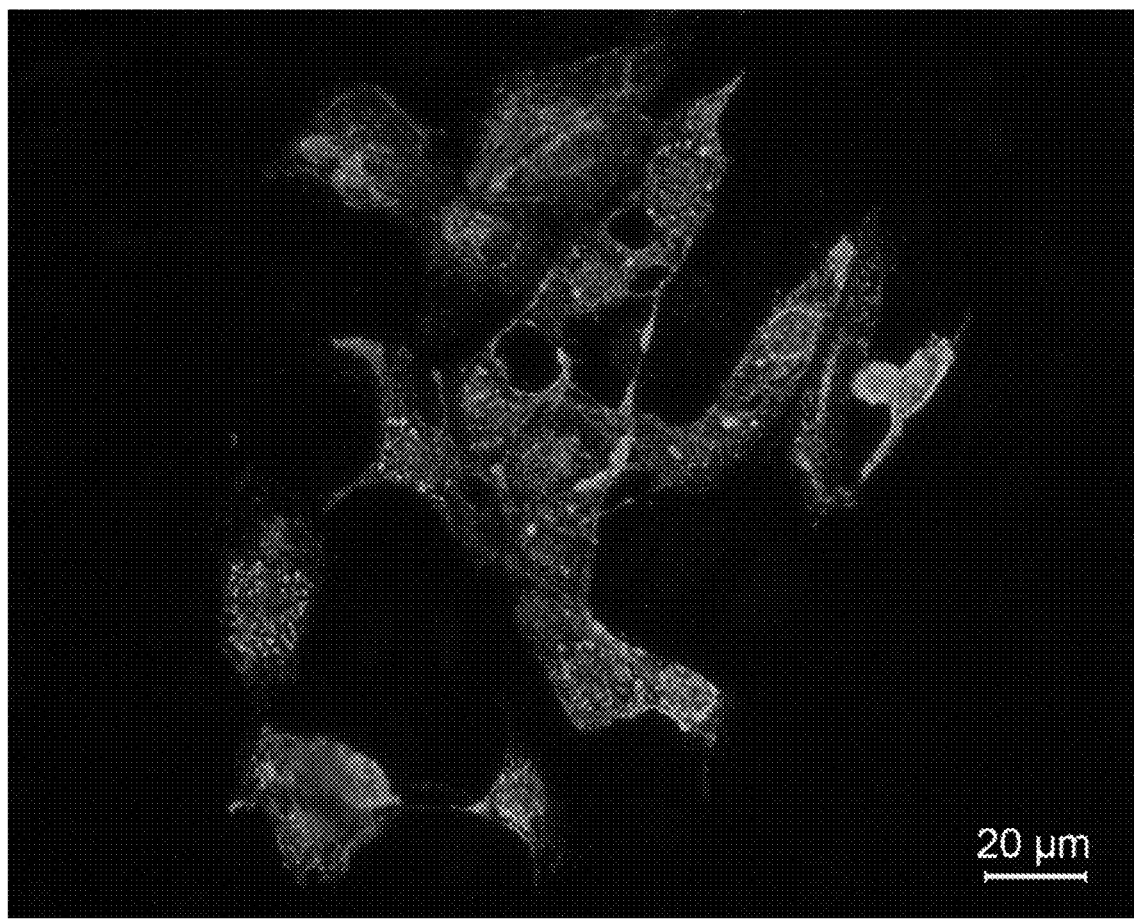

FIG. 4: Infection of feline primary kidney cells with FPaV-2.

Cell nuclei are stained with DAPI. Cells that are FPaV-2 infected show green fluorescence. Magnification: 200×; staining 5 days after infection.

Figure 5:
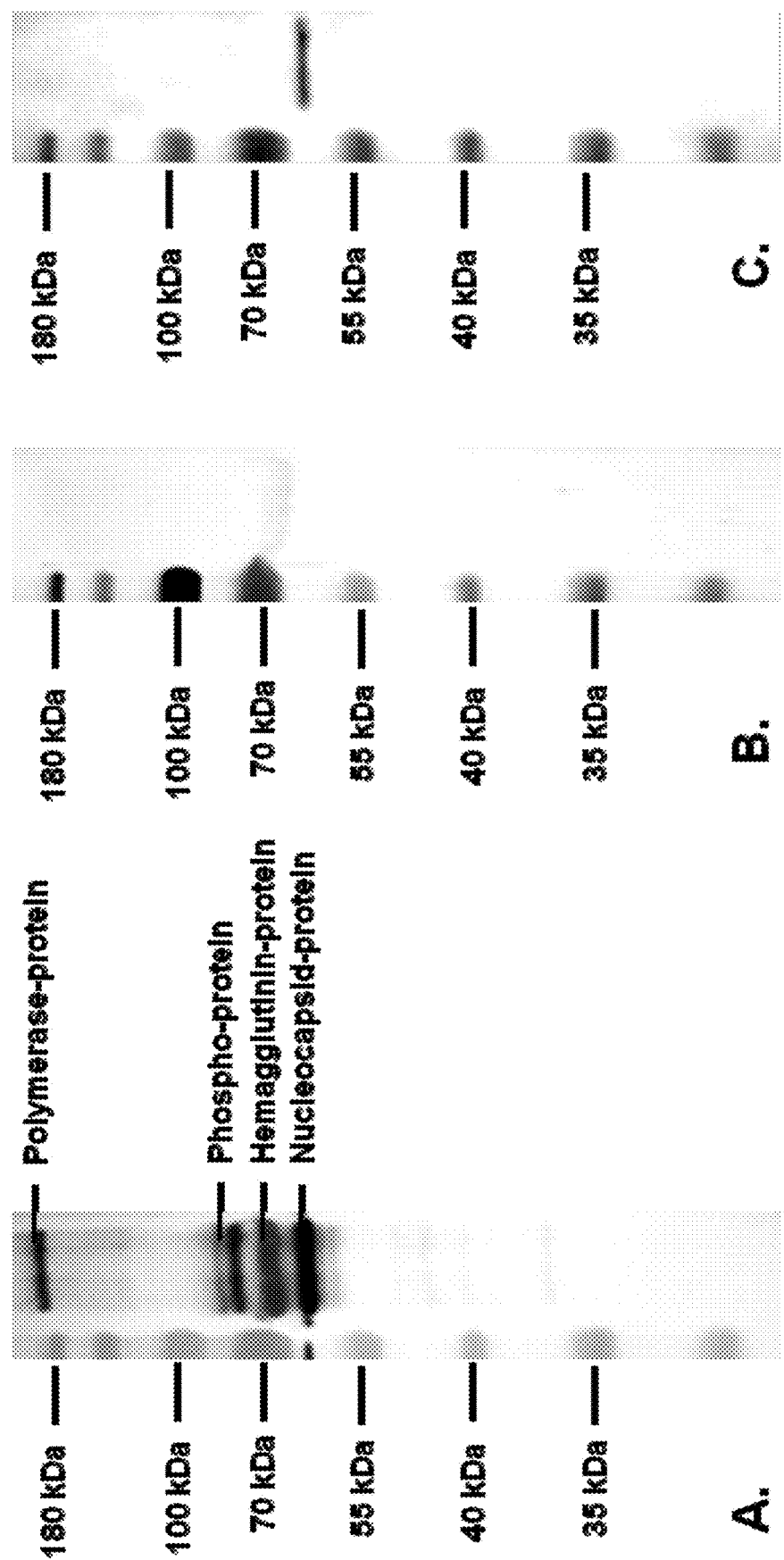

FIG. 5: Antibody diversity of FPaV-2-infected cats.

Western-blot analysis of semi-purified whole FPaV-2 separated by SDS-PAGE and blotted onto a nitrocellulose membrane.
A.=Incubation with 1:100 diluted serum sample from FPaV-2-positive cat 'TV25'.
B.=Incubation with 1:100 diluted sample from paramyxovirus-negative cat.
C.=Incubation with 1:200 diluted anti-nucleocapsid antibody.

Specific reactions to viral proteins are annotated at the right bottom based on their reactivity with target antibodies (nucleocapsid-protein and phospho-protein) or based on their predicted molecular weight (polymerase- and hemagglutinin-protein).

Figure 6:
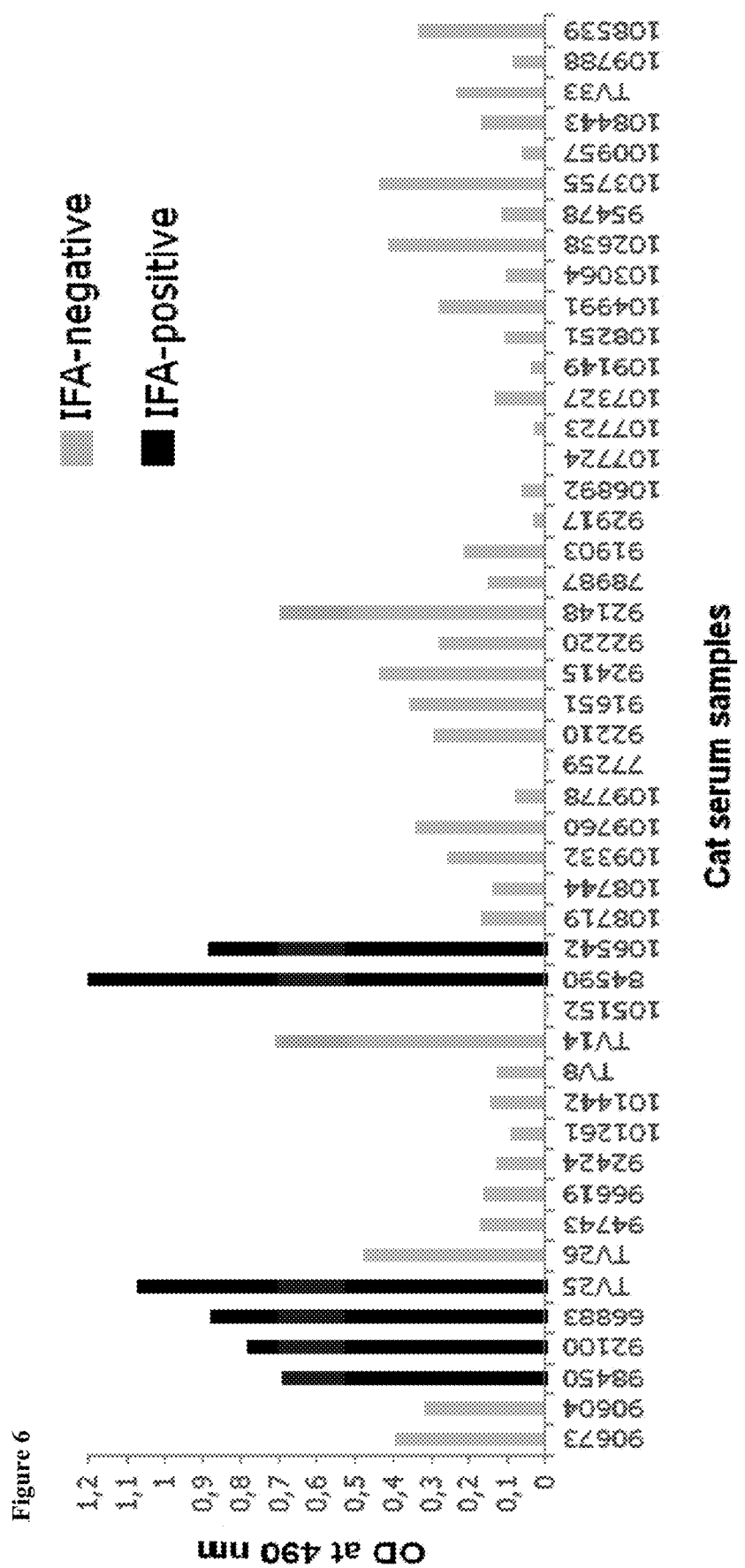

FIG. 6: Development of an ELISA for the detection of FPaV-2 antibodies in cat serum samples.

Cat serum samples were screened in FPaV-2-IFA for the presence of specific antibodies. IFA result was set as gold standard and compared to OD values. Samples having in OD value below 0.5 are defined as FPaV-2 negative, whereas samples with an OD value higher than 0.7 are defined as FPaV-2-positive. Grey box indicates 'borderline'-samples which need to be checked in IFA to evaluate the ELISA result.

Figure 7:
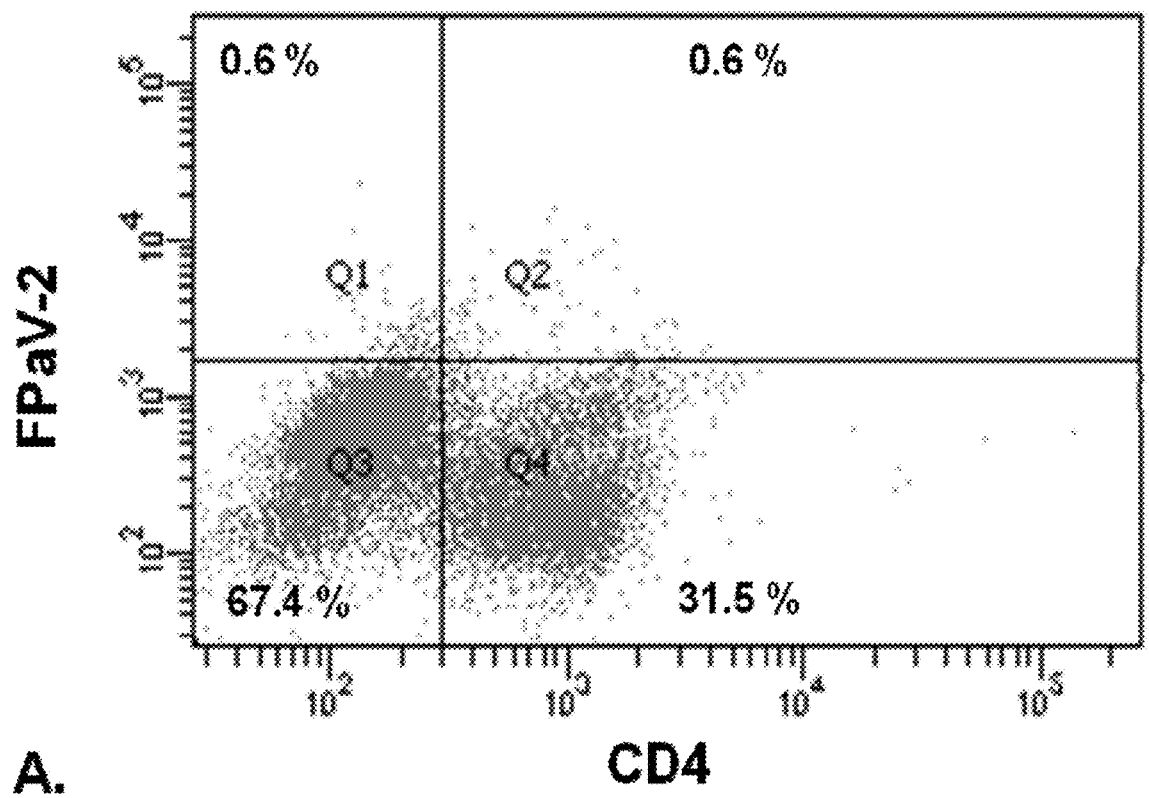
Figure 7:
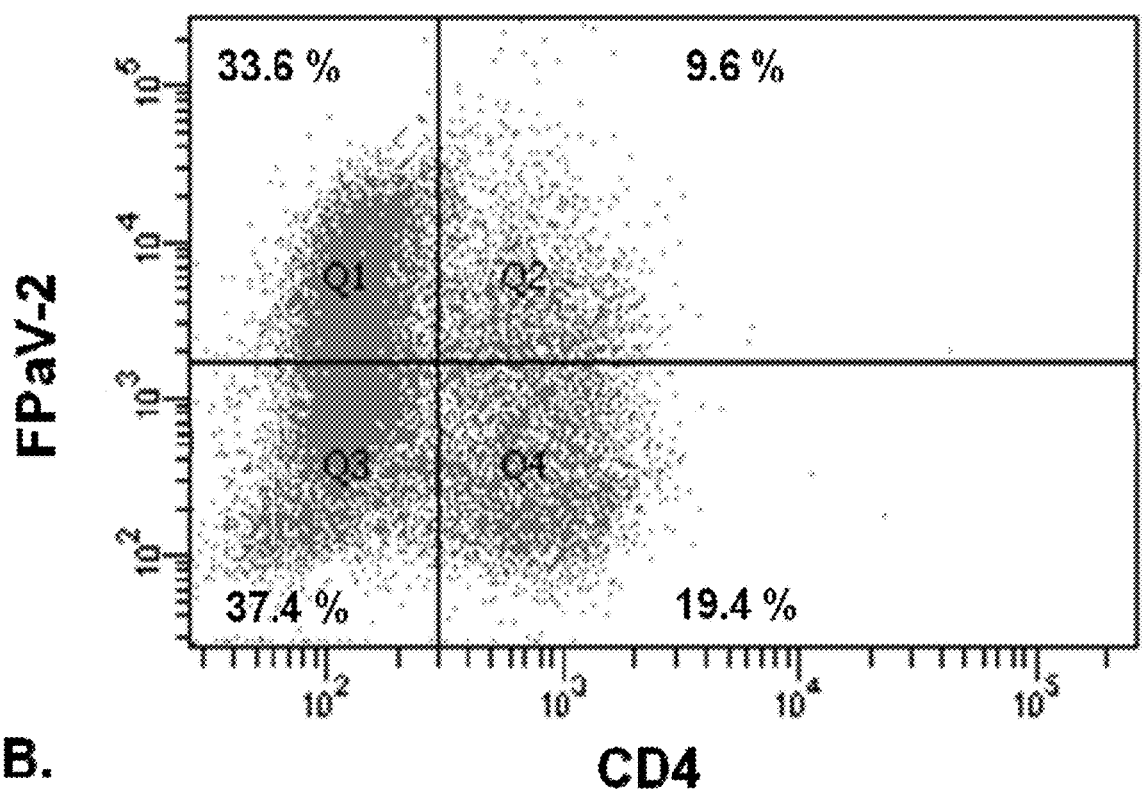
Figure 7:
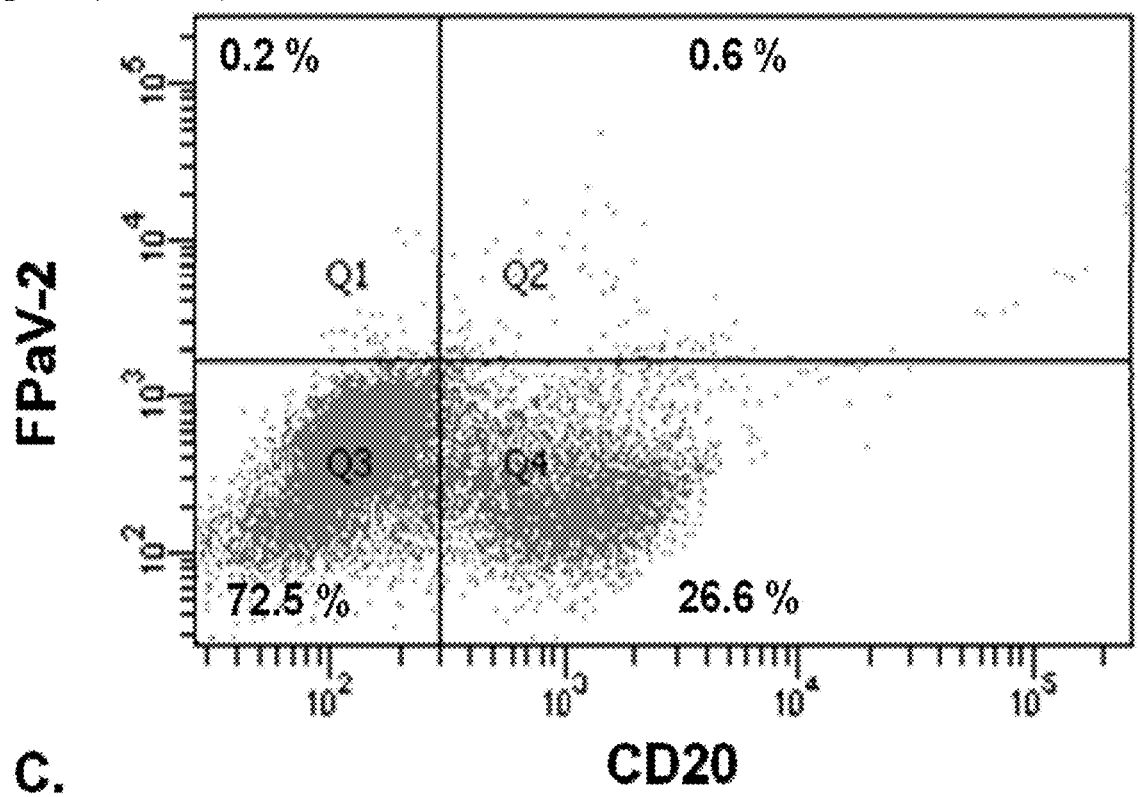
Figure 7:
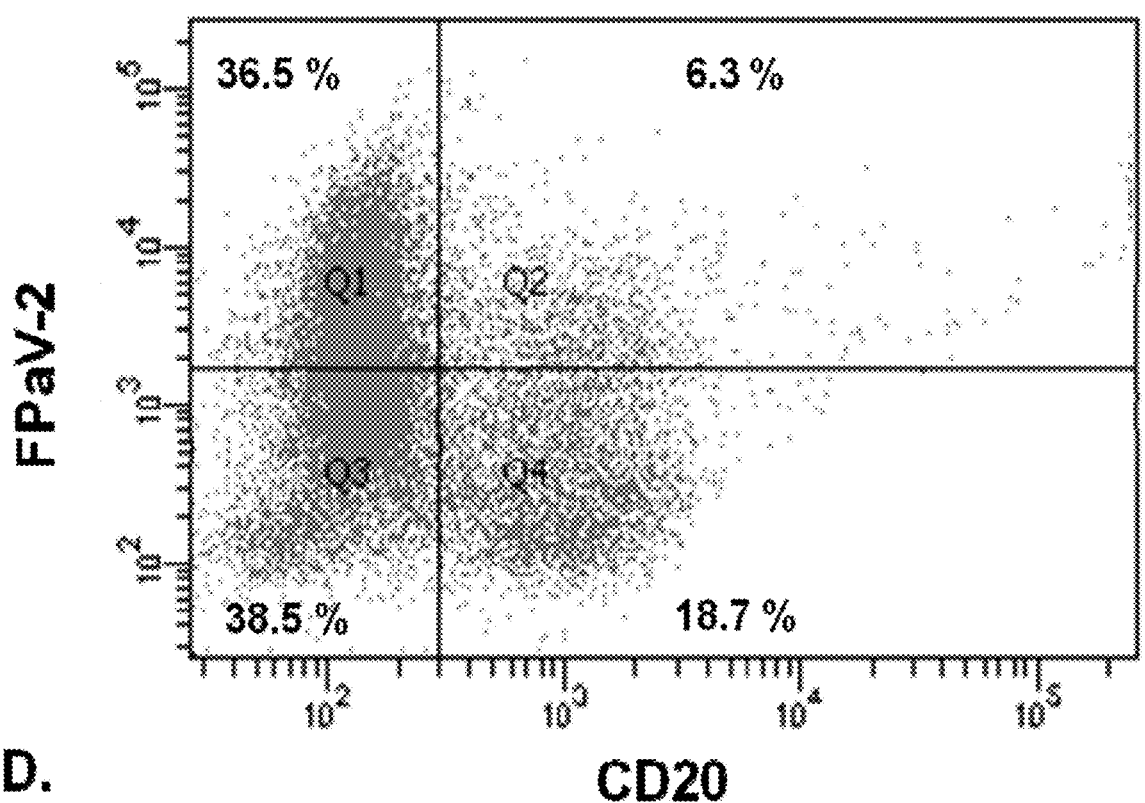

FIG. 7: Primary immune target cells of FPaV-2.

Flow cytometric analysis of PBMCs 48 hours after infection with FPaV-2 at an MOI of 0.1. Cells were stained for surface markers of T-cells (CD4) or B-cells (CD20) and for the intracellular presence of FPaV-2 using a polyclonal nucleocapsid antibody.

A. and C.=Mock-infected PBMCs
B. and D.=FPaV-2-infected PBMCs

Figure 8:
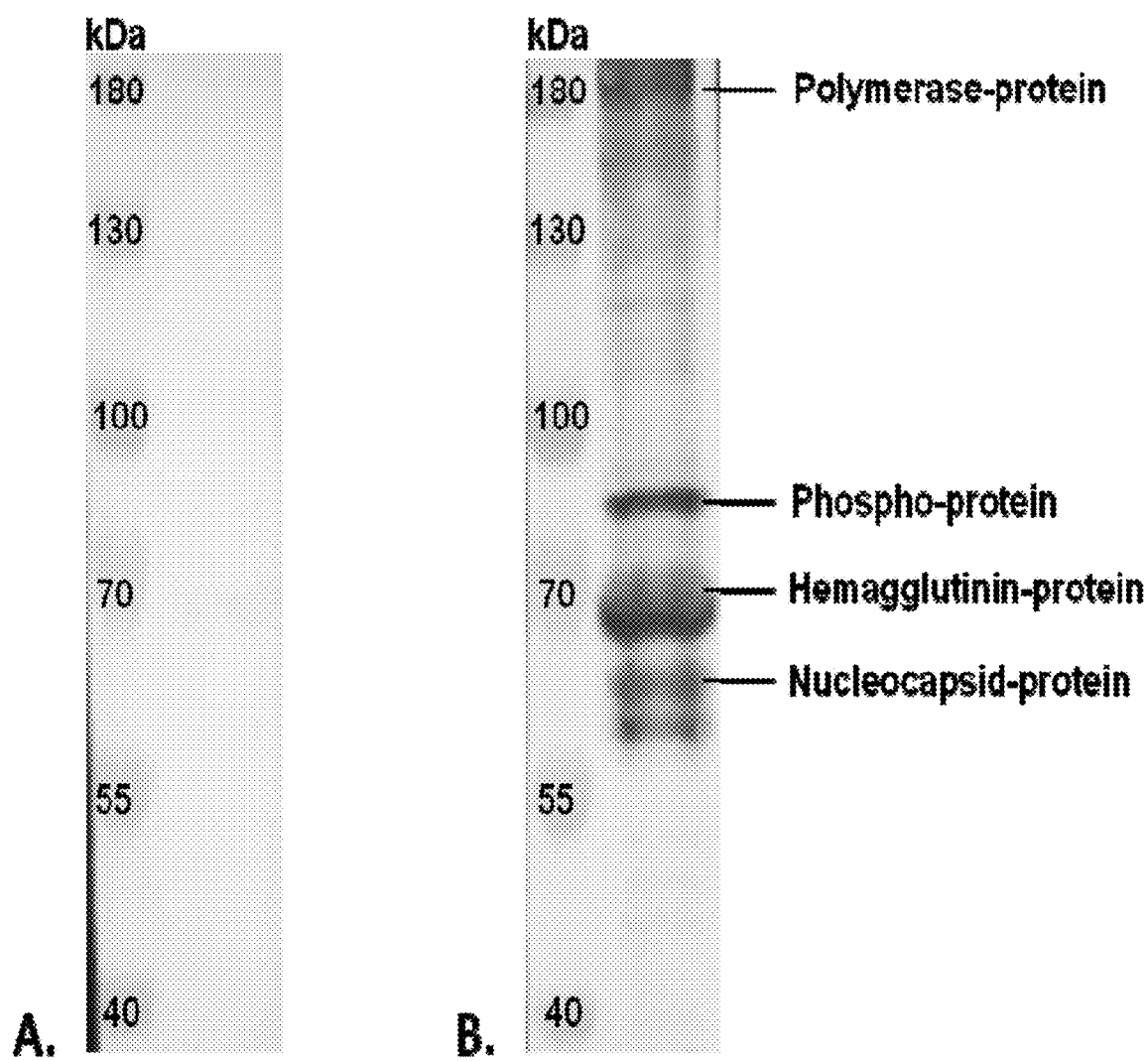

FIG. 8: Western-blot analysis of an FPaV-2-immunized rabbit.

Semi-purified whole FPaV-2 was separated by SDS-PAGE and blotted onto a nitrocellulose membrane.

A.=Incubation with serum sample (1:100 dilution) from rabbit no. 2 before immunization (pre-immune serum).
B.=Incubation with serum sample (1:100 dilution) from rabbit no. 2 five weeks after immunization with heat-inactivated FPaV-2.

Specific reactions to viral proteins are annotated at the right bottom based on reactivity shown in FIG. 5.

In contrast to the pre-immune serum FPaV-2-specific antibodies were detected five weeks after Immunization.

EXAMPLES

Example 1: Detection of FPaV-2

Collection of Sample:
Urine from a 13 year old male cat with a chronic kidney disease is collected and stored on ice.

RNA-Isolation:
RNA is isolated from 300 µl urine using the 'QIAamp Viral RNA Mini Kit' (Qiagen, Hilden), eluted in 50 µl of buffer AVE and stored at −80° C.

RT-PCR:
RT-PCR is performed in a single step using the 'SuperScript III One Step RT-PCR System with Platinum Taq High Fidelity' (Life Technologies) as described by Tong et al. (2008) (J Clin Microbiol. 46(8):2652-8) with some minor modifications: Nine microliter of RNA are mixed with 12.5 µl reaction buffer (2-fold, 0.4 mM dNTPs each and 2.4 mM $MgSO_4$), 2 µl magnesium sulphate (5 mM), 0.25 µl primer RES-MOR-HEN-R (100 µM), 0.25 µl primer RES-MOR-HEN-F1 (100 µM), 0.5 µl RNase inhibitor (40 U/µl, Life Technologies) and 0.5 µl SuperScript III/Platinum Taq High Fidelity Enzyme Mix'. Samples are then treated according to the following thermal profile: one minute at 60° C., 30 minutes at 45° C. and 2 minutes at 94° C. After this treatment samples are heated as follows: 45 cycles at 94° C. for 15 seconds, 48° C. for 30 seconds and 68° C. for 30 seconds with a final elongation step at 68° C. for 5 minutes. PCR products are visualized using agarose gel electrophoresis in Tris-acetate-EDTA-buffer (40 mM Tris-acetate, 1 mM EDTA, pH=8.3) including 0.2 µg/ml of ethidium bromide. A specific PCR fragment having a size of about 611 bp is cut out of the gel and purified using the 'Gel/PCR DNA Fragments Extraction Kit' (Geneaid, Taiwan).

Sequencing:
The PCR fragment is sequenced by applying the Sanger didesoxy method using RES-MOR-HEN-R (10 µM) and RES-MOR-HEN-FI (10 µM) as sequencing priming. Resulting chromatograms are edited using the software 'BioEdit' (version 7.2.4) and aligned with the 'Basic Local Alignment Search Tool' (BLAST) on the NCBI website.

Example 2: Isolation of FPaV-2

For virus cultivation LLC-MK2 and CrFK cells are seeded in 75 cm² cell culture flasks in DMEM (with sodium pyruvat and non-essential amino acids) with 5% of FBS in an atmosphere including 5% carbon dioxide at 37° C. and 90% humidity. At 70-80% confluence cells are infected with a mixture of one milliliter urine and 5 ml DMEM (with penicillin and streptomycin) over night at 37° C., 5% $CO_2$ and 90% humidity.

Figure 1:
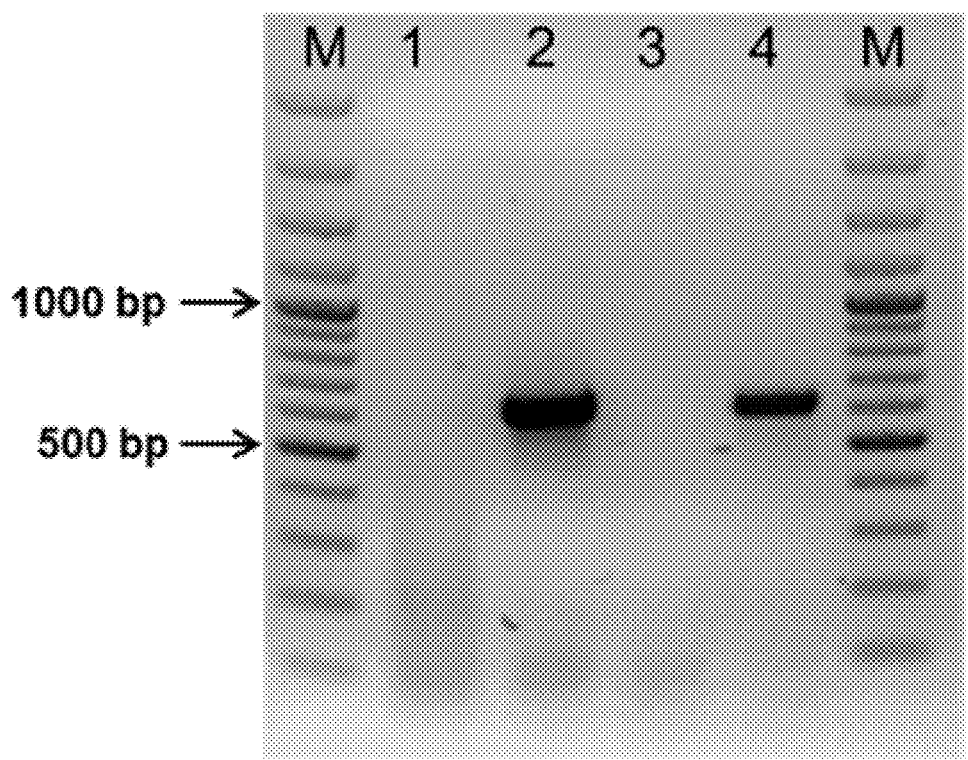
FIG. 1: Detection of feline paramyxovirus (FPaV-2) in cell culture supernatants.

After 24 hours the infection medium was replaced by 8 ml of cultivation medium (DMEM, sodium pyruvat, non-essential amino acids, 5% FBS, penicillin and streptomycin) and cultivated for further 6 days at the indicated conditions. The cell culture supernatant from this infection is passaged for further three times. Afterwards 600 µl of the cell culture supernatant are tested as described in Example 1 for the presence of feline paramyxoviruses. FIG. 1 shows the result of such an experiment.

Example 3: Immunofluorescence Detection of FPaV-2

To detect FPaV-2 infections LLC-MK2 cells are infected as described in Example 2 and stained with a FPaV-2-specific antibody using immunofluorescence techniques.

For this purpose adherent cells are washed with PBS after an infection period of 5 days and subsequently fixed with 80% of acetone at −20° C. for 10 minutes. Cells are washed twice with PBS and unspecific binding is blocked by incubation with 5% BSA in PBS at 37° C. for one hour.

This is followed by an incubation step with anti-FPaV-2 antibody (anti-FPaV-2 nucleocapsid, polyclonal, rabbit) at a final concentration of 1 µg/ml in 1% BSA in PBS for one hour at 37° C. Cells are washed three time with PBS followed by the application of 'Goat anti-Rabbit IgG (H+L) Secondary Antibody, Alexa Fluor® 488 conjugate' (Thermo Fisher Scientific) at a final dilution of 1:1000 in 1% BSA in PBS. After an incubation time of one hour at 37° C. cells are washed twice with PBS and cells were screened for the presence of FPaV-2 using a fluorescence microscope. Results are shown in FIG. 2.

Example 4: Infection Spectrum of FPaV-2

To analyze the in vitro susceptibility of FPaV-2 different cell lines are infected and then analyzed using immunofluorescence techniques as described in Example 3. Table 3 reflects the result of such an experiment.

TABLE 3 in vitro spectrum of FPaV-2 infection

| Cell line | Tissue | Species | Infektion with FPaV-2 |
|---|---|---|---|
| CrFK | Kidney, epithel | Cat | positive |
| CrFK/CatSLAM | Kidney, epithel, transfected with feline CD150 | Cat | positive |
| FE | Embryonal, epithelial and fibroblastic | Cat | positive |
| Vero (CCL-81) | Kidney, epithel | Vervet monkey | positive |
| LLC-MK2 | Kidney, epithel | Rhesus monkey | positive |
| BHK-21 | Kidney, fibroblast | Syrian golden hamsters | positive |

Example 5: Infection of Feline Primary Kidney Cells with FPaV-2

To investigate whether primary cells are also susceptible to FPaV-2 primary feline kidney cells are isolated. For this purpose kidneys from an euthanized cat are removed under aseptic conditions and stored on ice immediately. Then the capsule is detached and the cortex is cut into small pieces and rinsed five times in HBSS. These tissue pieces are then treated with 0.1 percent of trypsin in HBSS for 20 minutes at 37° C. in a vertical shaker. The cell suspension is filtered through a 100 μm nylon filter and the filtrate is centrifuged at 400×g for 10 minutes. The cell pellet is re-suspended in complete kidney medium (1:1 mixture of DMEM and Hams-F12 medium supplemented with 'Insulin-Transferrin-Selenium-Ethanolamine' [Thermo Fisher Scientific], sodium pyruvate, non-essential amino acids, 10% FBS, penicillin and streptomycin), seeded out in tissue flasks and incubated at 37° C., 5% $CO_2$ and 90% humidity. FIG. 3 shows a typical result of such an experiment.

The previously described primary feline kidney cells are infected with FPaV-2 as described in Example 2 and stained for the presence of FPaV-2 as described in Example 3. FIG. 4 shows a result of such an experiment.

Example 6: Determination and Analysis of the Full-Length FPaV-2 Genome

For obtaining the whole genome sequence of the FPaV-2-cell culture isolate 'Gordon' RNA is isolated from the cell culture supernatant as described in Example 1. FPaV-2-specific PCR products are then generated by using the one-step-PCR-system described in example no. 1 and a primer-walking strategy. Amplification products are isolated from the agarose gel with the help of the ' Gel/PCR DNA Fragments Extraction Kit' (Geneaid) and sequenced by the sanger didesoxy method with the corresponding amplification primers. Each PCR fragment is sequenced twice. The alignment result of the obtained FPaV-2 sequence with the FmoPV-isolate M252A (Woo et al. (2012), Proc. Nat. Acad. Sci. 109(14):5435-5440); Accession number: JQ411016.1) is shown in table 4.

Example 7: Prevalence of FPaV-2 in Urine Samples

To elucidate the prevalence of FPaV-2 in domestic cats, urine samples were collected by cystocentesis, stored immediately at −20° C. and analyzed for the presence of FPaV-2-RNA as described in example 1. Results are shown in table 5.

TABLE 5

Prevalence of FPaV-2 in urine samples of domestic cats

| Characteristics | Diseased group | Healthy group |
| --- | --- | --- |
| Number of tested urines | 325 | 238 |
| Clinical and laboratory findings | FLUTD, nephritis, anuria, polyuria, urolithiasis, cystitis, hematuria, leukocyturia, lipiduria, proteinuria | No history of urotract diseases |
| Mean age in years | 8 (1-19 years) | 10 (0.5-21 years) |
| Male cats | 72% | 61% |
| RT-PCR positive | 4 (1.2%) | 0 (0%) |

Example 8: Heterogeneity of FPaV-2 Strains

Using the procedure described in example 1, a second strain of FPaV-2 was isolated from a male cat suffering from feline urologic syndrome. The viral isolate (named 'TV25') was subjected to whole genome sequencing using primer walking strategy and sanger dideoxy DNA sequencing method. Results are summarized in table 6, nucleotide sequence is shown in SEQ ID NO:8.

TABLE 4

Analysis of whole genome sequence of FPaV-2 (strain, Gordon')

| Genome region | Nucleotide position (cRNA) | Nucleotide homology to FmoPV-M252A (nt's/nt's) | Amino acid homology to FmoPV M252A (aa/aa) |
| --- | --- | --- | --- |
| 3' untranslated Region (UTR) | 1-107 | 84.1% (90/107) | not applicable |
| Nucleocapsid protein | 108-1667 | 81.1% (1266/1560) | 89.8% (466/519) |
| Intergenic sequence | 1668-1780 | 39.8% (45/113) | not applicable |
| Phospho protein | 1781-3256 | 80.5% (1188/1476) | 75.1% (369/491) |
| Intergenic sequence | 3257-3388 | 44.7% (59/132) | not applicable |
| Matrix protein | 3389-4402 | 83.3% (845/1014) | 91.7% (309/337) |
| Intergenic sequence | 4403-4949 | 48.6% (268/551) | not applicable |
| Fusion protein | 4950-6581 | 80.9% (1320/1632) | 88.7% (482/543) |
| Intergenic sequence | 6582-6958 | 56% (211/377) | not applicable |
| Hemagglutinin protein | 6959-8746 | 80.5% (1435/1788) | 85.9% (511/595) |
| Intergenic sequence | 8747-8887 | 54.6% (77/141) | not applicable |
| Polymerase protein | 8888-15496 | 82.5% (5453/6609) | 90.9% (2001/2202) |
| 5' untranslated region (UTR) | 15497-16047 | 52.4% (289/551) | not applicable |
| Whole genome | 1-16047 | 78.2% (12546/16047) | not applicable | nt's: nucleotides aa: amino acids

TABLE 6

Comparison of whole genome sequences of the two FPaV-2 isolates 'Gordon' and 'TV25'

| Genome region | Nucleotide position (cRNA) | Nucleotide similarity between 'Gordon' and 'TV25' (nucleotides) | Amino acid similarity between 'Gordon' and 'TV25' (amino acids) |
| --- | --- | --- | --- |
| 3' untranslated Region (UTR) | 1-107 | 100% (107/107) | not applicable |
| Nucleocapsid protein | 108-1667 | 99.2% (1547/1560) | 99.2% (515/519) |
| Intergenic sequence | 1668-1780 | 98.2% (111/113) | not applicable |
| Phospho protein | 1781-3256 | 99.6% (1470/1476) | 98.8% (485/491) |
| Intergenic sequence | 3257-3388 | 98.5% (130/132) | not applicable |
| Matrix protein | 3389-4402 | 99.4% (1008/1014) | 99.7% (336/337) |
| Intergenic sequence | 4403-4949 | 98% (540/551) | not applicable |
| Fusion protein | 4950-6581 | 99.4% (1622/1632) | 99.4% (540/543) |
| Intergenic sequence | 6582-6958 | 97.6% (368/377) | not applicable |
| Hemagglutinin protein | 6959-8746 | 99.2% (1774/1788) | 99.5% (592/595) |
| Intergenic sequence | 8747-8887 | 97.9% (138/141) | not applicable |
| Polymerase protein | 8888-15496 | 99.2% (65 54/6609) | 99.5% (2191/2202) |
| 5' untranslated region (UTR) | 15497-16047 | 99.4% (548/551) | not applicable |
| Whole genome | 1-16047 | 99.2% (15917/16047) | not applicable |

Example 9: Electron Microscopy of FPaV-2

15 ml of the a FPaV-2-cell culture supernatant (described in example 2) was centrifuged at 3.000×g for 10 minutes at 4° C. followed by filtration through a 0.45 µm cellulose nitrate filter. The filtrate was overlayed on a 20% (w/v) sucrose cushion and centrifuged at 100.000×g for 90 minutes at 4° C. The pellet was then suspended in 100 µl of PBS and the virus was allowed to absorb to a formvar/carbon coated 300 mesh copper grid for five minutes at room temperature. After three washing steps with distillated water viral particles were stained with 2% (w/v) uranyl acetate for 30 seconds. Analysis of this sample using a transmission electron microscope revealed typical paramyxoviral morphology: pleomorphic, enveloped viral particles having a size of 100-150 nanometers.

Example 10: Antibody Diversity of FPaV-2-Infected Cats

To investigate the antibody diversity of cats being naturally infected with FPaV-2, semi-purified viral particles (as shown in example 9) were mixed with an equal volume of SDS-loading buffer (100 mM Tris-HCl, pH 6.8; 4% (w/v) sodium dodecyl sulfate; 0.2% (w/v) bromophenol blue; 20% (v/v) glycerol; 200 mM β-mercaptoethanol), heated at 95° C. for five minutes and loaded onto an 8% polyacrylamide gel. Viral proteins were separated by electrophoresis at 130 V for 90 minutes in SDS-PAGE running buffer (25 mM Tris, 192 mM glycine, 0.1% SDS) followed by blotting to a nitro cellulose membrane.

After blocking with 5% (w/v) non-fat dry milk in PBS-T (0.05 tween 20) for 30 minutes at room temperature the membrane was incubated over night at 4° C. with cat serum samples diluted 1:100 in block buffer. The membrane was washed three times with PBS-T and incubated with horseradish peroxidase conjugated α-Cat-IgG antibody diluted 1:1.000 in blocking buffer for one hour at room temperature. 3,3'-Diaminobenzidine was used for signal development. As shown in FIG. 5A, FPaV-2-infected cats can develop antibodies against a broad spectrum of viral structural proteins, e.g. the polymerase-, phospho-, nucleocapsid- and hemagglutinin-protein. Specific reactions to viral proteins were annotated based on their reactivity with target antibodies as shown for the nucleocapsid-protein (FIG. 5C).

The phospho-protein was proved to be heavily phosphorylated using a phospho-serine Antibody (Q5 from QIAGEN N.V.) shifting the calculated molecular weight from 53 kDa to about 75 kDa. This phenomenon of molecular weight shift is known from other morbilliviruses like Measles Virus (phospho-protein=70 kDa) and Canine Distemper Virus (phospho-protein=73 kDa). Annotations of specific reactions against the polymerase- and hemagglutinin-protein were done based on the predicted molecular weight from their amino acid sequences.

Example 11: Development of a Serum Neutralization Test for FPaV-2

To detect neutralizing antibodies against FPaV-2 a serum neutralization assay (SNT) was established. Therefore, cat serum samples were treated at 56° C. for 30 minutes to inactivate complement factors. 50 µl of these heat inactivated serum samples were mixed with 50 µl DMEM containing 100 fluorescence forming units (FFU) of FPaV-2 (isolate 'Gordon') and were then incubated for one hour at 4° C. The mixture was used to infect LLC-MK2-cells in a 96-well cell culture plate for two hours at 37° C. Then the serum/virus-mixture was removed and replaced by DMEM containing 2% (v/v) heat inactivated FBS, sodium pyruvate, non-essential amino acids, penicillin and streptomycin. The cells were incubated for five days at 37° C., 5% $CO_2$ and 90% humidity followed by immunofluorescence staining as described in example 3. The neutralization titer of the test serum sample is defined as the reciprocal of the highest test serum dilution for which the virus infectivity is reduced by 50% when compared to the virus control without serum incubation.

Example 12: Screening for Neutralizing Antibodies in FPaV-2-Infected Cats

Serum samples of naturally FPaV-2-infected cats were screened for the presence of neutralizing antibodies using the SNT described in example 11. The results of these experiments are shown in table 7. They clearly show that an FPaV-2-infection can induce high titers of neutralizing antibodies against the virus (see FPaV-2-SNT results of cat serum samples 98450 and TV25 in table 7). In contrast, serum samples from canine distemper virus-infected cats (sample CDV in table 7) and feline paramyxovirus-negative (sample TV26 in table 7) cats show no neutralizing antibodies, highlighting that the detected antibody titers are FPaV-2 specific.

TABLE 7

Results of FPaV-2 serum neutralization tests.

| Cat serum ID | 98450 | TV25 | TV26 | CDV |
|---|---|---|---|---|
| PCR result from urine | FPaV2 positive | | Paramyxovirus negative | — |
| Presence of viral RNA in urine | >14 weeks | >18 months | — | — |
| IFA | Pos. | Pos. | Neg. | Neg. |
| FPaV-2 SNT titer | 320 | 320 | <10 | <10 |

IFA: immune fluorescence assay,
CDV: canine distemper virus-positive sample

Example 13: ELISA-Development for Screening of FPaV-2 Antibodies in Cat Serum Samples To elucidate the prevalence of FPaV-2 infections in German cat populations, an ELISA-system based on recombinant expressed nucleocapsid was established. Therefore, the complete open-reading frame of the FPaV-2-nucleocapsid (SEQ ID NO:2) was cloned into the expression vector 'pGEX-4T-1' using the restriction enzymes BamHI and XhoI. The resulting recombinant expression plasmid ('pGEX-Gordon-NC') was transformed into chemical competent $E.\ coli$ BL21(DE3) by standard techniques and recombinant bacteria were selected on LB-agar with 100 µg/ml Ampicillin resulting in an $E.\ coli$-clone named '$E.\ coli$-Gordon-NC'. This clone was inoculated into 1.000 ml LB medium with 0.2% glucose and 100 µl/ml ampicillin and was shaken at 37° C. with 200 rpm until the culture reached an optical density of $A_{600}$ nm=1.0. At that point the culture was cooled down to 22° C. and recombinant protein expression was induced with Isopropyl β-D-1-thiogalactopyranoside (IPTG) at a final concentration of 0.1 mM. After incubating for 20 hours at 22° C. and 220 rpm the culture was centrifuged at 3.000×g, 4° C. for 20 minutes and the resulted pellet was sonicated to disrupt the $E.\ coli$ cells. Purification of recombinant GST-fusion protein was performed using Glutathione Sepharose 4B (GE Healthcare Life Science) as described by the manufacture.

200 ng of the resulted GST-Gordon-NC-protein was coated per well in a Nunc MaxiSorp ELISA plate over night at 4° C. followed by three washing steps with PBS-T (0.05% tween 20). Free protein binding sites were blocked using 5% (w/v) non-fat dry milk in PBS-T (blocking buffer) for 30 minutes at 37° C. Serum samples were diluted 1:100 in blocking buffer and incubated for two hours at 37° C. on the primed ELISA-plate. After three washing steps with PBS-T, wells were incubated with secondary antibody (goat anti cat IgG (Fc):HRP, Bio-Rad, diluted 1:10.000 in blocking buffer) for one hour at 37° C. Unbound antibody was washed off by three PBS-T washing cycles and subtract solution (OPD Substrate Tablets, Thermo Fisher Scientific) was applied to each wells, incubated for five minutes at 22° C. before enzymatic reaction was stopped by 2.5 M sulfuric acid. Absorbance was measured at 490 nm. To define the cut-off of this ELISA-system, serum samples from cats were screened for FPaV-2-specific reactions applying the immunofluorescence test described in example 3.

Results are shown in FIG. 6. IFA result was set as gold standard and compared to OD values. Samples having in OD value below 0.5 were defined as FPaV-2-negative, whereas samples with an OD value higher than 0.7 were defined to be FPaV-2-positive. 'Borderline'-samples with an OD value between 0.5 and 0.7 need to be checked in IFA to evaluate the ELISA result. Using this approach, 13 out of 230 serum samples (=5.6%) from domestic cats were positive for FPaV-2. This result reflects the relatively high prevalence of FPaV-2 in German cat populations.

Example 14: Primary Target Cells of FPaV-2

Feline PBMCs were in vitro infected with FPaV-2 to uncover whether feline immune cells are also targets of FPaV-2. For this purpose peripheral blood mononuclear cells (PBMCs) were isolated from a healthy male cat using standard Ficoll density gradient centrifugation. PBMCs were treated with 2% (v/v) phytohemagglutinin (M-from, crude extract, Thermo Fisher Scientific) in RPMI for four hours at 37° C. followed by infection with FPaV-2 at an MOI of 0.1 or were mock-infected for two hours at 37° C. PBMCs were washed once with PBS and then incubated at 37° C., 5% $CO_2$ and 90% humidity for 48 hours. Cells were stained for CD4 and CD20 surface markers using standard flow cytometry protocols. After a fixation step with 2% (w/v) paraformaldehyde for 10 minutes at 4° C. cells were intracellularly stained with anti-FPaV-2-nucleocapsid antibody (see example 2) in facs-buffer (PBS, pH=7.4; 3% FBS; 0.1% sodium azide) with 0.5 (w/v) saponin for 30 minutes at 22° C. Stained cells were washed tree times with facs-buffer and analyzed using the LSRFortessa™ (Becton Dickinson) cell analyzer. As shown in FIG. 7 feline CD4-positive T-cells as well as feline CD20-positive B-cells are target cells of FPaV-2. These results clearly indicate that a systemic state of FPaV-2 is likely to occur.

Example 15: Immunization of Rabbits with Inactivated FPaV-2

The aim of this 'proof-of-concept'-experiment was to elucidate whether an immunization with inactivated FPaV-2 will induce neutralizing antibodies and can therefore serve as a potential vaccine candidate. A male rabbit was immunized with a vaccine mixture of 1 ml heat-inactivated (3 hours at 56° C.) FPaV-2-strain 'Gordon' ($1*10^5$ FFU/ml, see example no. 2) and 2 ml an adjuvant (92.8% mineral oil; 3.48% Tween 80; 3.48% Span 80; 23% lipopolysaccharide). For the negative control animal the same volume of a cell culture supernatant from a mock-infection (no virus) mixed with the adjuvant was used instead of FPaV-2.

Immunization was done according to the following scheme:

$1^{st}$ Immunization: Collecting of pre-immune serum, 1 ml subcutaneous and 1 ml intramuscular of vaccine mixture was than inoculated.

$2^{nd}$ Immunization 14 days after $1^{st}$ immunization: 1 ml subcutaneous and 1 ml intramuscular of vaccine mixture was inoculated.

$3^{rd}$ Immunization 7 days after $2^{nd}$ immunization: 1 ml subcutaneous and 1 ml intramuscular of vaccine mixture was inoculated.

final bleed (rabbits were killed): 14 days after the third immunization

The final serum samples were first tested in a western-blot analysis using a whole virus preparation as described in example 10. This experiment showed that five weeks after immunization specific antibodies against the polymerase-, phospho-, hemagglutinin- and nucleocapsid-protein were detected in the FPaV-2 vaccinated animal (see FIG. 8B). The specificity of the observed reactions was confirmed by analyzing the pre-immune serum of this rabbit. As shown in FIG. 8A no virus-specific antibodies were present before immunization. In addition, the staining pattern of the post-immunization serum sample (FIG. 8B) was identical to the results from naturally FPaV-2-infected cats (see FIG. 5A) proving the virus-specific nature of the observed bands in the presented western-blot analyses. Thus, the applied FPaV-2 vaccination formula is able to induce a broad spectrum of anti-FPaV-2 antibodies in animals. To elucidate whether these antibodies have neutralizing properties an FPaV-2-SNT was performed (described in example 11) using the serum samples collected five weeks after immunization with FPaV-2 or with the cell culture supernatant from a mock-infection. The results are shown in table 8.

TABLE 8

FPaV-2-SNT result of immunized rabbit.

| Rabbit no. | 1 | 2 |
|---|---|---|
| Immunogen | Heat inactivated cell culture supernatant from a mock-infection | Heat-inactivated cell culture supernatant from a FPaV-2 infection ('Gordon' strain) |

TABLE 8-continued

FPaV-2-SNT result of immunized rabbit.

| Rabbit no. | 1 | 2 |
|---|---|---|
| SNT result: | | |
| Serum dilution (samples 5 weeks after immunization) | Virus neutralizing activity of serum dilution | |
| 1:10 | Negative | Positive |
| 1:20 | Negative | Positive |
| 1:40 | Negative | Positive |
| 1:80 | Negative | Positive |
| 1:160 | Negative | Positive |
| 1:320 | Negative | Negative |
| 1:640 | Negative | Negative |
| 1:1280 | Negative | Negative |
| SNT-Titer | <10 | 160 |

Rabbits were immunized with either heat-inactivated FPaV-2 strain 'Gordon' (rabbit no. 2) or with cell culture supernatant as a negative control (rabbit no. 1) as described in example 15. Five weeks after immunization serum samples of these rabbits were tested for the presence of neutralizing antibodies against FPaV-2. "Positive" in table 8 means no virus growth, i.e. there is virus neutralization activity. Virus growth was measured via immunofluorescence staining according to Example 3.

These experiments clearly show that a heat inactivated FPaV-2 formula can induce a high titer of neutralizing antibodies which are able to inhibit virus infection. Although tested in rabbits it can be assumed that a similar vaccination strategy would be effective in other animals like domestic cats.

The invention claimed is:

1. A nucleic acid comprising a nucleotide sequence encoding a paramyxovirus wherein the nucleotide sequence comprises a polynucleotide selected from the group consisting of
   a DNA sequence being at least 80% identical to SEQ ID NO: 1 or SEQ ID NO:8 and
   the complementary strand of any of the nucleotide sequences thereof.

2. A vector comprising the nucleic acid according to claim 1.

3. A host cell comprising the vector according to claim 2.

4. A polypeptide having an amino acid sequence encoded by the nucleic acid of claim 1 [selected from the group consisting of
   (a) an amino acid sequence which is at least 90% identical to SEQ ID NO:2 or 9,
   (b) an amino acid sequence which is at least 76% identical to SEQ ID NO:3 or 10,
   (c) an amino acid sequence which is at least 92% identical to SEQ ID NO:4 or 11,
   (d) an amino acid sequence which is at least 89% identical to SEQ ID NO:5 or 12,
   (e) an amino acid sequence which is at least 86% identical to SEQ ID NO:6 or 13, or
   (f) an amino acid sequence which is at least 91% identical to SEQ ID NO:7 or 14].

5. An immunogenic composition comprising at least one member selected from the group consisting of:
   (a);
   a nucleic acid according to claim 1;
   (b) a polypeptide according to claim 4; and
   (c)
   a polypeptide according to claim 4, which is fused to a heterologous or autologous (poly-)peptide,
   wherein the composition further comprises a pharmaceutically acceptable carrier or excipient suitable for intradermal or intramuscular application, and
   optionally said immunogenic composition further comprises an adjuvant.

6. A kit [for vaccinating a feline against a disease associated with and/or reducing the incidence or the severity of one or more clinical signs associated with or caused by a paramyxovirus in a subject] comprising:
   (a) a dispenser capable of administering a vaccine to the subject;
   (b) the immunogenic composition according to claim 5; and
   (c) optionally an instruction leaflet.

7. An immunogenic composition comprising; the paramyxovirus which is deposited under accession no. CNCM I-5123 or the paramyxovirus which is deposited under accession no. CNCM I-5123 wherein the paramyxovirus is attenuated, a pharmaceutically acceptable carrier or excipient suitable for intradermal or intramuscular application, and optionally said immunogenic composition further comprises an adjuvant.

* * * * *